United States Patent
Kim et al.

(10) Patent No.: US 10,516,114 B2
(45) Date of Patent: Dec. 24, 2019

(54) COMPOUND FOR ORGANIC OPTOELECTRIC DEVICE, COMPOSITION FOR ORGANIC OPTOELECTRIC DEVICE AND ORGANIC OPTOELECTRIC DEVICE AND DISPLAY DEVICE

(71) Applicants: SAMSUNG SDI CO., LTD., Yongin-si, Gyeonggi-do (KR); SAMSUNG ELECTRONICS CO., LTD., Suwon-si, Gyeonggi-do (KR)

(72) Inventors: Byungku Kim, Suwon-si (KR); Dong Min Kang, Suwon-si (KR); Jun Seok Kim, Suwon-si (KR); Hyung Sun Kim, Suwon-si (KR); Chang Ju Shin, Suwon-si (KR); Eun Sun Yu, Suwon-si (KR); Yuna Jang, Suwon-si (KR); Sung-Hyun Jung, Suwon-si (KR)

(73) Assignees: Samsung SDI Co., Ltd., Yongin-Si, Gyeonggi-do (KR); Samsung Electronics Co., Ltd., Suwon-Si, Gyeonggi-do (KR)

( * ) Notice: Subject to any disclaimer, the term of this patent is extended or adjusted under 35 U.S.C. 154(b) by 0 days.

(21) Appl. No.: 15/677,405

(22) Filed: Aug. 15, 2017

(65) Prior Publication Data

US 2018/0090689 A1 Mar. 29, 2018

(30) Foreign Application Priority Data

Sep. 28, 2016 (KR) ........................ 10-2016-0125110

(51) Int. Cl.
| | | |
|---|---|---|
| C07D 209/86 | (2006.01) |
| C07D 251/24 | (2006.01) |
| H01L 51/00 | (2006.01) |
| H01L 51/50 | (2006.01) |
| H01L 51/52 | (2006.01) |

(52) U.S. Cl.
CPC ........ *H01L 51/0072* (2013.01); *C07D 209/86* (2013.01); *C07D 251/24* (2013.01); *H01L 51/0052* (2013.01); *H01L 51/0054* (2013.01); *H01L 51/0067* (2013.01); *H01L 51/0085* (2013.01); *H01L 51/5016* (2013.01); *H01L 51/5056* (2013.01); *H01L 51/5088* (2013.01); *H01L 51/5096* (2013.01); *H01L 51/5206* (2013.01); *H01L 51/5221* (2013.01); *H01L 2251/5384* (2013.01)

(58) Field of Classification Search
CPC . C07D 209/86; C07D 251/24; H01L 51/0067; H01L 51/0072; H01L 51/5016; H01L 51/5056; H01L 51/5088; H01L 51/5096; H01L 51/5206; H01L 51/5221; H01L 51/0052; H01L 51/0054; H01L 2251/5384
See application file for complete search history.

(56) References Cited

U.S. PATENT DOCUMENTS

2015/0228908 A1* 8/2015 Lee ................... H01L 51/0067 257/40
2016/0301012 A1* 10/2016 Han .................... H01L 51/0067

FOREIGN PATENT DOCUMENTS

| JP | 3139321 B2 | 2/2001 | |
| JP | 4794919 B2 | 10/2011 | |
| JP | 2012-049518 A | 3/2012 | |
| JP | 2013-016717 A | 1/2013 | |
| JP | 5584702 B | 9/2014 | |
| JP | 2014-185128 A | 10/2014 | |
| JP | 5727237 B | 6/2015 | |
| JP | WO 2013-146117 A | 12/2015 | |
| JP | 2016092412 A * | 5/2016 | ......... H01L 51/0059 |
| KR | 10-2013-0100236 A | 9/2013 | |
| KR | 10-2013-0108265 A | 10/2013 | |
| KR | 10-2015-0028579 | 3/2015 | |
| KR | 10-2015-0034664 A | 4/2015 | |
| KR | 10-2015-0036600 A | 4/2015 | |
| KR | 10-2015-0068776 A | 6/2015 | |
| KR | 10-2015-0094398 | 8/2015 | |
| KR | 10-2015-0135091 A | 12/2015 | |
| KR | 10-2016-0026661 | 3/2016 | |
| KR | 10-2016-0028979 A | 3/2016 | |
| KR | 10-2016-0076336 | 6/2016 | |
| KR | 10-2016-0114526 | 10/2016 | |
| WO | WO-2015111848 A1 * | 7/2015 | ........... C07D 401/10 |
| WO | WO-2016104954 A2 * | 6/2016 | ........... C07D 403/04 |
| WO | WO-2016153283 A1 * | 9/2016 | ........... C07D 209/82 |

OTHER PUBLICATIONS

WO 2016104954 English translation (Year: 2016).*
WO 2016153283 English translation (Year: 2016).*
Hikime et. al., English translation of JP 2012-049518, publ. 2012 (Year: 2012).*
Lui et. al., English translation of JP2016-092412, publ. May 23, 2016 (Year: 2016).*
Sasabe, et al., 3,3'-Bicarbazole-Based Host Materials for High-Efficiency Blue' Phosphorescent OLEDs with Extremely Low Driving Voltage, Avanced Materials, 24 (2012) 3212-3217. 2012. (Wiley-VCH verlag GmbH & Co. KGaA, Weinheim).
Kim, et al., Synthesis of 2- and 4-substituted carbazole derivatives and correlation of substitution position with photophysical properties and device preformances of host materials, Organic Electronics 14 (2013) 67-73.

* cited by examiner

*Primary Examiner* — Sarah Pihonak
(74) *Attorney, Agent, or Firm* — Lee & Morse, P.C.

(57) ABSTRACT

Disclosed are a compound for an organic optoelectric device represented by Chemical Formula 1, a composition for an organic optoelectric device, an organic optoelectric device including the same, and a display device. Details of Chemical Formula 1 are the same as those defined in the specification.

19 Claims, 1 Drawing Sheet

COMPOUND FOR ORGANIC OPTOELECTRIC DEVICE, COMPOSITION FOR ORGANIC OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0125110 filed in the Korean Intellectual Property Office on Sep. 28, 2016, the entire contents of which are incorporated herein by reference.

BACKGROUND OF THE INVENTION

1. Field of the Invention

A compound for an organic optoelectric device, a composition for an organic optoelectric device, an organic optoelectric device, and a display device are disclosed.

2. Description of the Related Art

An organic optoelectric device is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

The organic optoelectric device may for example include an organic photoelectric device, an organic light emitting diode, an organic solar cell, an organic photo conductor drum, and the like.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a compound for an organic optoelectric device capable of realizing an organic optoelectric device having high efficiency and a long life-span.

Another embodiment provides a composition for an organic optoelectric device including the compound for an organic optoelectric device.

Yet another embodiment provides an organic optoelectric device including the compound.

Still another embodiment provides a display device including the organic optoelectric device.

According to an embodiment, a compound for an organic optoelectric device represented by Chemical Formula 1 is provided.

[Chemical Formula 1]

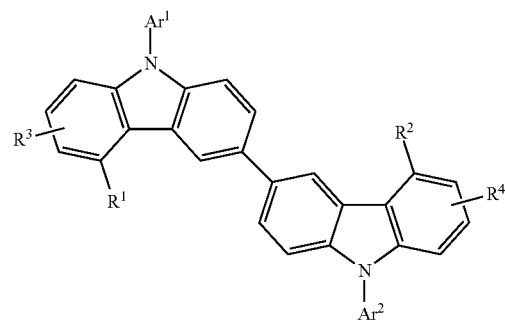

In Chemical Formula 1, $R^1$ to $R^4$ are independently hydrogen, deuterium, a substituted or unsubstituted C1 to C10 alkyl group, or a substituted or unsubstituted C6 to C30 aryl group, at least one of $R^1$ and $R^2$ is a substituted or unsubstituted C6 to C30 aryl group, $Ar^1$ and $Ar^2$ are independently a substituted or unsubstituted C6 to C30 aryl group, a substituted or unsubstituted C2 to C30 heterocyclic group, or a combination thereof, and the "substituted" refers to replacement of at least one hydrogen by deuterium, a C1 to C4 alkyl group, a C6 to C18 aryl group, or a C2 to C18 heteroaryl group.

According to another embodiment, a composition for an organic optoelectric device includes the first compound for an organic optoelectric device; and a second compound for an organic optoelectric device represented by Chemical Formula 2.

[Chemical Formula 2]

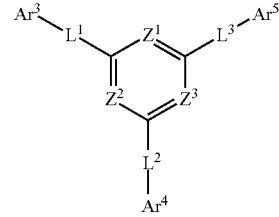

In Chemical Formula 2, $Z^1$ to $Z^3$ are independently N or $CR^a$, at least two of $Z^1$ to $Z^3$ are N, $R^a$'s are independently hydrogen, deuterium, a substituted or unsubstituted C1 to C10 alkyl group, a substituted or unsubstituted C6 to C30 aryl group or a substituted or unsubstituted C2 to C30 heterocyclic group, $R^a$'s are independently present or adjacent groups are linked with each other to provide a substituted or unsubstituted aliphatic, monocyclic or polycyclic ring, a substituted or unsubstituted aromatic monocyclic or polycyclic ring, or a substituted or unsubstituted heteroaromatic monocyclic or polycyclic ring, Ar³ to Ar⁵ are independently a substituted or unsubstituted C6 to C30 aryl group, a substituted or unsubstituted C2 to C30 heterocyclic group, or a combination thereof, L¹ to L³ are independently a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

According to another embodiment, an organic optoelectric device includes an anode and a cathode facing each other and at least one organic layer disposed between the anode and the cathode, wherein the organic layer includes the compound for an organic optoelectric device or the composition for an organic optoelectric device.

According to another embodiment, a display device includes the organic optoelectric device.

An organic optoelectric device having high efficiency and a long life-span may be realized.

DETAILED DESCRIPTION

Figure 1:
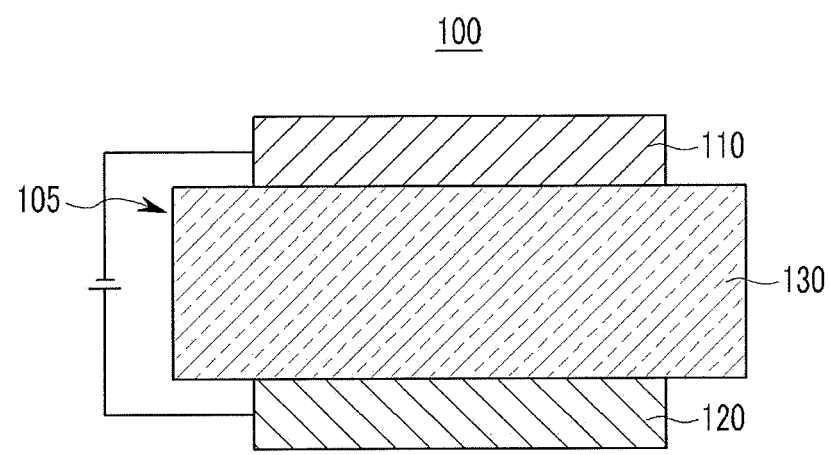
FIGS. 1 and 2 are cross-sectional views showing organic light emitting diodes according to embodiments.

Hereinafter, embodiments of the present disclosure are described in detail. However, these embodiments are exemplary, the present disclosure is not limited thereto and the present disclosure is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a C1 to C10 trifluoroalkyl group, a cyano group, or a combination thereof.

In one example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present disclosure, the "substituted" refers to replacement of at least one hydrogen of a substituent or a compound by deuterium, a C1 to C30 alkyl group, a C6 to C18 aryl group, or a C2 to C20 heteroaryl group. In addition, specific examples of the present disclosure, the "substituted" refers to replacement of at least one hydrogen of a substituent or a compound by deuterium, a C1 to C4 alkyl group, a C6 to C18 aryl group, or a C2 to C18 heteroaryl group.

As used herein, when a definition is not otherwise provided, "hetero" refers to one including one to three heteroatoms selected from N, O, S, P, and Si, and remaining carbons in one functional group.

As used herein, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, "aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectric device according to an embodiment is described.

A compound for an organic optoelectric device according to an embodiment is represented by Chemical Formula 1.

[Chemical Formula 1]

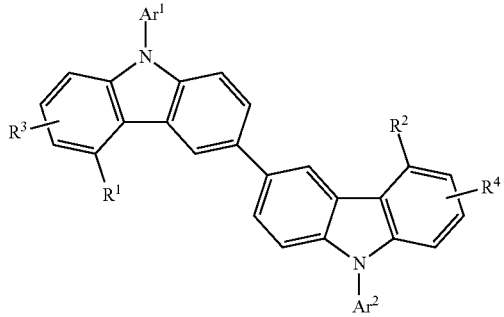

In Chemical Formula 1, $R^1$ to $R^4$ are independently hydrogen, deuterium, a substituted or unsubstituted C1 to C10 alkyl group, or a substituted or unsubstituted C6 to C30 aryl group, at least one of $R^1$ and $R^2$ is a substituted or unsubstituted C6 to C30 aryl group, $Ar^1$ and $Ar^2$ are independently a substituted or unsubstituted C6 to C30 aryl group, a substituted or unsubstituted C2 to C30 heterocyclic group, or a combination thereof, and the "substituted" refers to replacement of at least one hydrogen by deuterium, a C1 to C4 alkyl group, a C6 to C18 aryl group, or a C2 to C18 heteroaryl group.

The "substituted" may specifically refer to replacement of at least one hydrogen by deuterium, a C1 to C4 alkyl group, a phenyl group, a biphenyl group, a naphthyl group, a triphenylene group, a fluorenyl group, a carbazolyl group, a dibenzofuranyl group, a dibenzothiophenyl group, a pyrimidinyl group, a triazinyl group, an indolocarbazolyl group, a benzofurancarbazolyl group, a benzothiophenecarbazolyl group, a benzofuranpyrimidinyl group, or a benzothiophenepyrimidinyl group.

The compound for an organic optoelectric device according to the present disclosure includes a bicarbazole backbone and thus has excellent hole transport characteristics and simultaneously, is substituted with an aryl group at No. 4 of the bicarbazole to facilitate a hole injection and thus shows much faster hole transport characteristics and resultantly, may exhibit a device performance such as a low driving voltage and high efficiency.

In particular, when the aryl group is substituted at No. 4 of the bicarbazole, the compound may have much shallow HOMO energy and thus transfer holes to a dopant without a trap and resultantly, secure a fast driving voltage. The substituent at No. 4 may decrease a deposition temperature and thus increase thermal. and electrochemical stability of molecules.

In an example embodiment, the compound may be for example represented by one of Chemical Formula 1-1 to Chemical Formula 1-3 according to substitution positions of $R^2$ and $R^3$ of Chemical Formula 1.

[Chemical Formula 1-1]

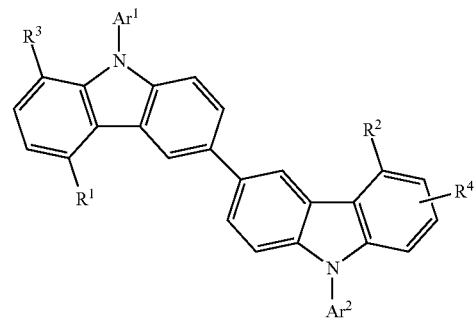

[Chemical Formula 1-2]

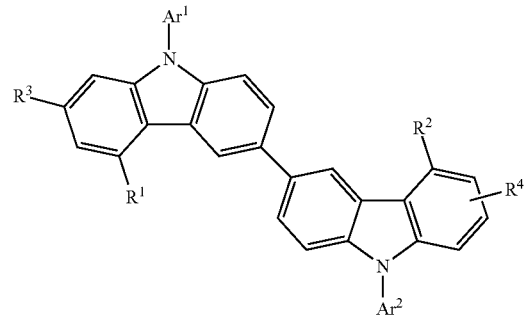

[Chemical Formula 1-3]

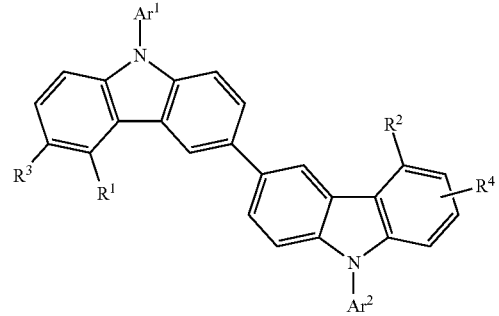

In Chemical Formulae 1-1 to 1-3, $R^1$ to $R^4$ and $Ar^1$ and $Ar^2$ are the same as described above.

In an example embodiment, $R^1$ may be selected from a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group and $R^2$ to $R^4$ may be selected form hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, and a substituted or unsubstituted triphenylene group, and more specifically each of $R^2$ to $R^4$ may be hydrogen.

In another example embodiment, $R^1$ and $R^2$ may independently be selected from a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group, the $R^3$ and $R^4$ are independently hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, and a substituted or unsubstituted triphenylene group, and more specifically each of $R^3$ and $R^4$ may be hydrogen.

Specifically, $R^1$ may be selected from substituents of Group I and $R^2$ to $R^4$ may independently be hydrogen or selected from substituents of Group I.

[Group I]

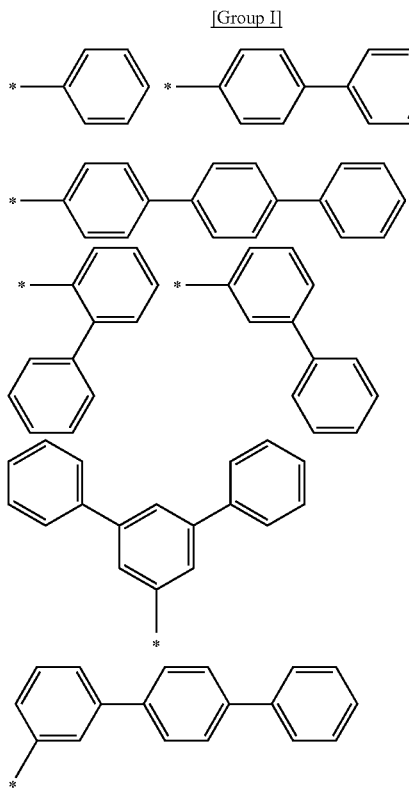

-continued

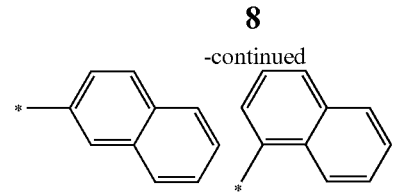

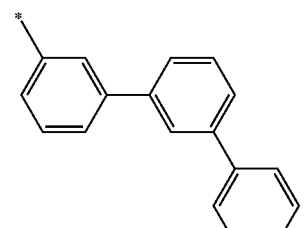

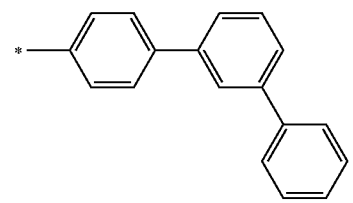

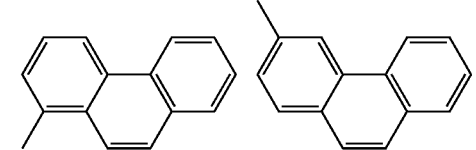

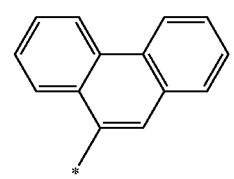

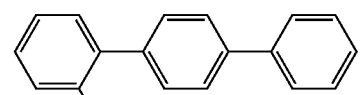

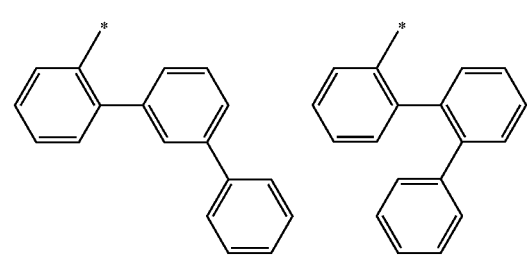

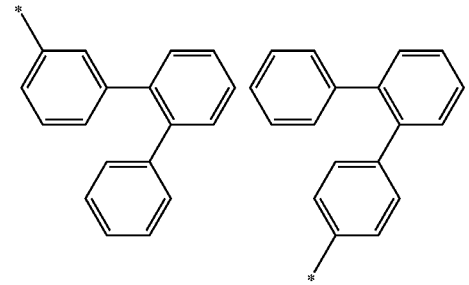

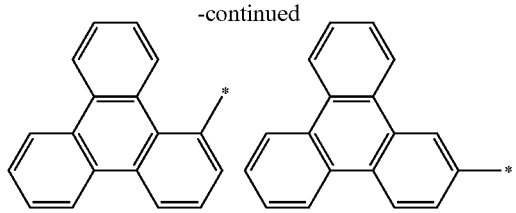

In Group I, * is a linking point with an adjacent atom.

For example, $R^1$ may be a substituted or unsubstituted phenyl group, a substituted or unsubstituted biphenyl group, a substituted or unsubstituted naphthyl group, or a substituted or unsubstituted triphenylene group, the $R^2$ is hydrogen, or a substituted or unsubstituted phenyl group, a substituted or unsubstituted biphenyl group, or a substituted or unsubstituted triphenylene group, and $R^3$ and $R^4$ may be hydrogen.

In addition, in an example embodiment, $Ar^1$ and $Ar^2$ may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, or a combination thereof.

Specifically, $Ar^1$ and $Ar^2$ may independently selected from substituents of Group I and may be for example selected from a substituted or unsubstituted phenyl group, a substituted or unsubstituted biphenyl group, and a substituted or unsubstituted terphenyl group.

In a specific example embodiment, at least one of $R^1$ and $R^2$ may be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, or a substituted or unsubstituted triphenylene group, $Ar^1$ and $Ar^2$ may independently be a substituted or unsubstituted phenyl group, a substituted or unsubstituted biphenyl group, or a substituted or unsubstituted terphenyl group.

In the most specific example embodiment, $R^1$ may be a phenyl group, a m-biphenyl group, a p-biphenyl group, a naphthyl group, or a triphenylene group and $R^2$ may be hydrogen, a phenyl group, a m-biphenyl group, a p-biphenyl group, or a triphenylene group, $R^3$ and $R^4$ may be hydrogen, and $Ar^1$ and $Ar^2$ may independently be a phenyl group, a biphenyl group, or a naphthyl group, but are not limited thereto.

In one example of the present disclosure, $R^3$ and $R^4$ may independently be hydrogen, deuterium, or a substituted or unsubstituted C1 to C10 alkyl group and may independently be hydrogen or deuterium. In a specific example, $R^3$ and $R^4$ may be all hydrogen.

The compound for an organic optoelectric device represented by Chemical Formula 1 may be for example selected from compounds of Group 1, but is not limited thereto.

[Group 1]

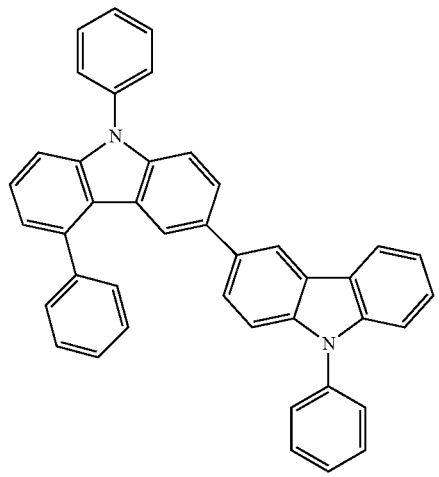

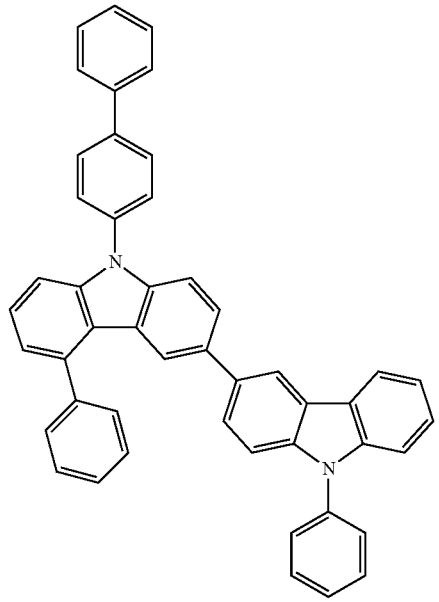

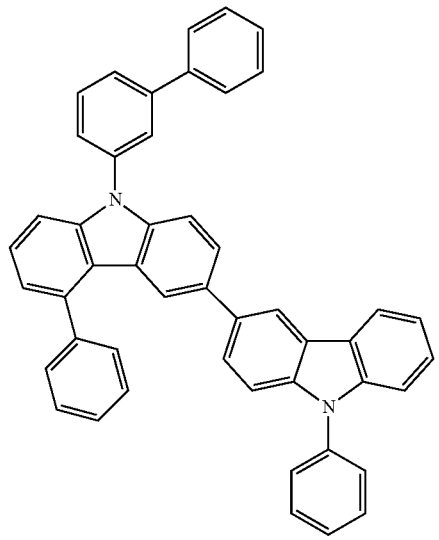

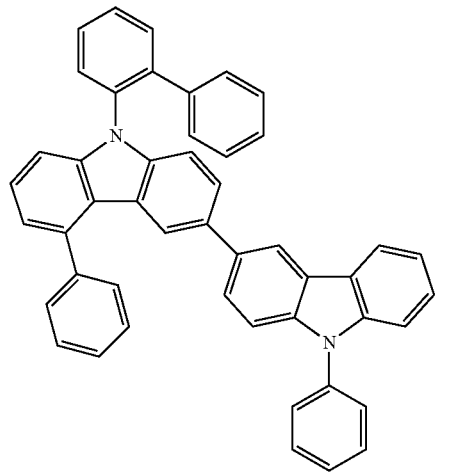
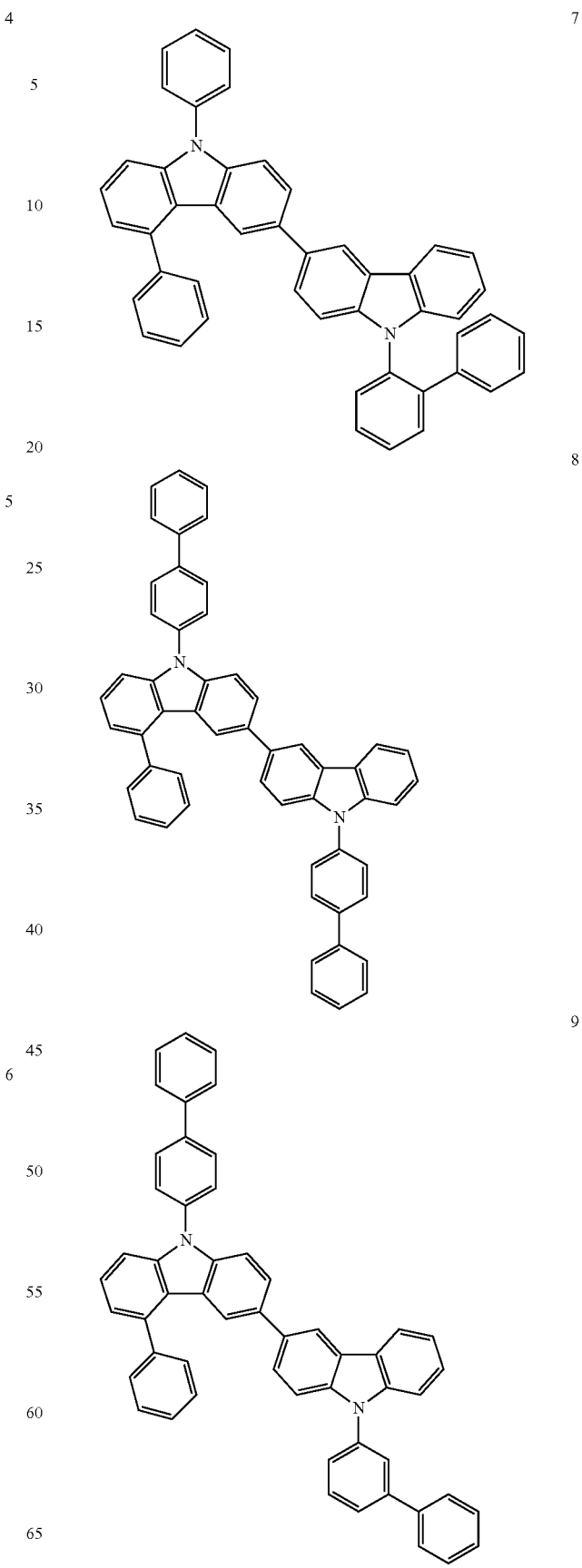

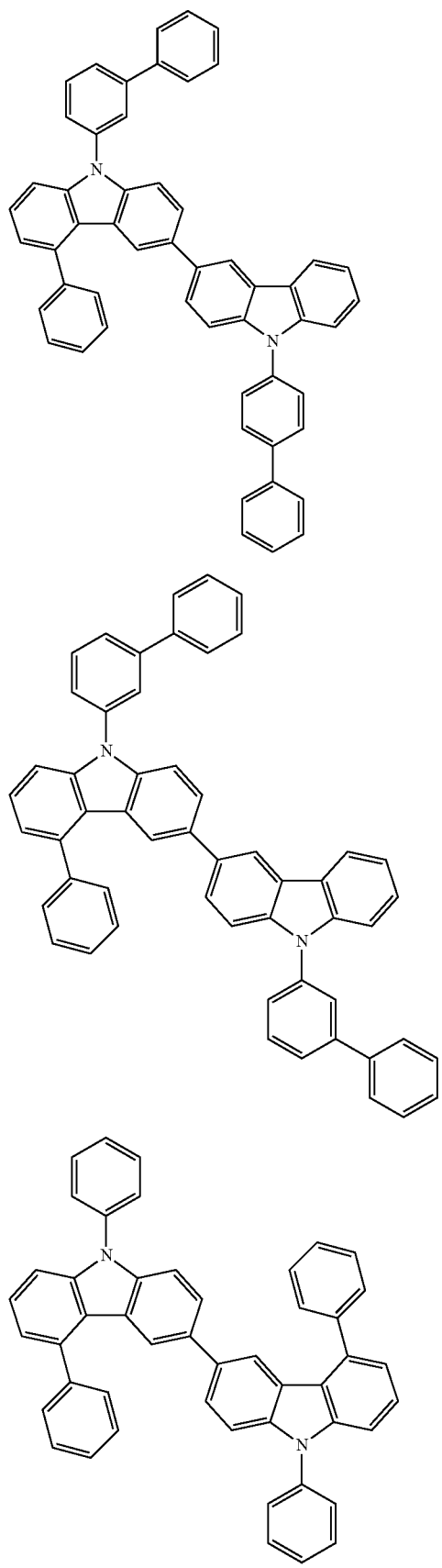
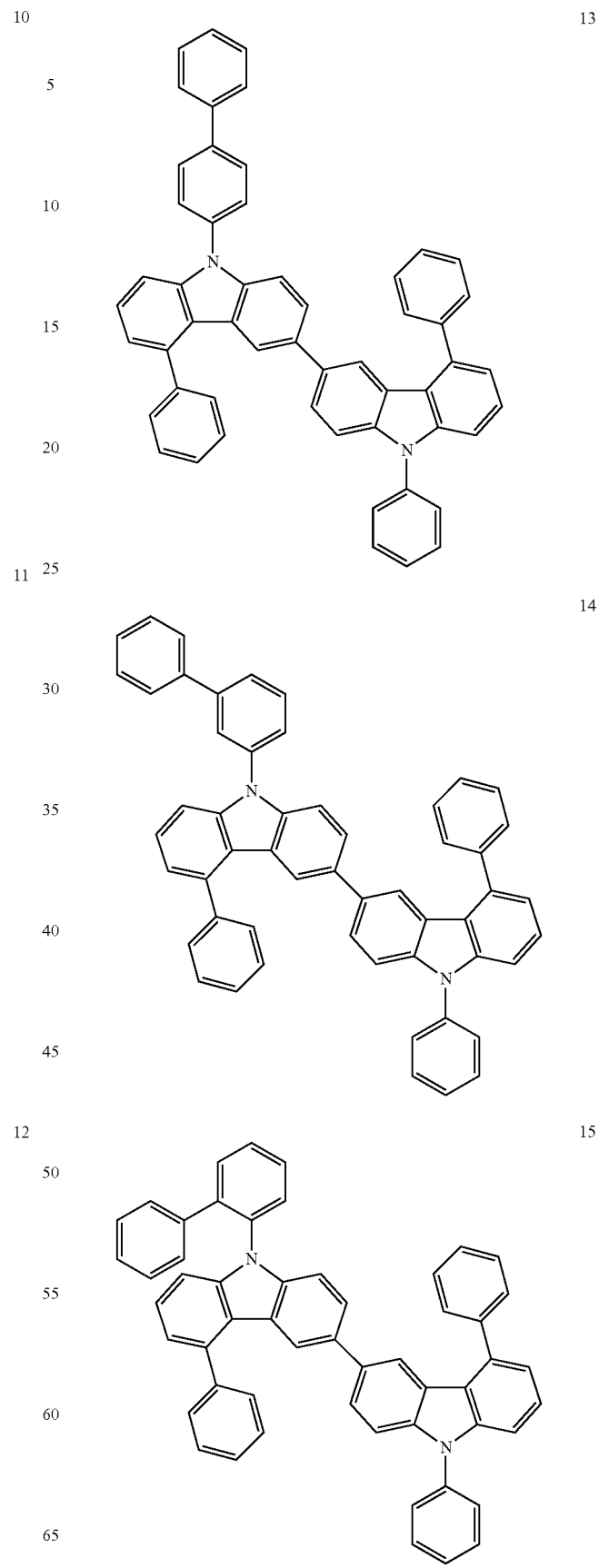

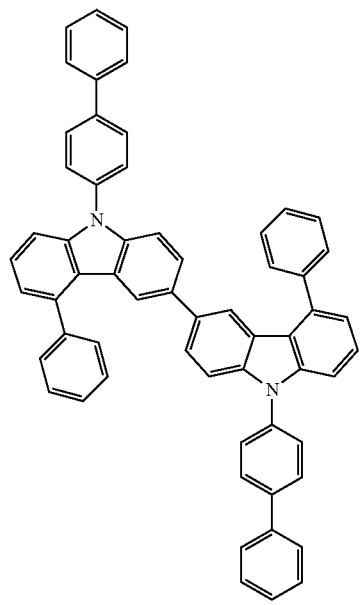
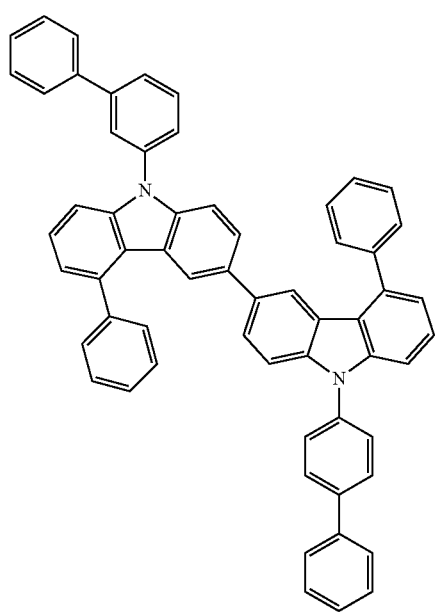
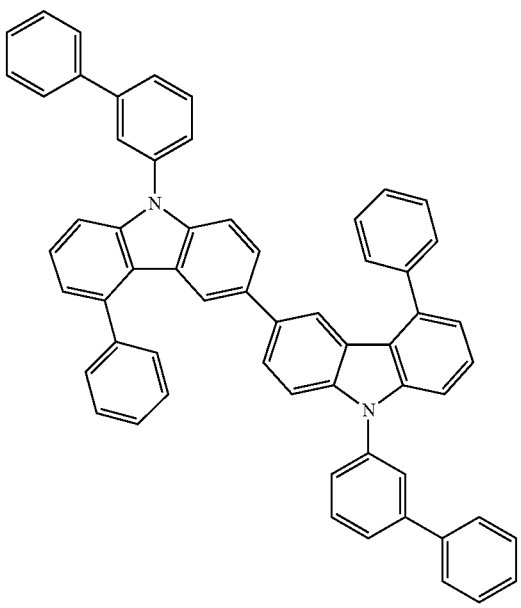
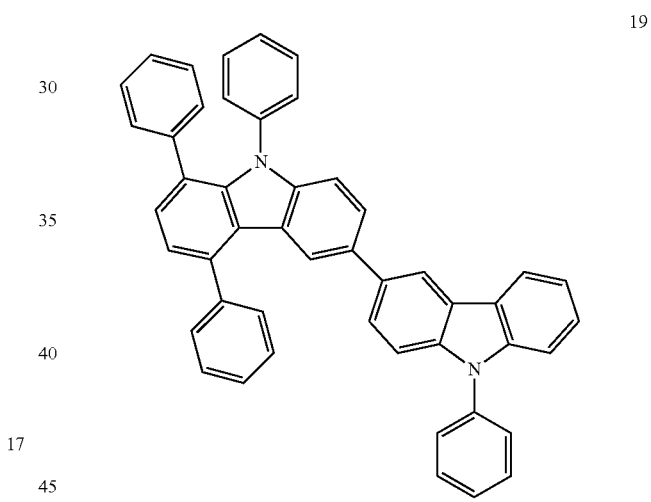
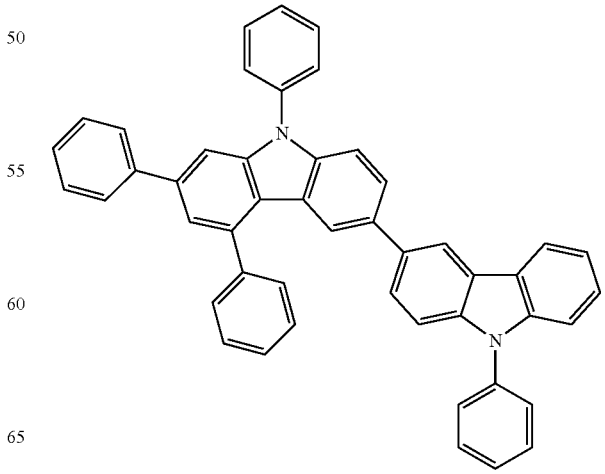

21
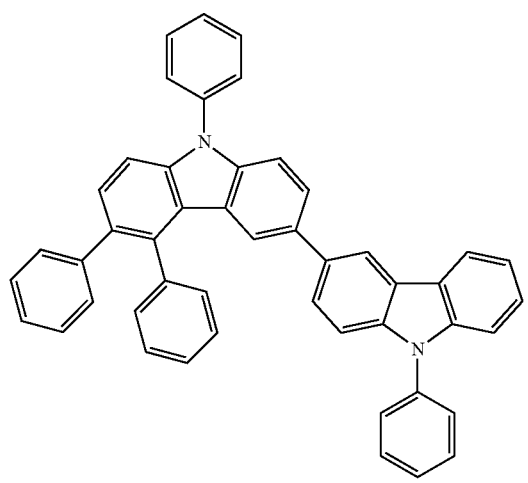
22
24
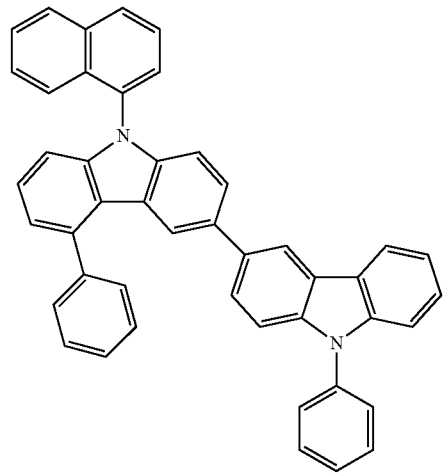
25
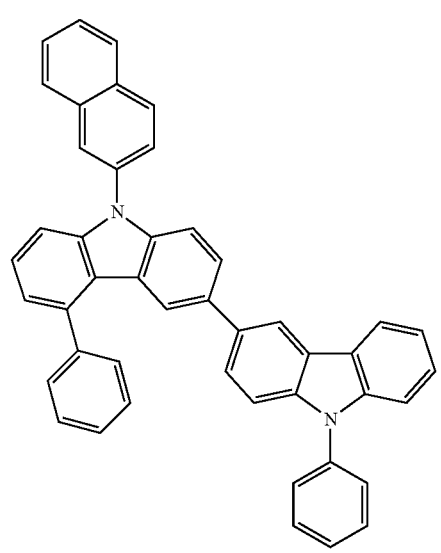
23
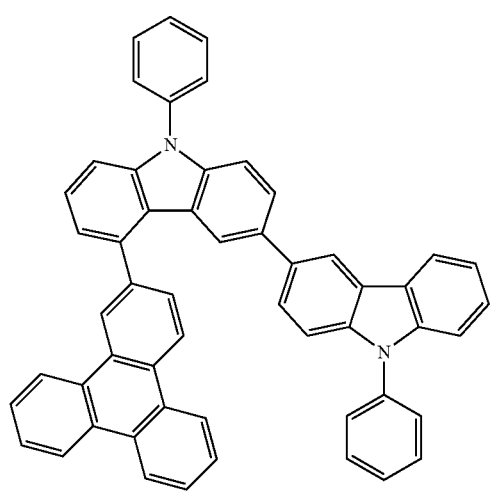
26
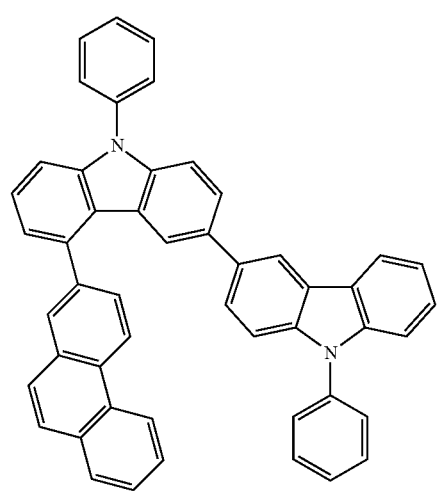

27
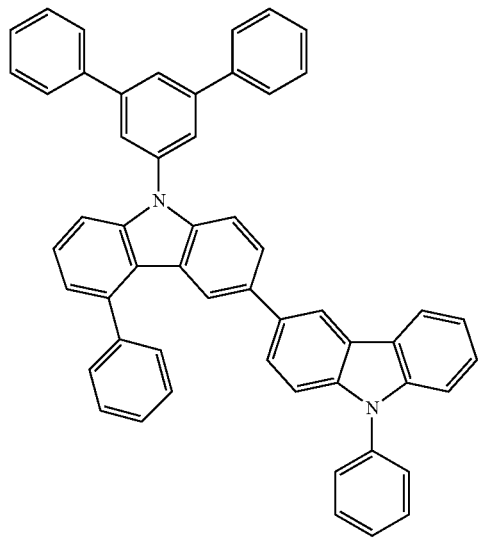
28
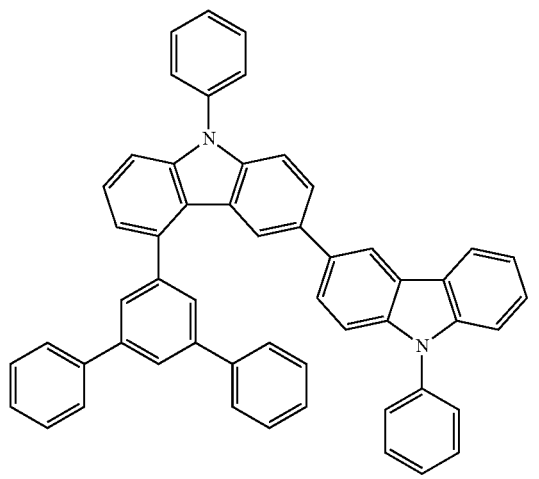
30
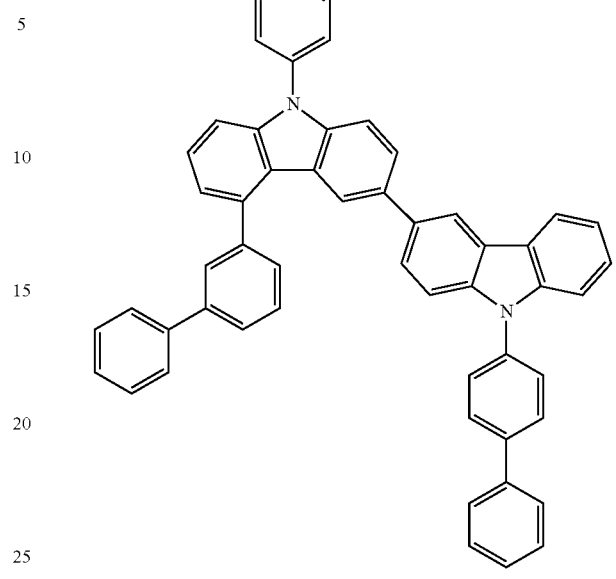
31
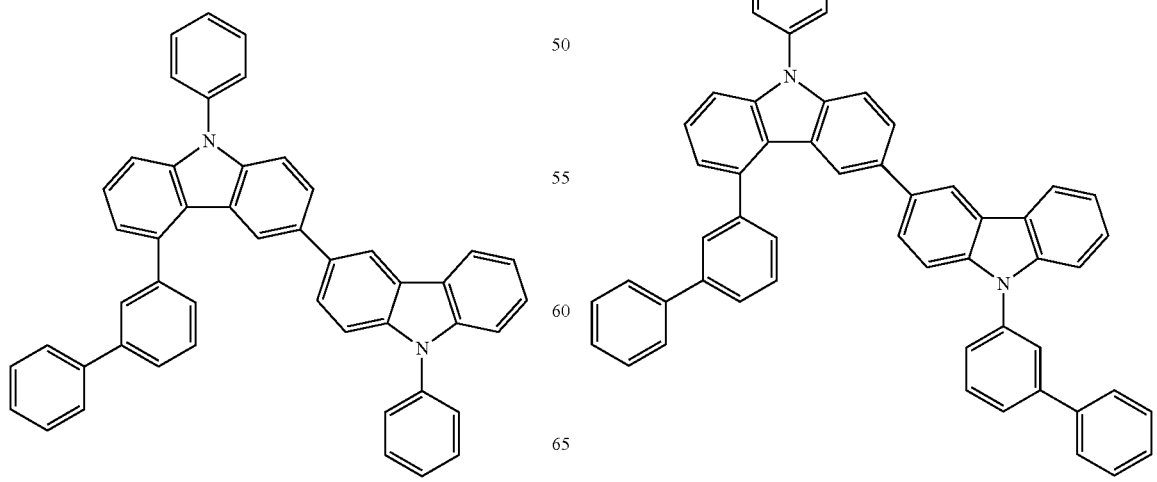

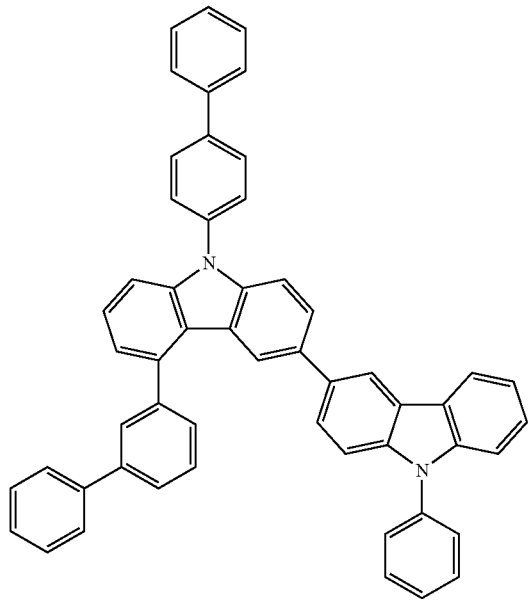
32
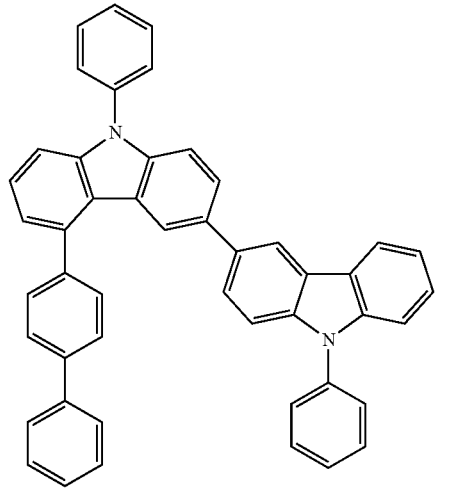
34
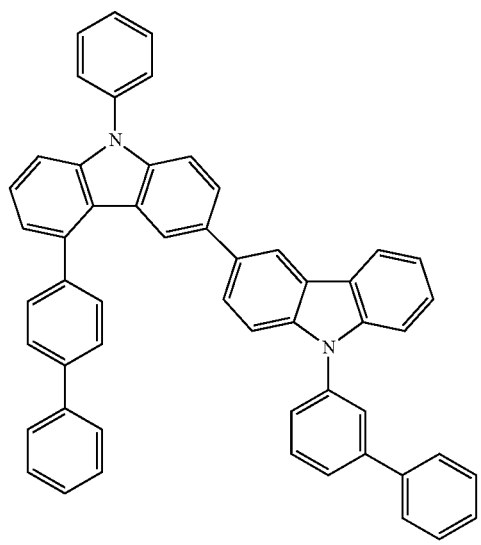
35
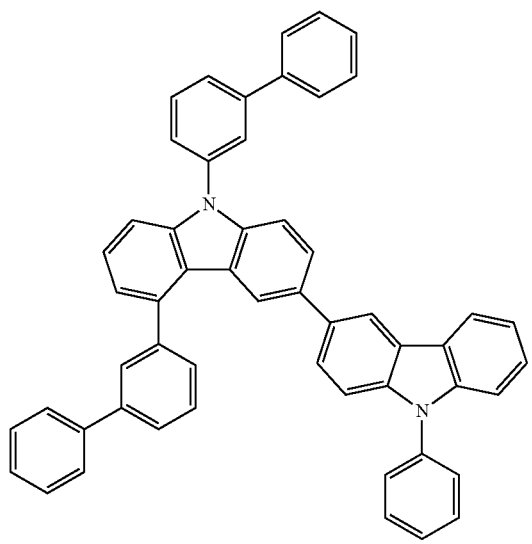
33
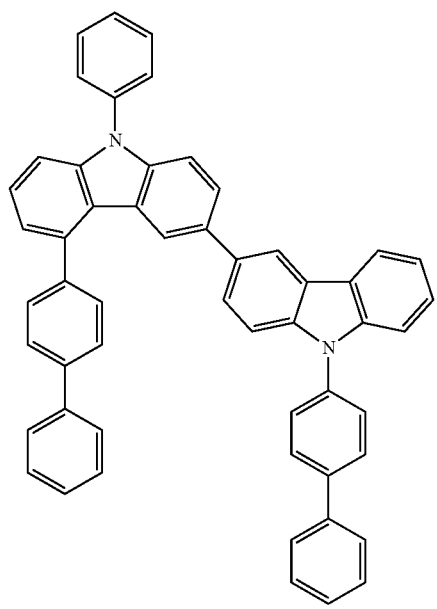
36

37
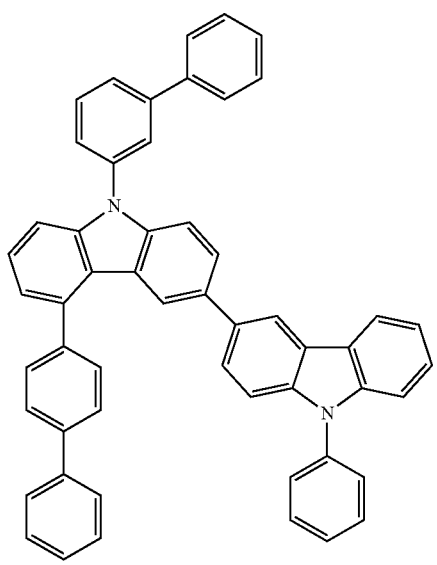
38
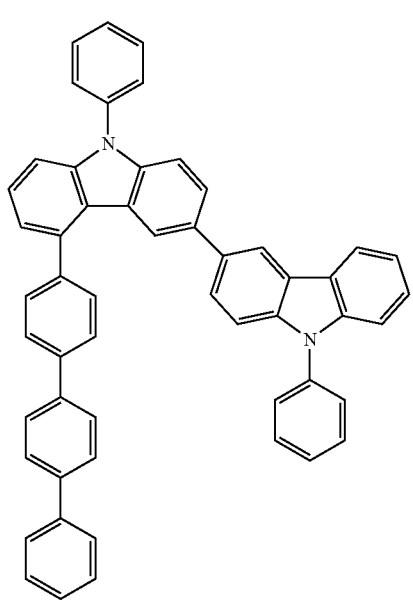
39
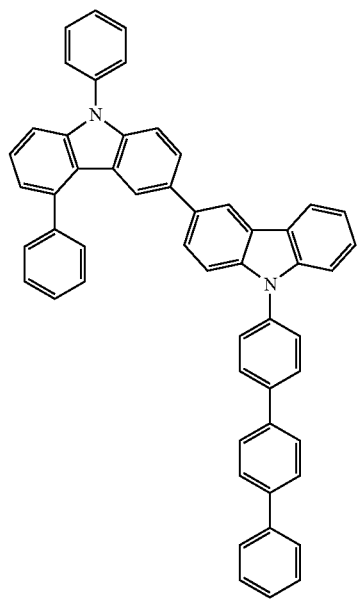
40
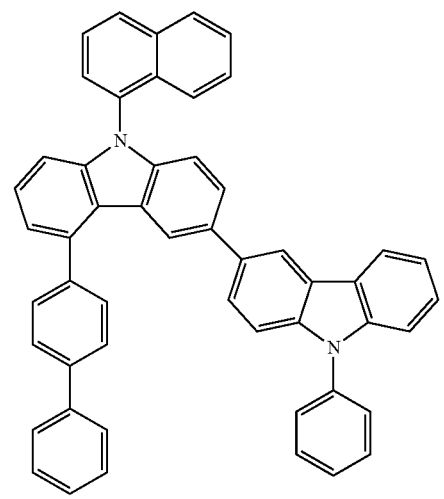
41
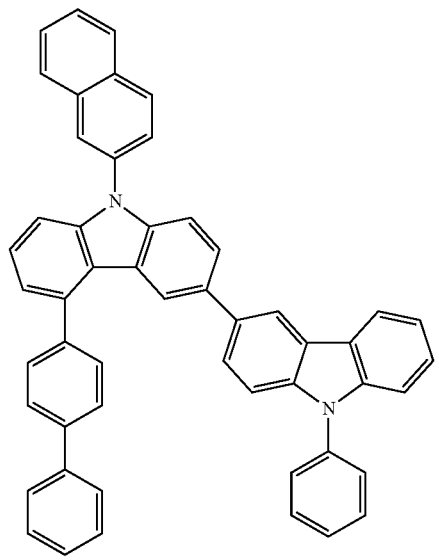

42
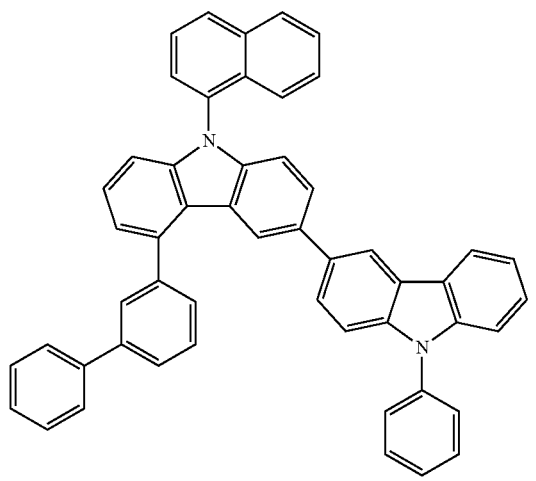
43
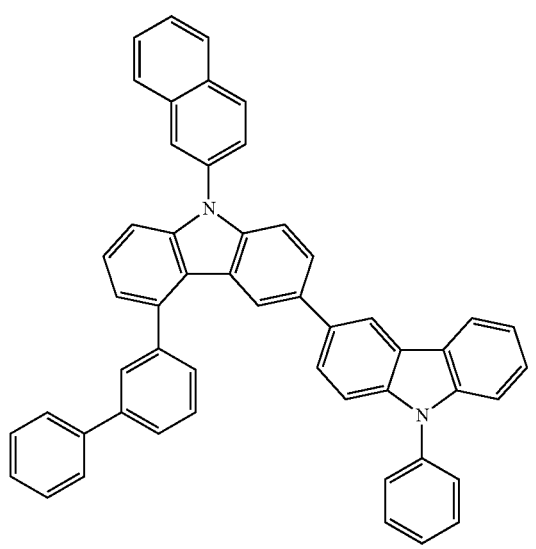
44
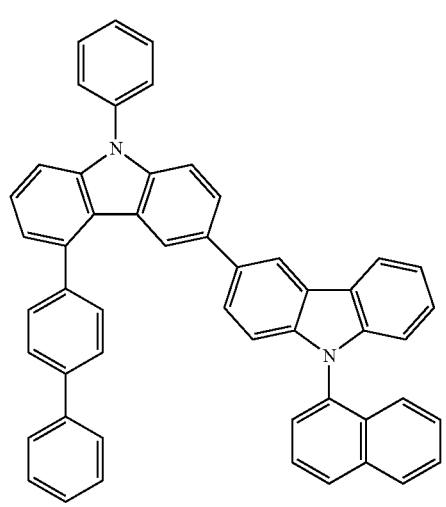
45
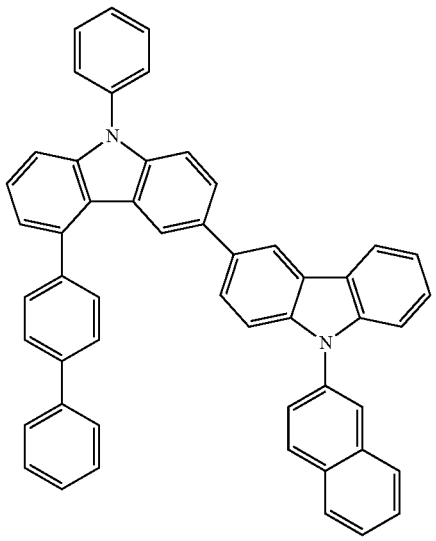
46
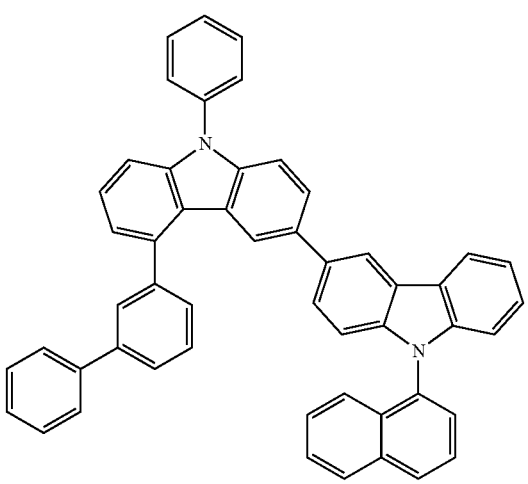
47
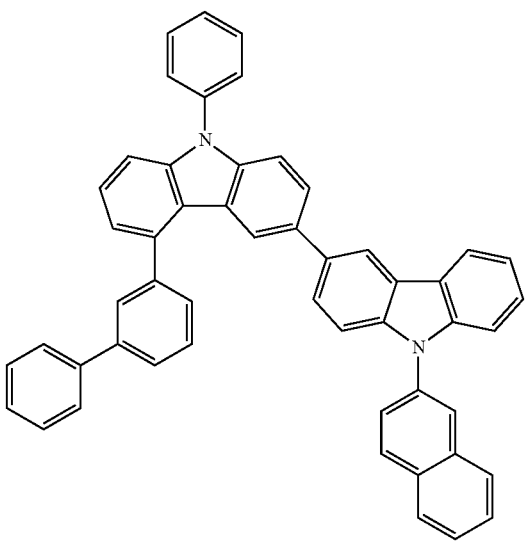

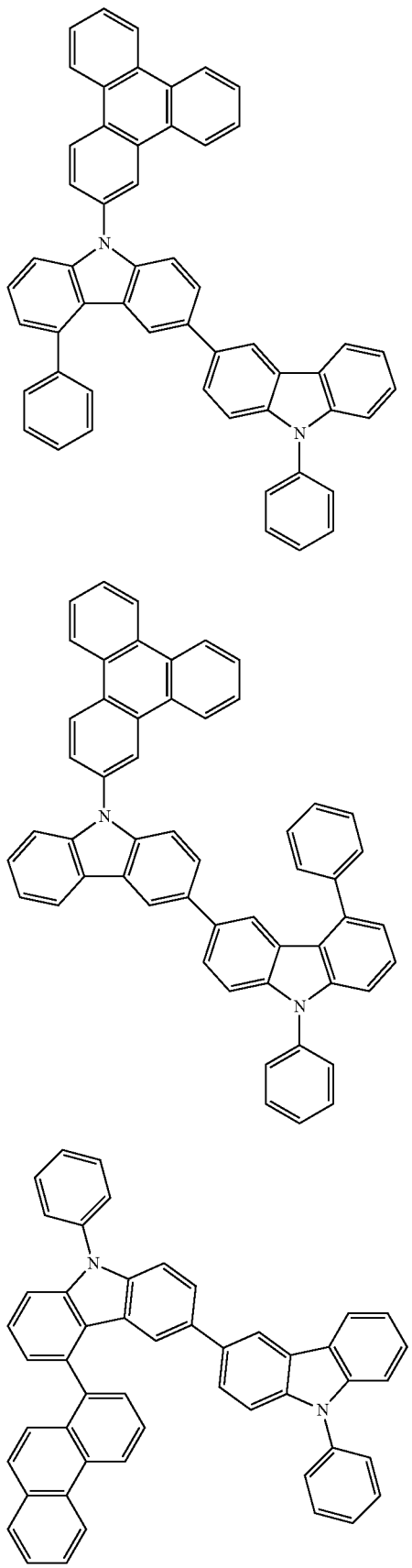
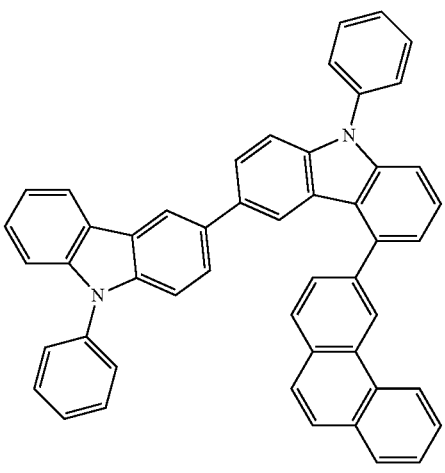
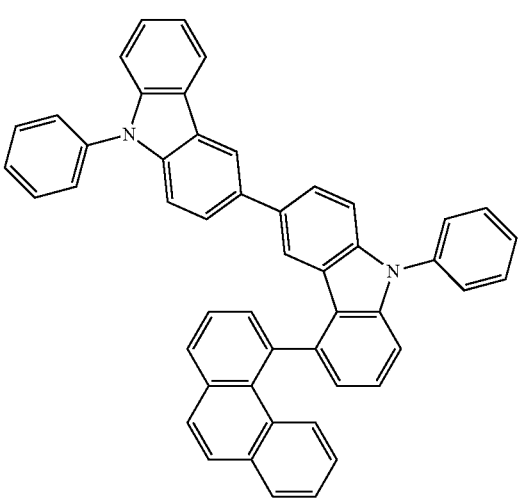
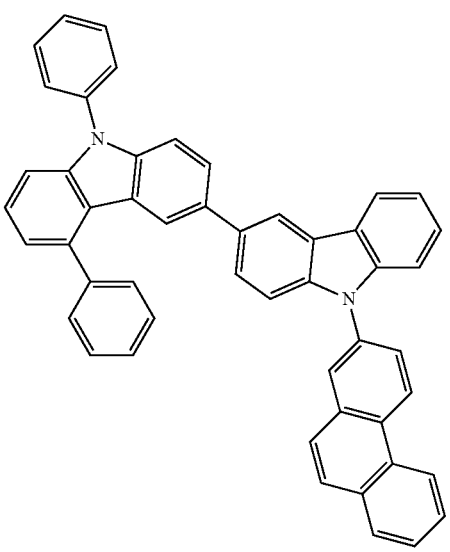

54

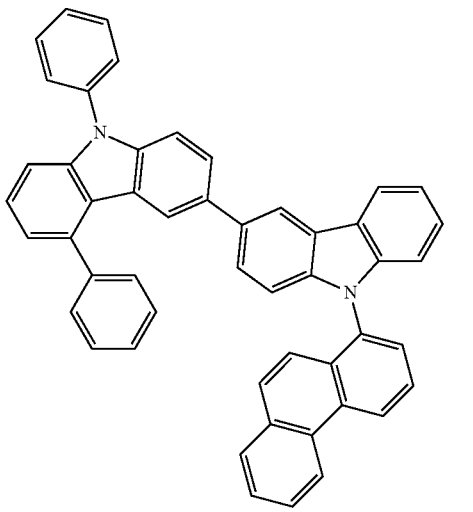

55

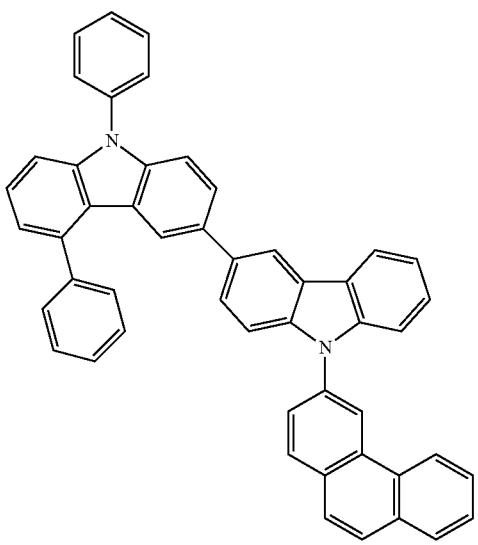

56

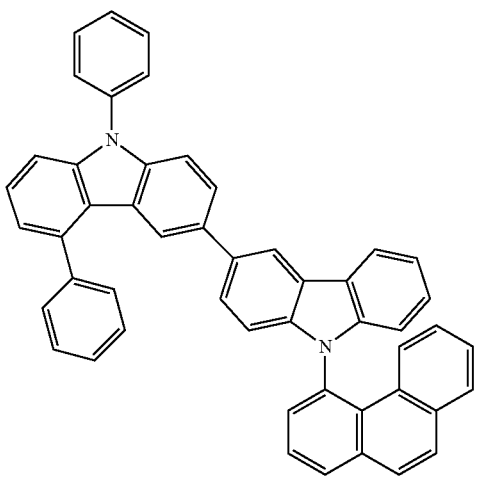

The first compound for an organic optoelectric device may be applied to an organic optoelectric device and may be applied in an organic optoelectric device alone or with other compounds for an organic optoelectric device. When the compound for an organic optoelectric device applied with other compounds for an organic optoelectric device, it may be applied in a form of a composition.

Hereinafter, one example of a composition for an organic optoelectric device including the first compound for an organic optoelectric device is described.

The composition for an organic optoelectric device according to another embodiment includes the first compound for an organic optoelectric device and a second compound for an organic optoelectric device represented by Chemical Formula 2.

[Chemical Formula 2]

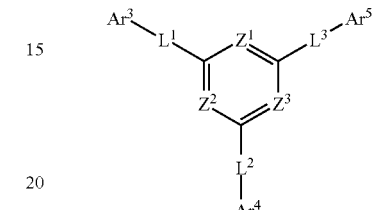

In Chemical Formula 2,
$Z^1$ to $Z^3$ are independently N or $CR^a$,
at least two of $Z^1$ to $Z^3$ are N,
$R^a$'s are independently hydrogen, deuterium, a substituted or unsubstituted C1 to C10 alkyl group, a substituted or unsubstituted C6 to C30 aryl group or a substituted or unsubstituted C2 to C30 heterocyclic group,
$R^a$'s are independently present or adjacent groups are linked with each other to provide a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring,
$Ar^3$ to $Ar^5$ are independently a substituted or unsubstituted C6 to C30 aryl group, a substituted or unsubstituted C2 to C30 heterocyclic group, or a combination thereof,
$L^1$ to $L^3$ are independently a single bond, a substituted or unsubstituted C6 to C30 arylene group, a substituted or unsubstituted C2 to C30 heteroarylene group, or a combination thereof, and
the "substituted" refers to replacement of at least one hydrogen by deuterium, a C1 to C4 alkyl group, a C6 to C18 aryl group, or a C2 to C18 heteroaryl group.

Specifically, Chemical Formula 2 may be represented by one of Chemical Formula 2-1, Chemical Formula 2-2, and Chemical Formula 2-3.

[Chemical Formula 2-1]

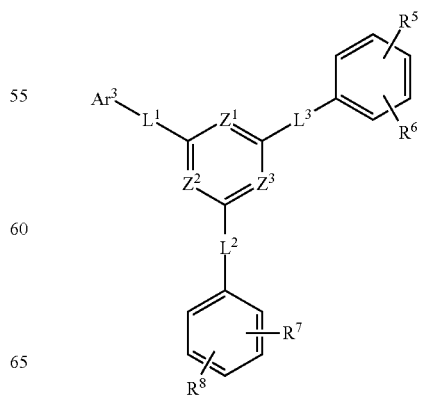

[Chemical Formula 2-2]

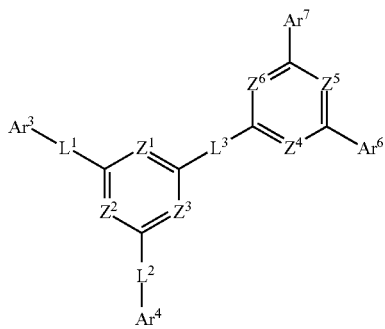

[Chemical Formula 2-3]

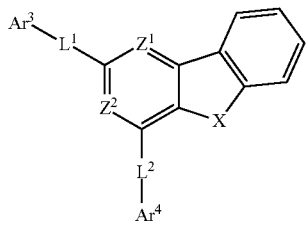

In Chemical Formulae 2-1 to 2-3, $Z^1$ to $Z^3$, $Ar^3$ to $Ar^5$, and $L^1$ to $L^3$ are the same as described above, $Z^4$ to $Z^6$ are the same as definitions of $Z^1$ to $Z^3$, $Ar^6$ and $Ar^7$ are the same as definitions of $Ar^3$ to $Ar^5$, and X is O or S.

In an example embodiment, Chemical Formula 2 may be represented by Chemical Formula 2-1 or Chemical Formula 2-3.

In a specific example embodiment, $Ar^3$ to $Ar^5$ of Chemical Formula 2 may independently be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted phenanthrene group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted indolocarbazolyl group, a substituted or unsubstituted indolobenzofuranyl group, a substituted or unsubstituted indolobenzothiophenyl group, a substituted or unsubstituted benzofuranpyrimidinyl group, or a substituted or unsubstituted benzothiophenepyrimidinyl group.

Specifically, $Ar^3$ to $Ar^5$ of Chemical Formula 2-1 to Chemical Formula 2-3 may independently be a substituted or unsubstituted phenyl group, a substituted or unsubstituted biphenyl group, a substituted or unsubstituted triphenylene group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted benzofuranpyrimidinyl group, or a substituted or unsubstituted benzothiophenepyrimidinyl group, $Ar^6$ and $Ar^7$ are independently substituted or unsubstituted phenyl group, or a substituted or unsubstituted biphenyl group, $R^a$ and $R^5$ to $R^8$ may independently be hydrogen, or a phenyl group, $L^1$ to $L^3$ may independently be a single bond, a substituted or unsubstituted phenylene group, a substituted or unsubstituted biphenylene group, or a substituted or unsubstituted terphenylene group.

For example, $L^1$ to $L^3$ may be a single bond or may be selected from linking groups of Group II.

[Group II]

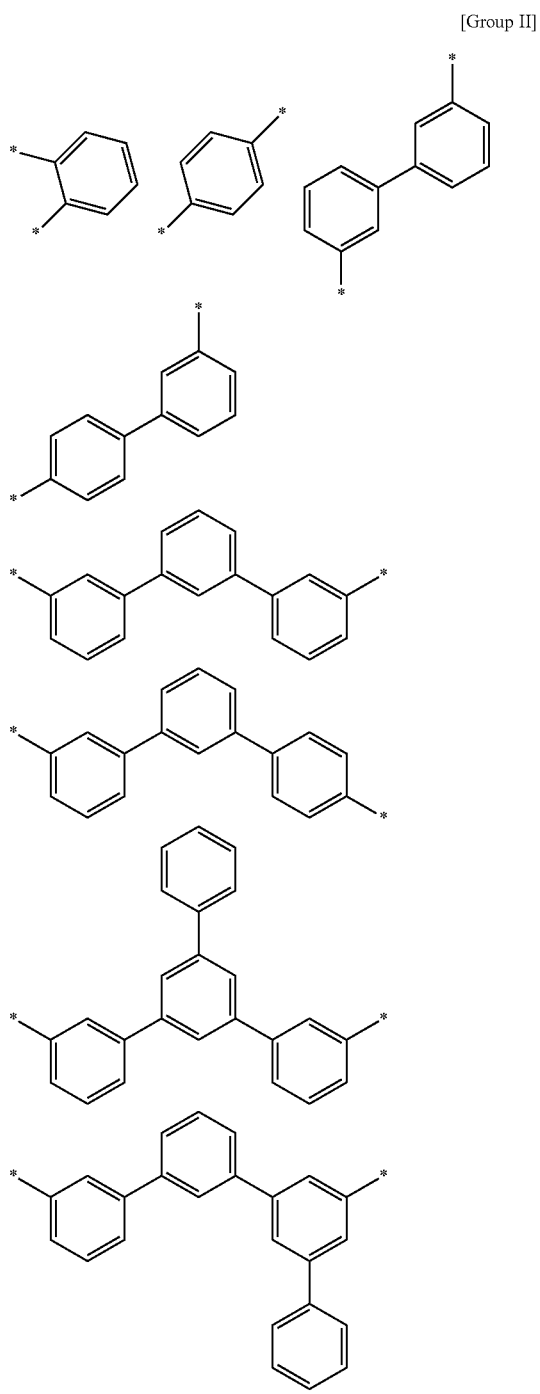

The second compound for an organic optoelectric device represented by Chemical Formula 2 may be for example compounds of Group 2, but is not limited thereto.

[Group 2]
A-1
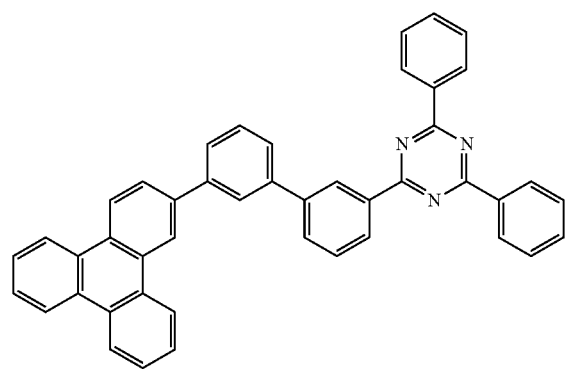
A-2
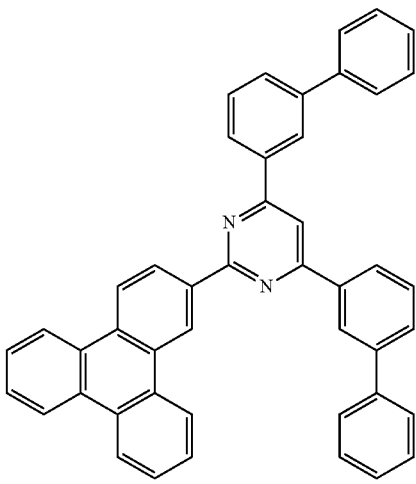
A-3
A-4
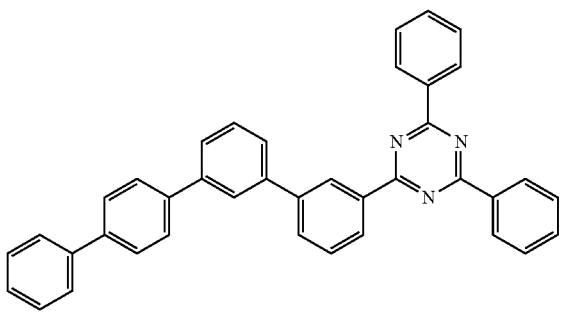
A-5
A-6
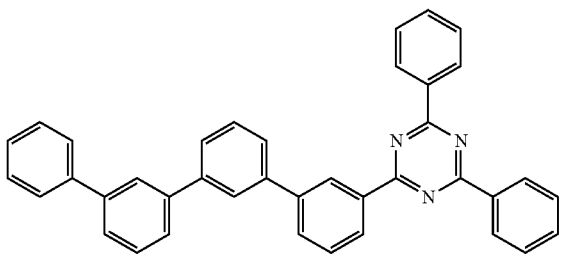
A-7
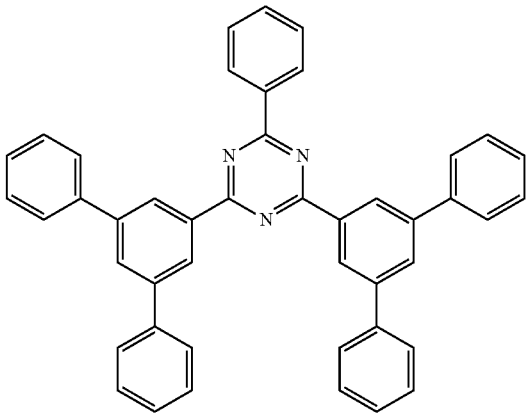

A-8
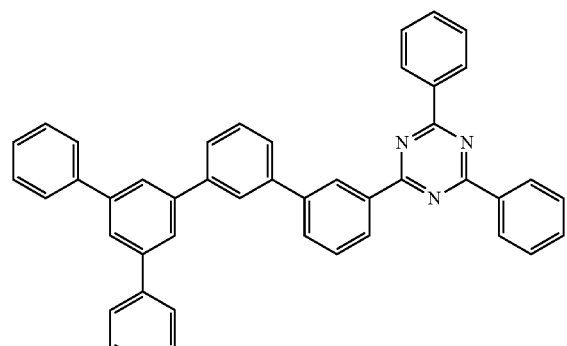
A-9
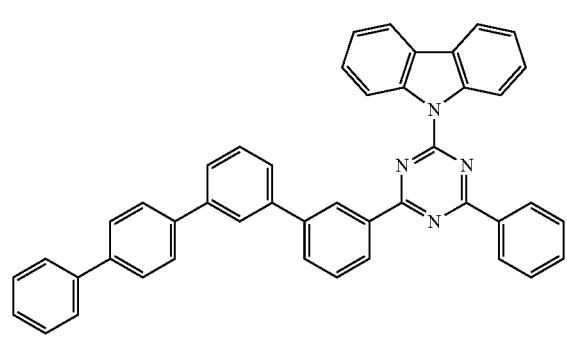
A-10
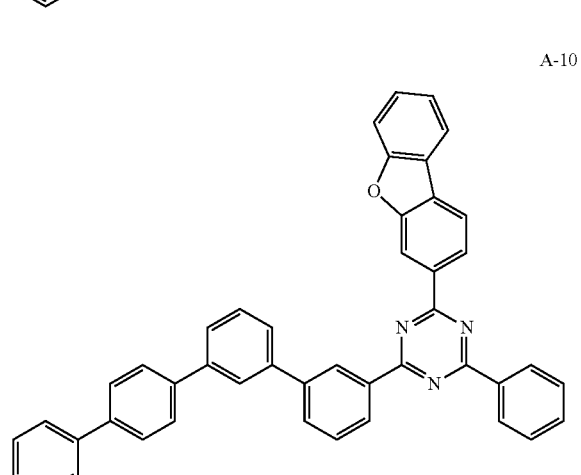
A-11
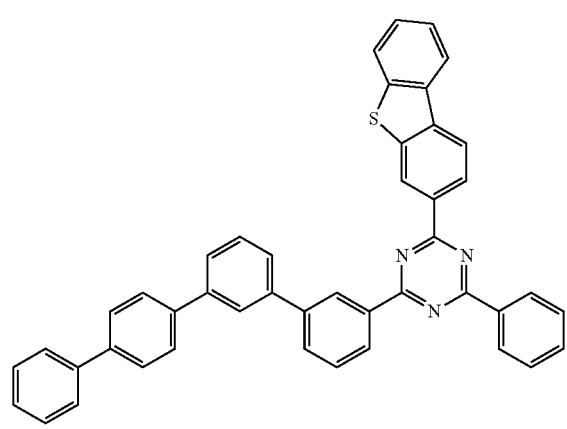
A-12
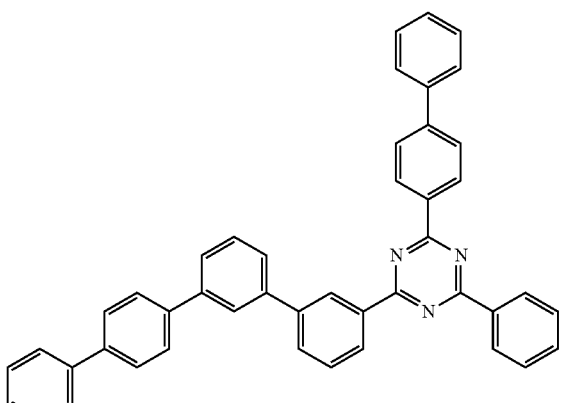
A-13
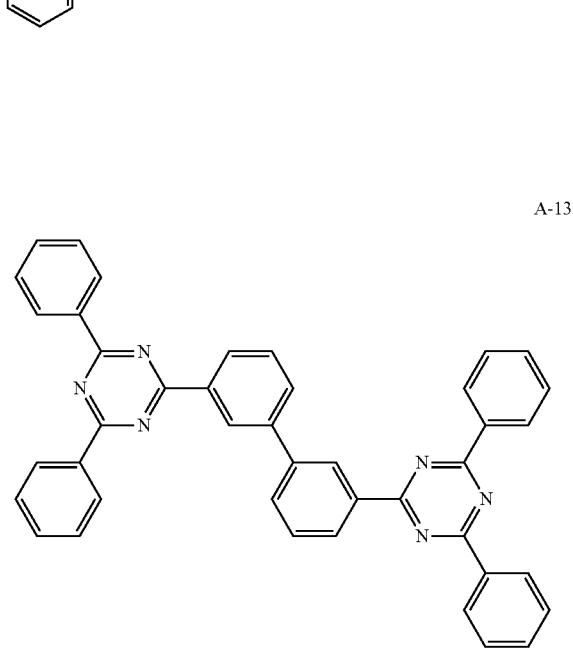
A-14
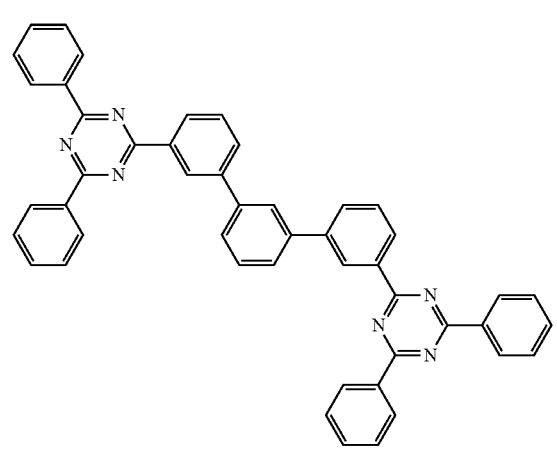

-continued
A-15
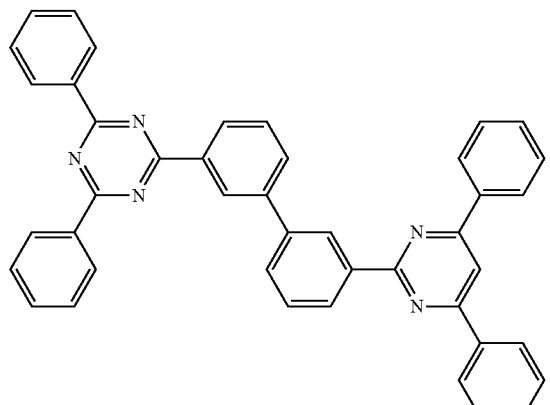
A-16
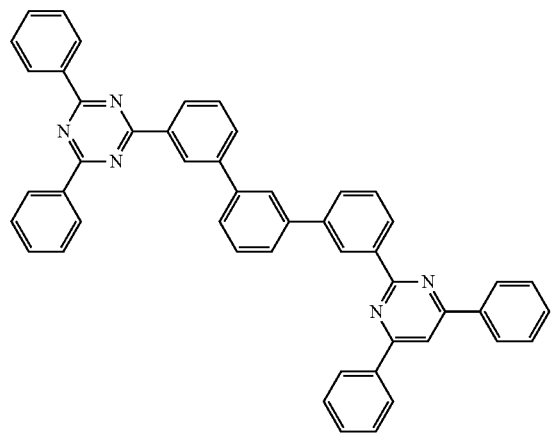
A-17
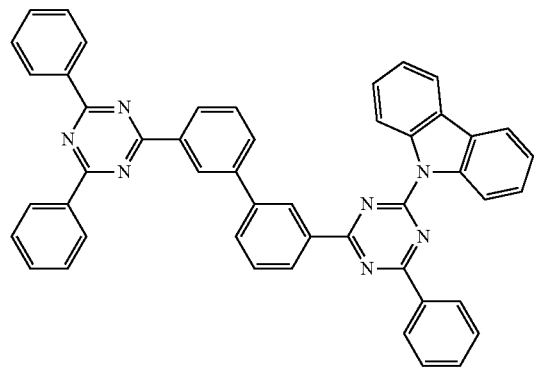
-continued
A-18
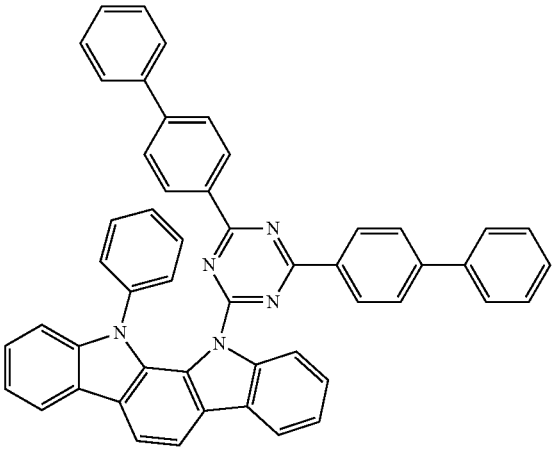
A-19
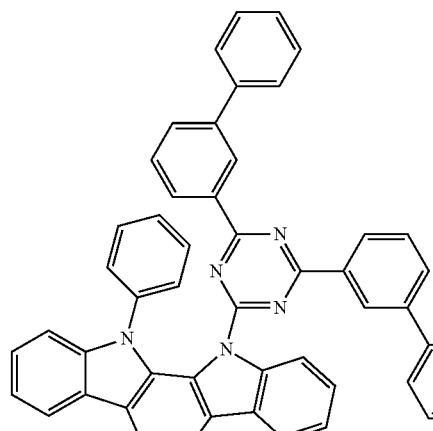
A-20
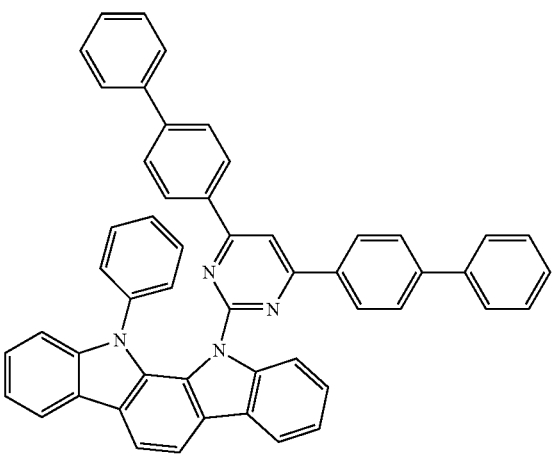

A-21
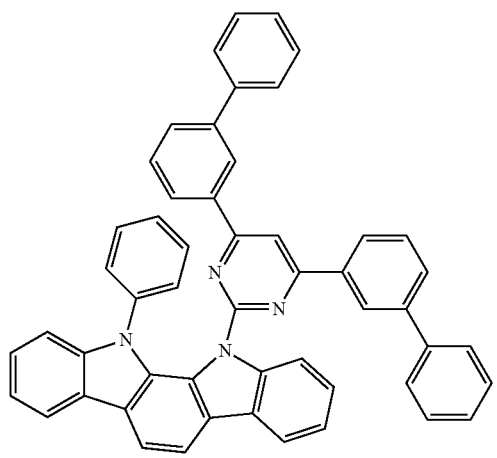
A-22
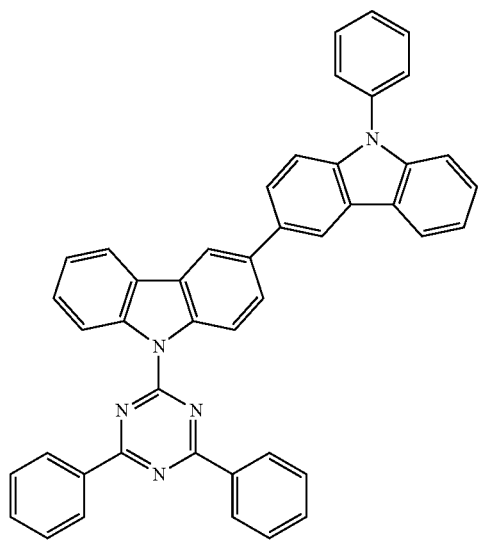
A-23
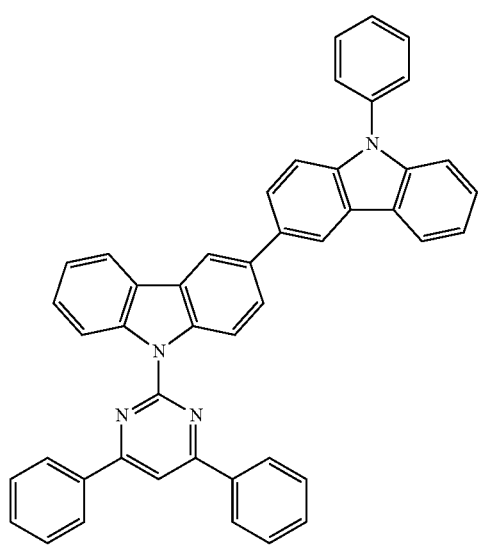
A-24
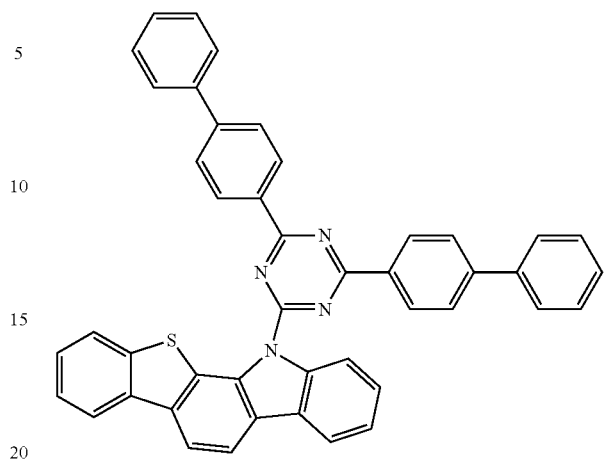
A-25
A-26
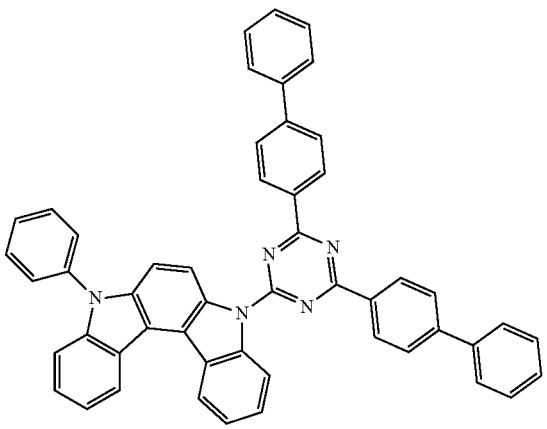

A-27
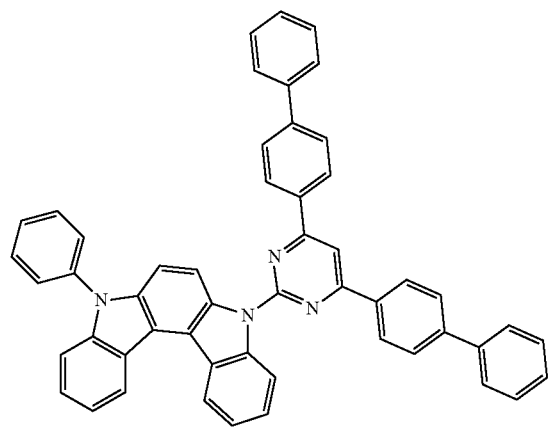
A-30
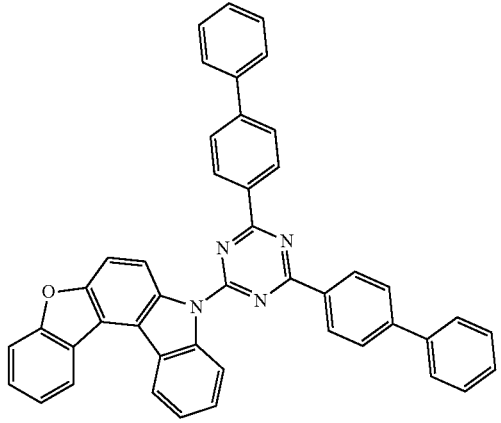
A-28
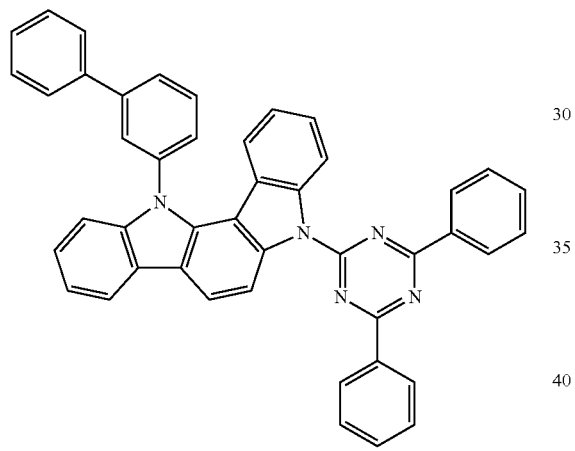
A-31
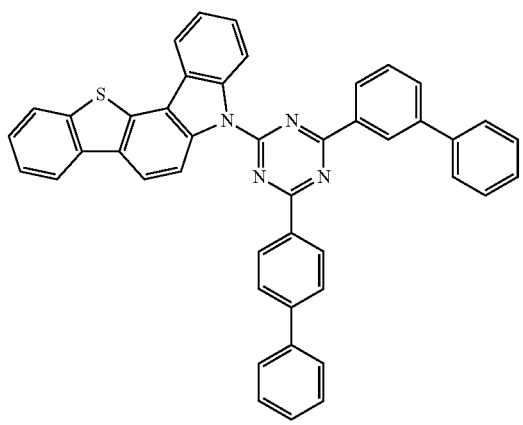
A-29
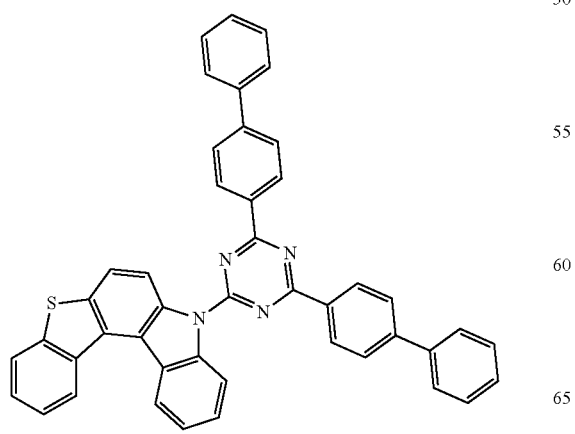
A-32
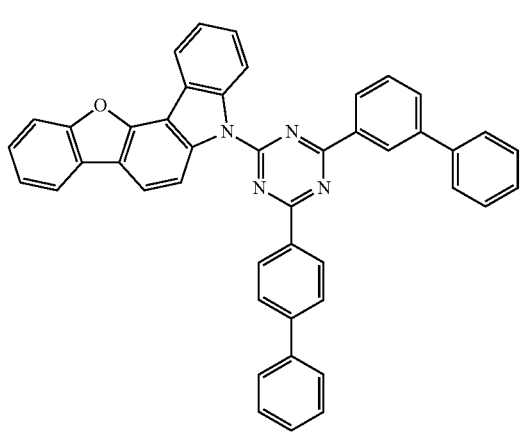

-continued
b-1
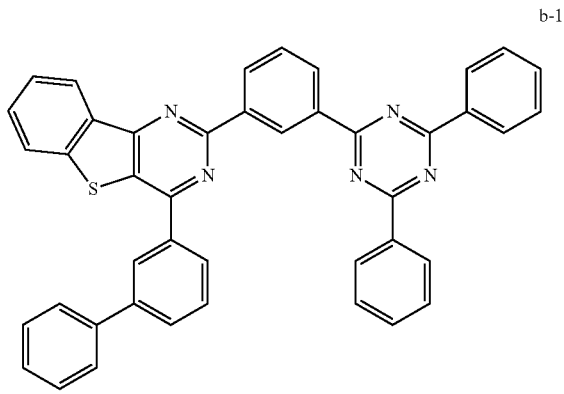
b-2
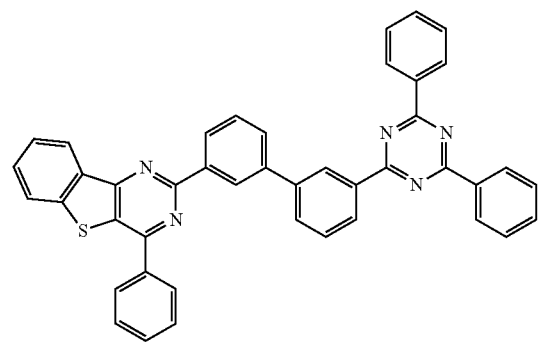
b-3
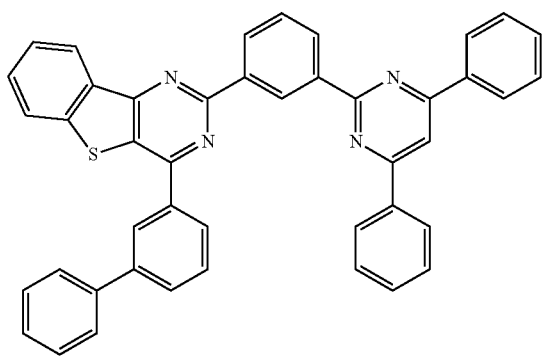
b-4
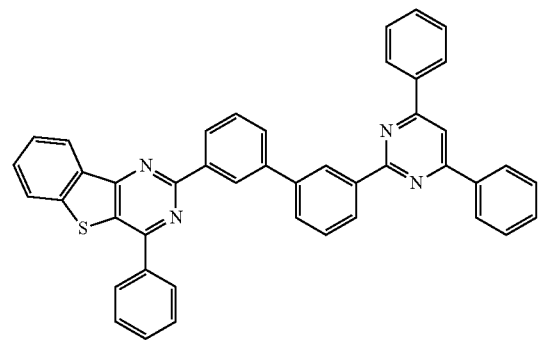
b-5
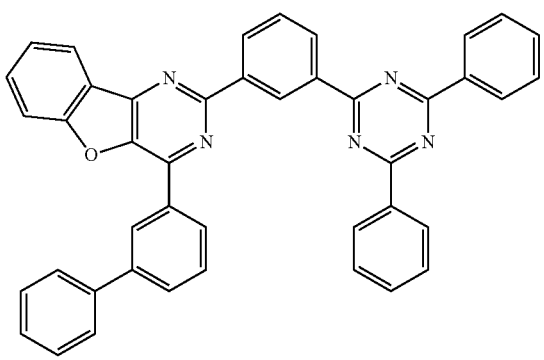
b-6
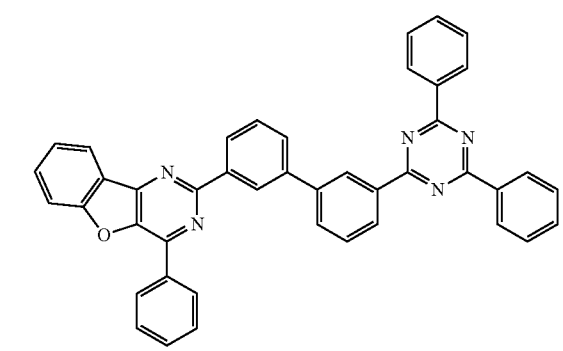
b-7
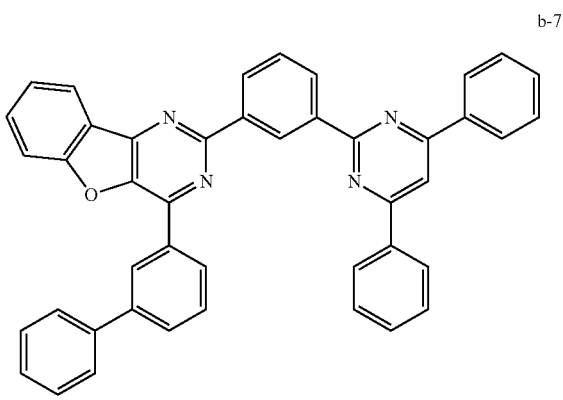
b-8
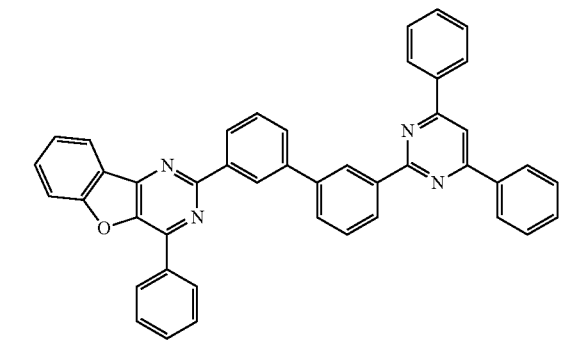

b-9
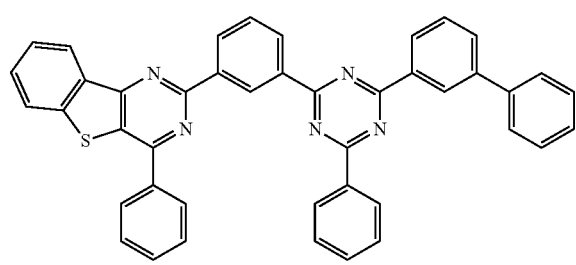
b-13
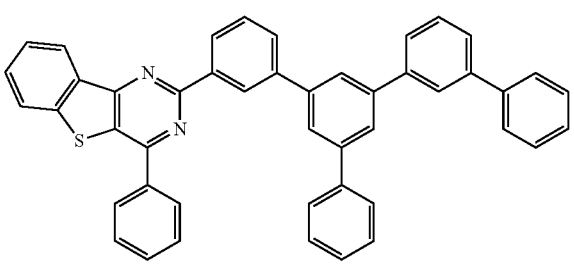
b-10
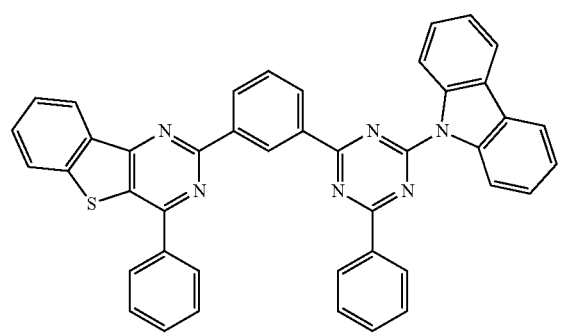
b-14
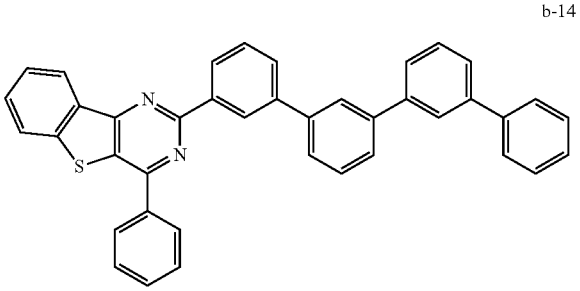
b-11
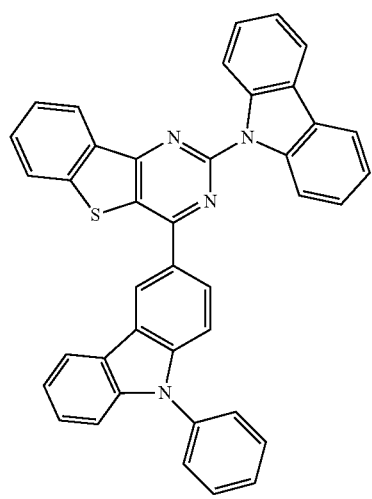
b-15
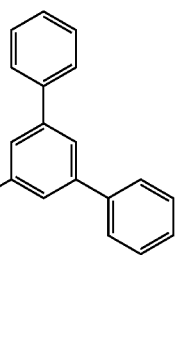
b-12
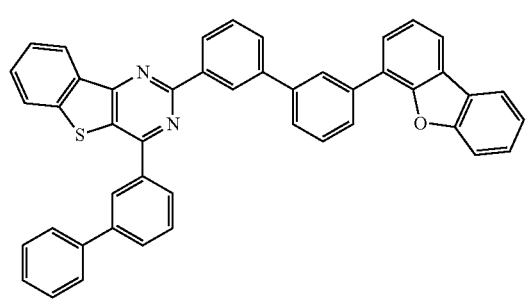
b-16
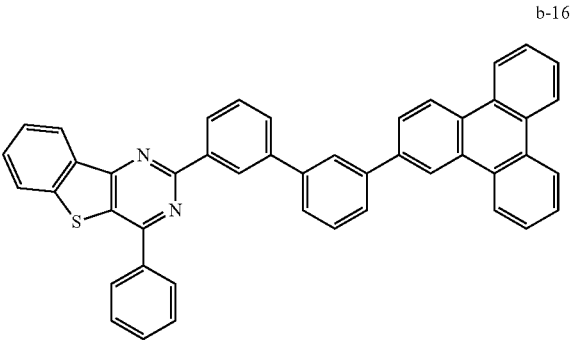

-continued
b-17
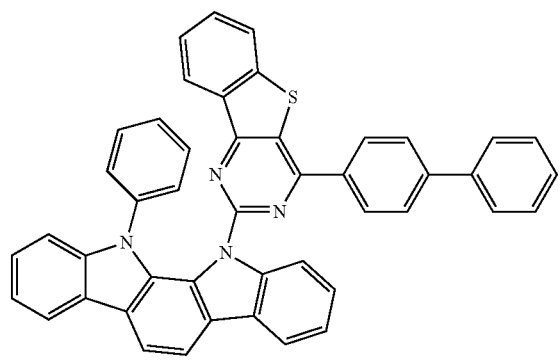
b-18
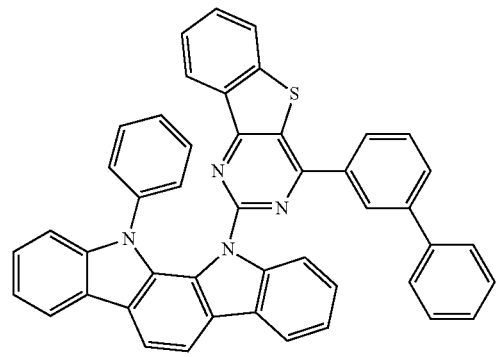
b-19
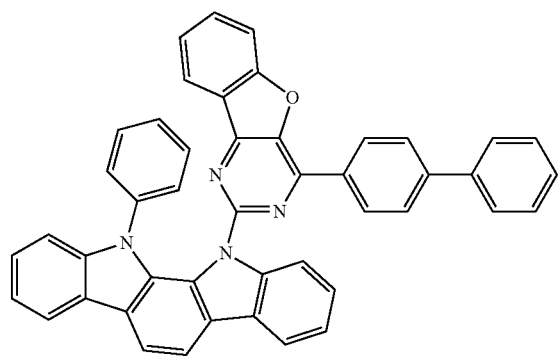
b-20
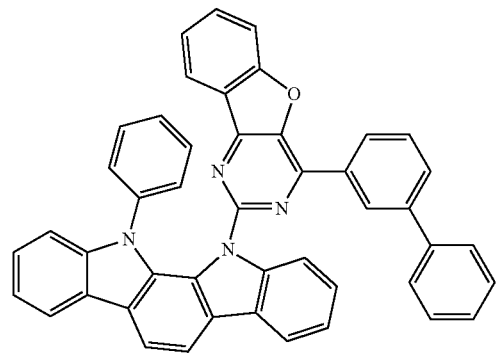
-continued
b-21
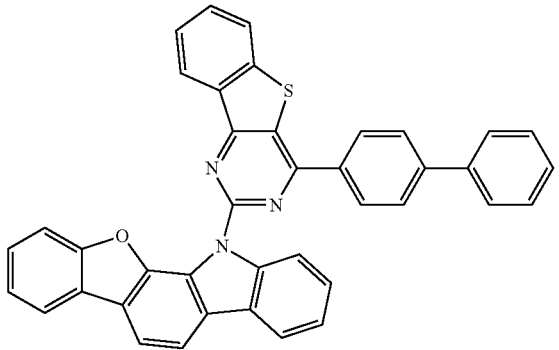
b-22
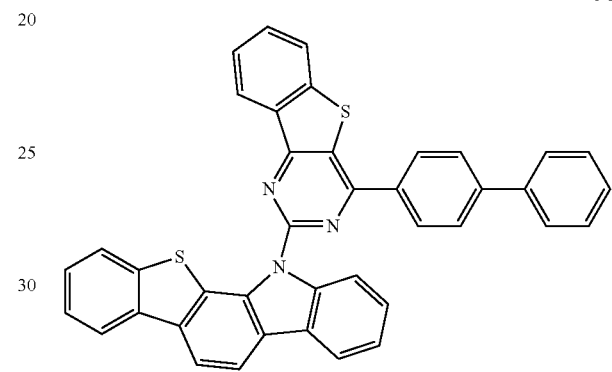
b-23
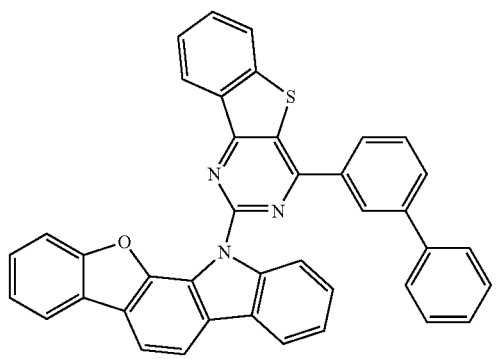
b-24
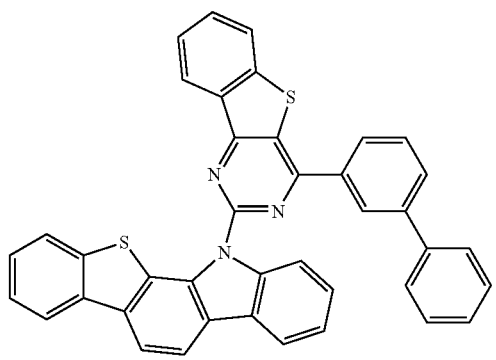

-continued b-25
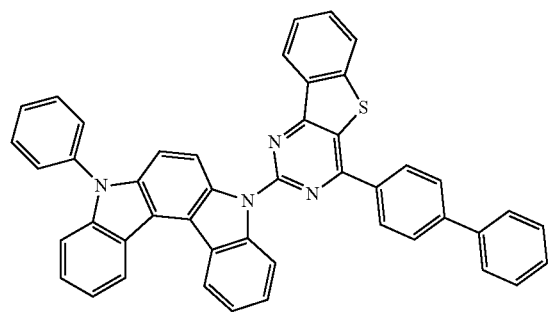

b-26
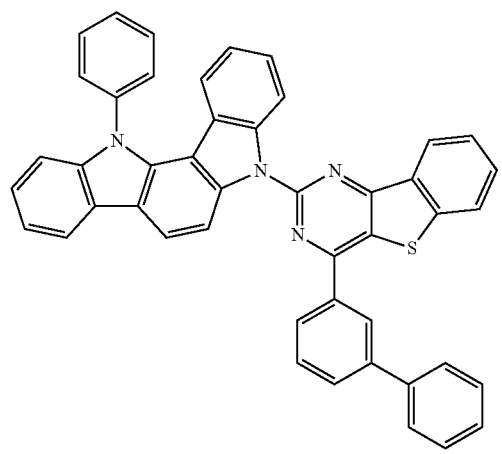

b-27
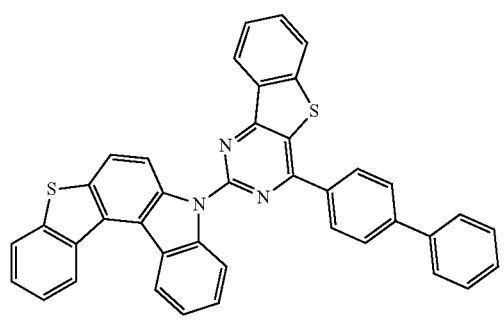

b-28
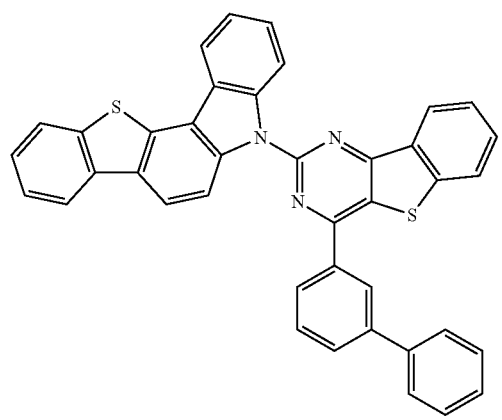

-continued b-29
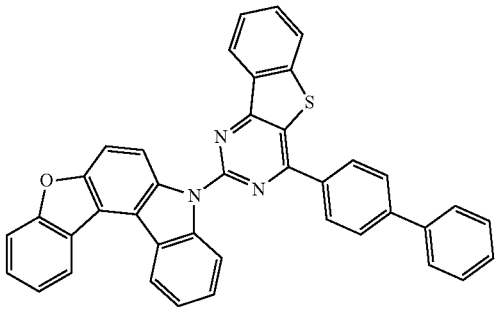

b-30
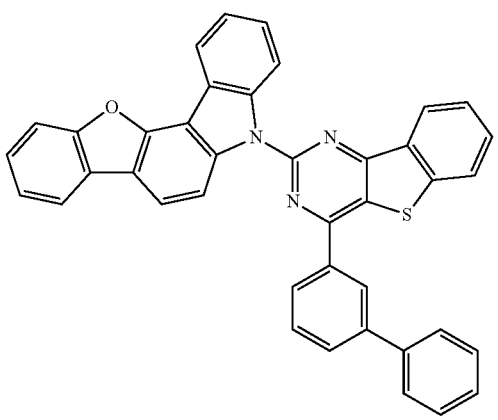

b-31
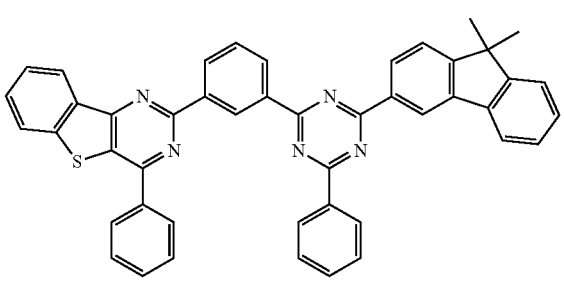

b-32
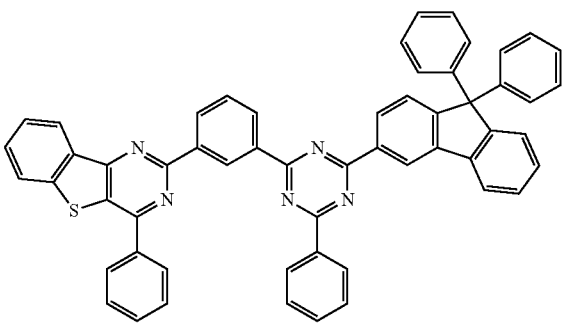

The second compound for an organic optoelectric device is used with the first compound for an organic optoelectric device in the light emitting layer and increases charge mobility and stability, and thereby luminous efficiency and life-span characteristics may be improved. In addition, a ratio of the second compound for an organic optoelectric device and the first compound for an organic optoelectric device may be adjusted and thereby charge mobility may be controlled.

In addition, the first compound for an organic optoelectric device and the second compound for an organic optoelectric device may be for example included in a weight ratio of about 1:9 to about 9:1, about 2:8 to about 8:2, about 3:7 to about 7:3, about 4:6 to about 6:4 and about 5:5, specifically about 1:9 to about 8:2, about 1:9 to about 7:3, about 1:9 to about 6:4, or about 1:9 to about 5:5, and more specifically, about 2:8 to about 7:3, about 2:8 to about 6:4, or about 2:8 to about 5:5. In addition, they may be included in a weight ratio of about 3:7 to about 6:4 or about 3:7 to about 5:5, and more specifically about 5:5.

As one example of the composition for an organic optoelectric device, the first compound for an organic optoelectric device may be represented by Chemical Formula 1 and the second compound for an organic optoelectric device may be represented by Chemical Formula 2-1 or Chemical Formula 2-3.

The composition may further include one or more organic compounds in addition to the first compound for an organic optoelectric device and the second compound for an organic optoelectric device.

The compound for an organic optoelectric device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectric device including the compound for an organic optoelectric device or the composition for an organic optoelectric device is described.

An organic optoelectric device according to another embodiment includes an anode and a cathode facing each other and at least one organic layer disposed between the anode and the cathode, wherein the organic layer includes the compound for an organic optoelectric device or the composition for an organic optoelectric device.

For example, the organic layer may include a light emitting layer and the light emitting layer may include the compound for an organic optoelectric device or the composition for an organic optoelectric device of the present disclosure.

Specifically, the compound for an organic optoelectric device or the composition for an organic optoelectric device may be included as a host, for example a green host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectric device or the composition for an organic optoelectric device.

The organic layer may further include a hole auxiliary layer that is adjacent to the light emitting layer and the hole auxiliary layer may include the compound for an organic optoelectric device or the composition for an organic optoelectric device.

The organic optoelectric device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectric device is described referring to drawings.

Figure 2:
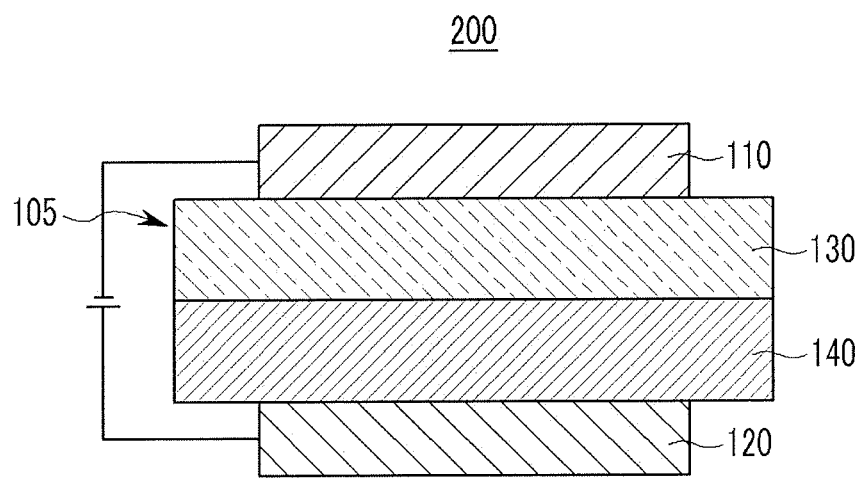

FIGS. 1 and 2 are cross-sectional views of an organic light emitting diode according to embodiments.

Referring to FIG. 1, an organic light emitting diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal such as nickel, platinum, vanadium, chromium, copper, zinc, gold, and the like, or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDT), polypyrrole, and polyaniline, but is not limited thereto.

The cathode 110 may be made of a conductor having a small work function to help electron injection, and may be for example made of a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, $LiO_2$/Al, LiF/Ca, LiF/Al and $BaF_2$/Ca, but is not limited thereto.

The organic layer 105 includes a light emitting layer 130 including the compound or the composition for an organic optoelectric device.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound or the composition for an organic optoelectric device of the present disclosure may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co. Ltd. or TCI Inc. as far as there in no particular comment or were synthesized by known methods.

(Preparation of Compound for Organic Optoelectric Device)

The compound as one specific examples of the present disclosure was synthesized through the following steps.

(First Compound for Organic Optoelectric Device)

SYNTHESIS EXAMPLE 1

Synthesis of Compound 2

[Reaction Scheme 1]

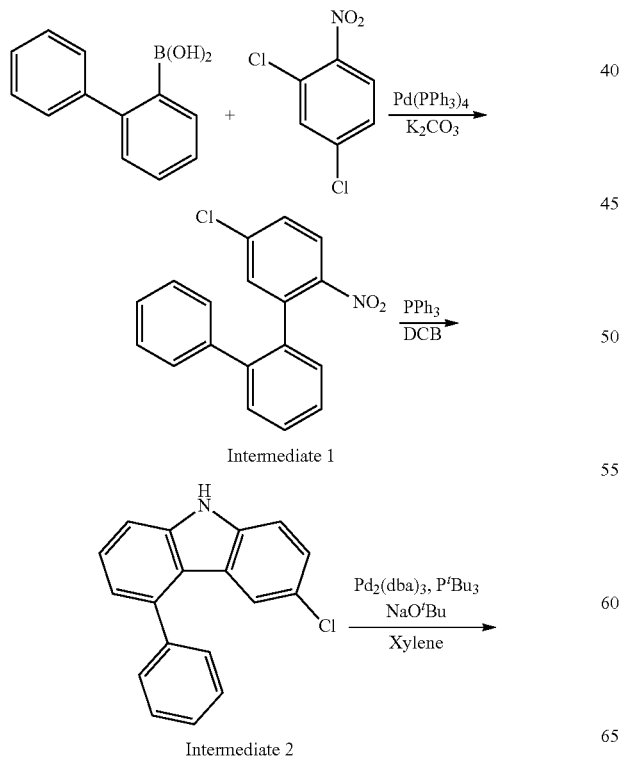

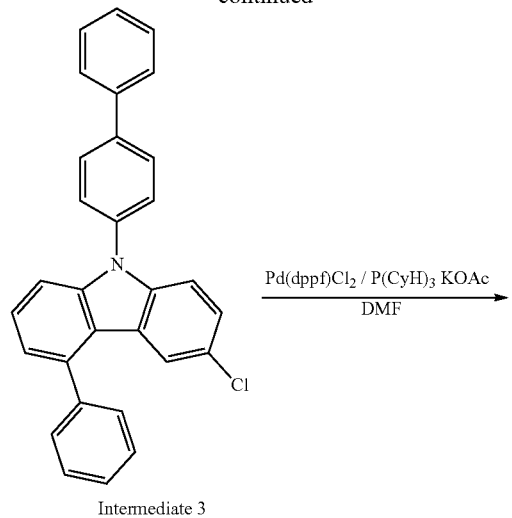

Intermediate 3

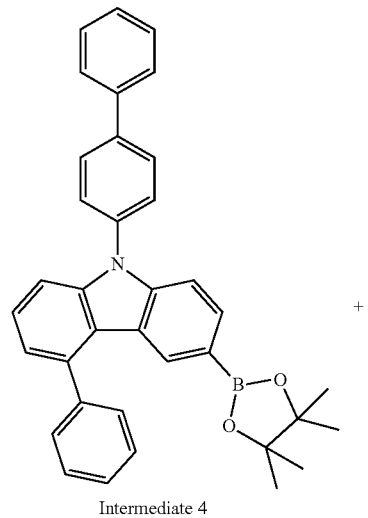

Intermediate 4

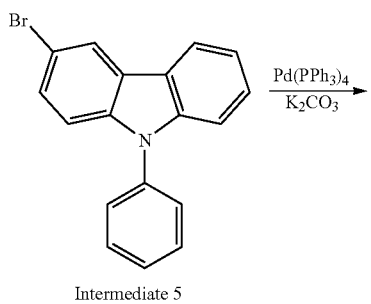

Intermediate 5

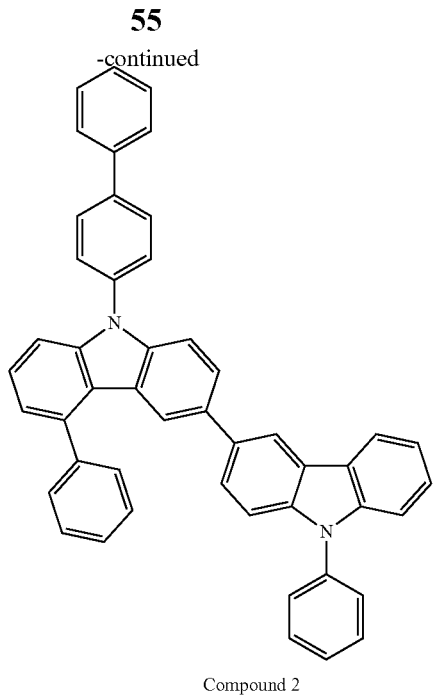

Compound 2

First Step: Synthesis of Intermediate 1

100.0 g (0.505 mol) of biphenyl-2-boronic acid, 101.22 g (0.53 mol) of 2,4-dichloro-1-nitro-benzene, 174.4 g (1.26 mol) of potassium carbonate, and 17.5 g (15.14 mmol) of tetrakis(triphenylphosphine) palladium (0) were added to 1.6 L of 1,4-dioxane and 0.8 L of water in a 5 L flask, and the mixture was heated under a nitrogen flow for 12 hours at 80° C. When a reaction was complete, a mixture obtained by removing an organic layer therefrom was added to 2 L of methanol, and a solid crystallized therein was filtered, dissolved in toluene, filtered with silica gel/Celite, and after removing an organic solvent in an appropriate amount, recrystallized with methanol to obtain Intermediate 1 (121 g, a yield of 78%).

Second Step: Synthesis of Intermediate 2

Intermediate 1 (120.0 g, 0.39 mol) and triphenylphosphine (407 g, 1.553 mol) were put in a 3 L flask, 1.5 L of dichlorobenzene was added thereto for a nitrogen substitution, and the obtained mixture was stirred for 12 hours at 160° C. When a reaction was complete, silica gel was added thereto to volatilize a filtrate therein. The resultant was treated through column chromatography to obtain Intermediate 2 (48.41 g, a yield of 45%).

Third Step: Synthesis of Intermediate 3

24.0 g (86.6 mmol) of Intermediate 2, 24.2 g (103.9 mmol) of 4-bromoparabiphenyl, 16.65 g (173.2 mmol) of sodium t-butoxide, 4.98 g (8.7 mmol) of tris(dibenzylideneacetone) dipalladium, and 7.01 g of tri t-butylphosphine (50% in toluene) were mixed with 500 mL of xylene in a 1000 mL flask, and the mixture was heated and refluxed under a nitrogen flow for 15 hours. The obtained mixture was added to 1000 mL of methanol, and a solid crystallized therein was filtered, dissolved in monochlorobenzene, filtered with silica gel/Celite, and after removing an appropriate amount of an organic solvent, recrystallized with methanol to obtain Intermediate 3 (28.5 g, a yield of 77%).

Fourth Step: Synthesis of Intermediate 4

Intermediate 3 (28.0 g, 65.25 mmol), 4,4,4',4',5,5,5',5'-octamethyl-2,2'-bi(1,3,2-dioxaborolane) (19.88 g, 78.3 mmol), potassium acetate (KOAc, 19.21 g, 195.74 mmol), 1,1'-bis(diphenylphosphino) ferrocene-palladium(II) dichloride (3.2 g, 3.91 mmol), and tricyclohexylphosphine (5.49 g, 9.79 mmol) were added to 300 mL of N,N-dimethylformamide in a 1000 mL flask, and the mixture was stirred at 130° C. for 24 hours. When a reaction was complete, the reaction solution was extracted with water and EA, and an organic layer obtained therefrom was treated with magnesium sulfate to remove moisture, concentrated, and purified through column chromatography to obtain Intermediate 4 (25.6 g, a yield of 75%).

Fifth Step: Synthesis of Compound 2

4.0 g (7.67 mol) of Intermediate 4, 2.47 g (7.67 mol) of Intermediate 5, 2.65 g (19.18 mol) of potassium carbonate, and 0.27 g (0.23 mmol) of tetrakis(triphenylphosphine) palladium (0) were added to 30 mL of 1,4-dioxane and 15 mL of water in a 100 mL flask, and the mixture was heated under a nitrogen flow for 12 hours at 80° C. When a reaction was complete, a mixture obtained by removing an organic layer therefrom was added to 100 mL of methanol, and a solid crystallized therein was filtered, dissolved in toluene, filtered with silica gel/Celite, and after removing an appropriate amount of an organic solvent, recrystallized with methanol to obtain Compound 2 (3.57 g, a yield of 73%).

calcd. C48H32N2: C, 90.54; H, 5.07; N, 4.40; found: C, 90.54; H, 5.06; N, 4.40

SYNTHESIS EXAMPLE 2

Synthesis of Compound 5

[Reaction Scheme 2]

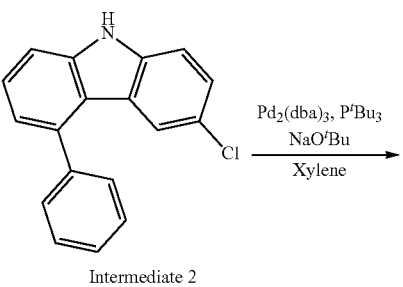

Intermediate 2

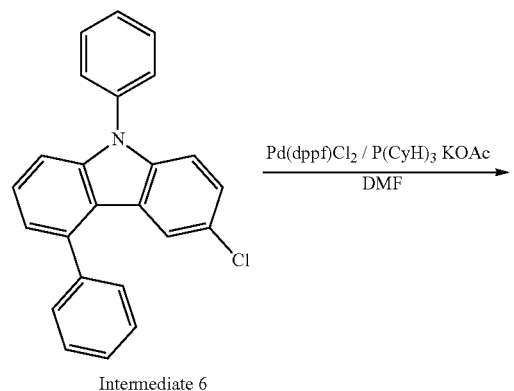

Intermediate 6

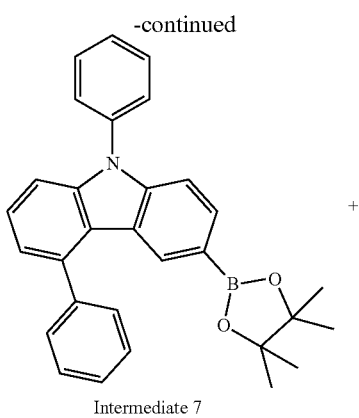

Intermediate 7

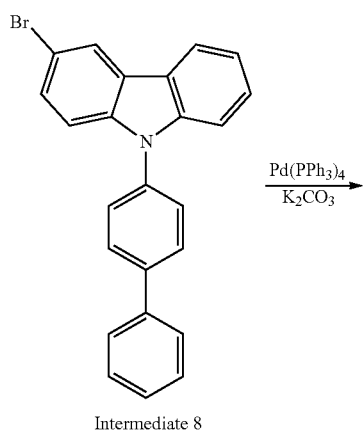

Intermediate 8

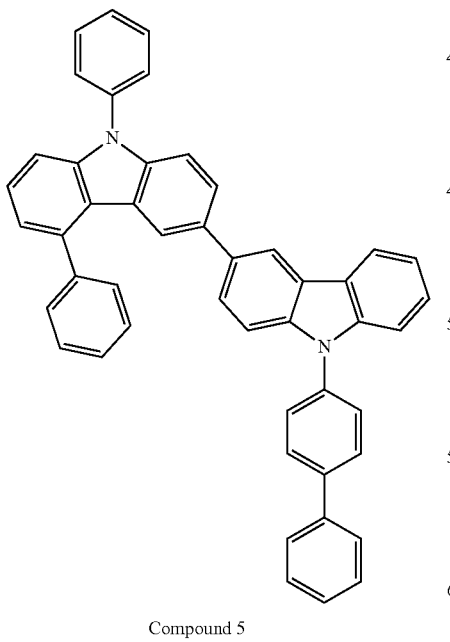

Compound 5

First Step: Synthesis of Intermediate 6

25.0 g (90.21 mmol) of Intermediate 2, 17.0 g (108.3 mmol) of bromobenzene, 17.34 g (180.4 mmol) of sodium t-butoxide, 5.19 g (9.02 mmol) of tris(dibenzylidene acetone)dipalladium, and 7.30 g of tri t-butylphosphine (50% in toluene) were added to 500 mL of xylene in a 1000 mL flask, and the mixture was heated and refluxed under a nitrogen flow for 15 hours. The obtained mixture was added to 1000 mL of methanol, and a solid crystallized therein was filtered, dissolved in monochlorobenzene with silica gel/Celite, and after removing an appropriate amount of an organic solvent, recrystallized with methanol to obtain Intermediate 6 (23.1 g, a yield of 72%).

Second Step: Synthesis of Intermediate 7

Intermediate 6 (23.0 g, 65.0 mmol), 4,4,4',4',5,5,5',5'-octamethyl-2,2'-bi(1,3,2-dioxaborolane) (19.8 g, 78.0 mmol), potassium acetate (KOAc, 19.14 g, 195.00 mmol), 1,1'-bis(diphenylphosphino) ferrocene-palladium(II) dichloride (3.18 g, 3.90 mmol), and tricyclohexylphosphine (5.47 g, 9.75 mmol) were added to 200 mL of N,N-dimethylformamide in a 500 mL flask, and the mixture was stirred at 130° C. for 24 hours. When a reaction was complete, the reaction solution was treated with water and EA to extract an organic layer, and the organic layer was treated with magnesium sulfate to remove moisture, concentrated, and purified through column chromatography to obtain Intermediate 7 (21.6 g, a yield of 75%).

Third Step: Synthesis of Compound 5

4.0 g (8.98 mol) of Intermediate 7, 3.58 g (8.98 mol) of Intermediate 8, 3.10 g (22.45 mol) of potassium carbonate, and 0.31 g (0.27 mmol) of tetrakis(triphenylphosphine) palladium (0) were added to 30 mL of 1,4-dioxane and 15 mL of water in a 100 mL flask, and the mixture was heated under a nitrogen flow for 12 hours at 80° C. When a reaction was complete, a mixture obtained by removing an organic layer therefrom was added to 100 mL of methanol, and a solid crystallized therein was filtered, dissolved in toluene, filtered with silica gel/Celite, and after removing an appropriate amount of an organic solvent, recrystallized with methanol to obtain Compound 5 (4.03 g, a yield of 70%).

calcd. C48H32N2: C, 90.54; H, 5.07; N, 4.40; found: C, 90.54; H, 5.07; N, 4.40

SYNTHESIS EXAMPLE 3

Synthesis of Compound 3

[Reaction Scheme 3]

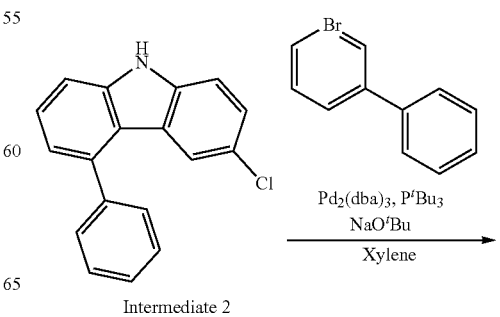

Intermediate 2

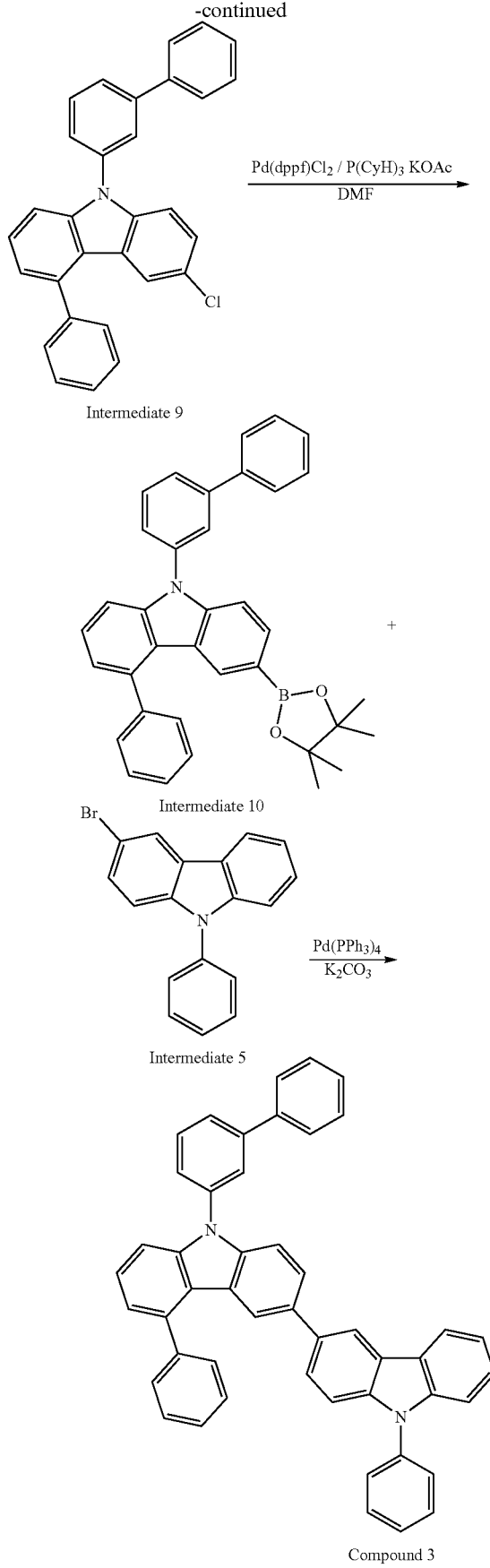
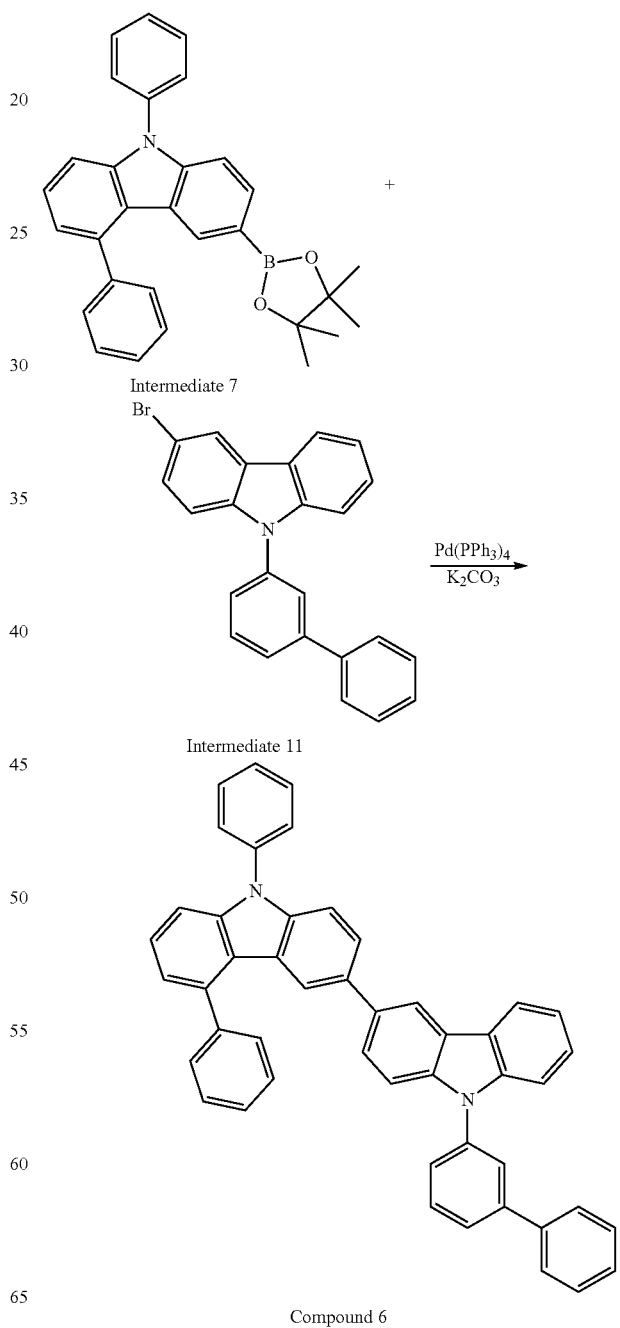
Step 1-3: Synthesis of Compound 3
Compound 3 (4.12 g, a yield of 69%) was obtained according to the same method as Synthesis Example 1 except for using Intermediate 10 instead of Intermediate 4.
calcd. C48H32N2: C, 90.54; H, 5.07; N, 4.40; found: C, 90.53; H, 5.07; N, 4.40
SYNTHESIS EXAMPLE 4
Synthesis of Compound 6
[Reaction Scheme 4]

First Step: Synthesis of Compound 6

Compound 4 (4.49 g, a yield of 73%) was obtained according to the same method as Compound 5 of Synthesis Example 5 except for using Intermediate 11 instead of Intermediate 8.

calcd. C48H32N2: C, 90.54; H, 5.07; N, 4.40; found: C, 90.54; H, 5.07; N, 4.40

SYNTHESIS EXAMPLE 5

Synthesis of Compound 8

[Reaction Scheme 5]

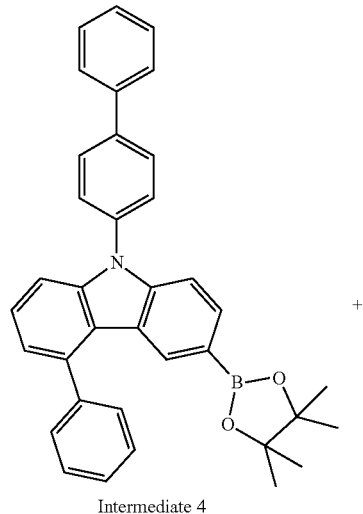

Intermediate 4

+

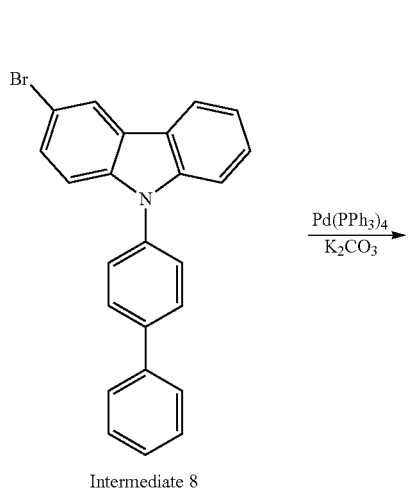

Intermediate 8

$\xrightarrow{\text{Pd(PPh}_3)_4}{\text{K}_2\text{CO}_3}$

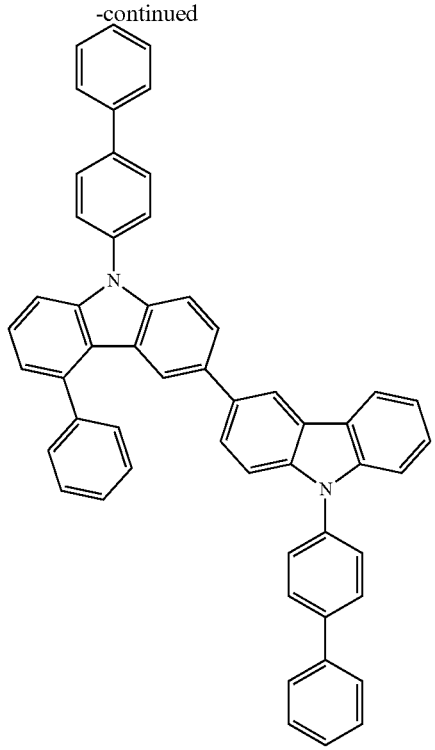

Compound 8

First Step: Synthesis of Compound 8

Compound 8 (4.22 g, a yield of 75%) was obtained according to the same method as Compound 5 of Synthesis Example 5 except for using Intermediate 4 instead of Intermediate 7.

calcd. C54H36N2: C, 90.98; H, 5.09; N, 3.93; found: C, 90.98; H, 5.09; N, 3.93.

SYNTHESIS EXAMPLE 6

Synthesis of Compound 9

[Reaction Scheme 6]

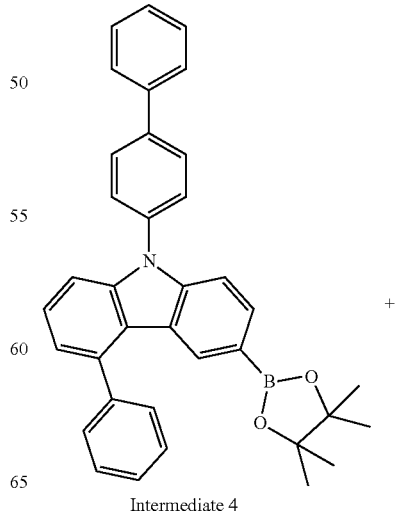

Intermediate 4

-continued
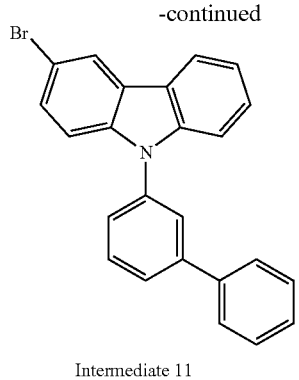
Intermediate 11
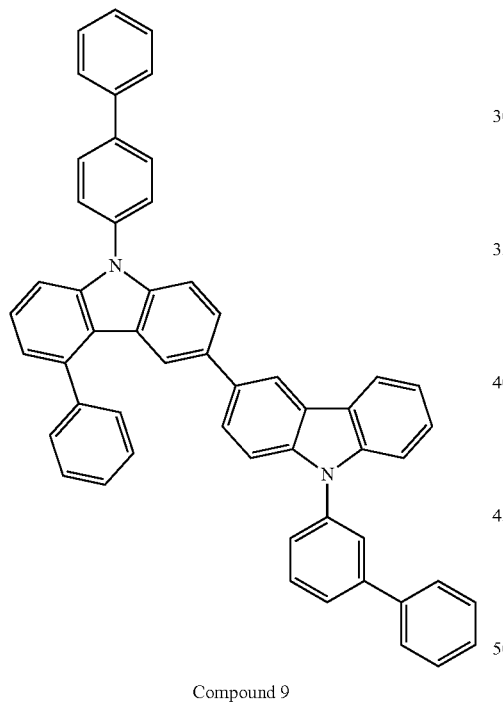
Compound 9
First Step: Synthesis of Compound 9
Compound 9 (3.95 g, a yield of 71%) was obtained according to the same method as Compound 4 of Synthesis Example 4 except for using Intermediate 4 instead of Intermediate 7.
calcd. C54H36N2: C, 90.98; H, 5.09; N, 3.93; found: C, 90.97; H, 5.09; N, 3.93
SYNTHESIS EXAMPLE 7
Synthesis of Compound 10
[Reaction Scheme 7]
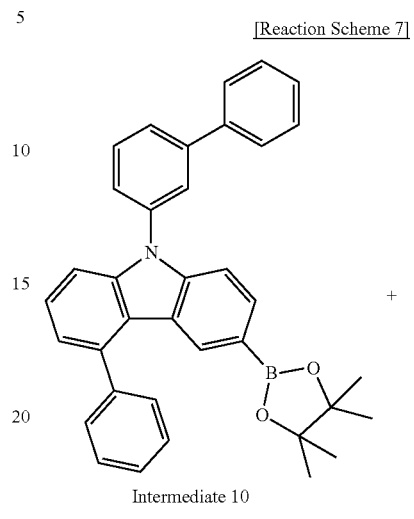
Intermediate 10
+
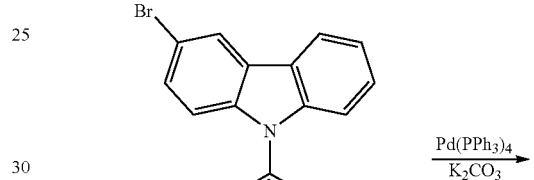
Intermediate 8
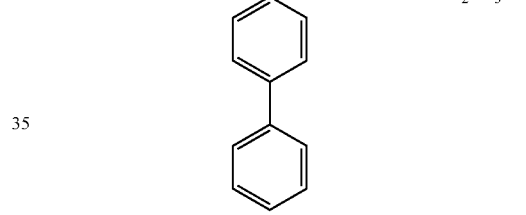
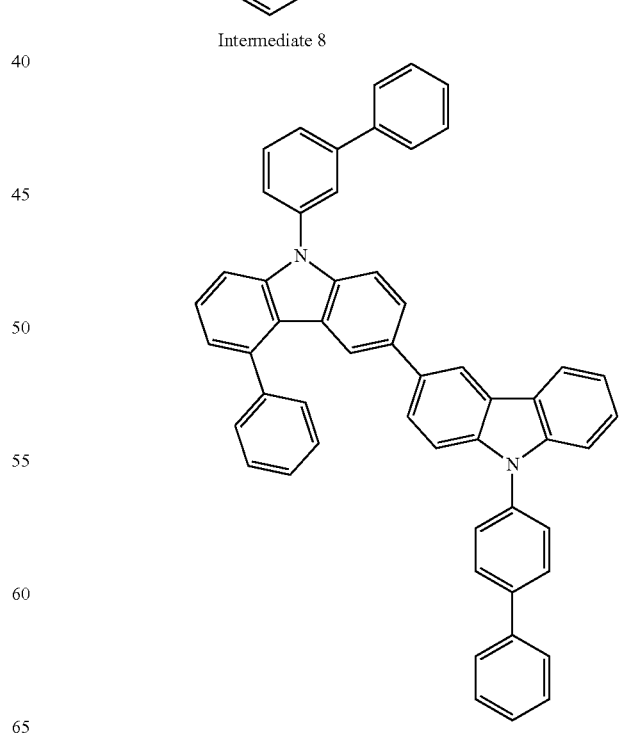
Compound 10

First Step: Synthesis of Compound 10

Compound 10 (4.06 g, a yield of 68%) was obtained according to the same method as Compound 8 of Synthesis Example 5 except for using Intermediate 10 instead of Intermediate 4.

calcd. C54H36N2: C, 90.98; H, 5.09; N, 3.93; found: C, 90.98; H, 5.09; N, 3.92.

SYNTHESIS EXAMPLE 8

Synthesis of Compound 11

[Reaction Scheme 8]

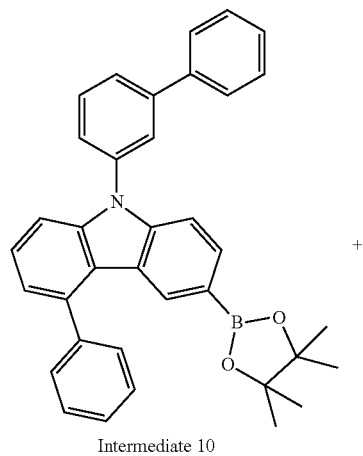

Intermediate 10

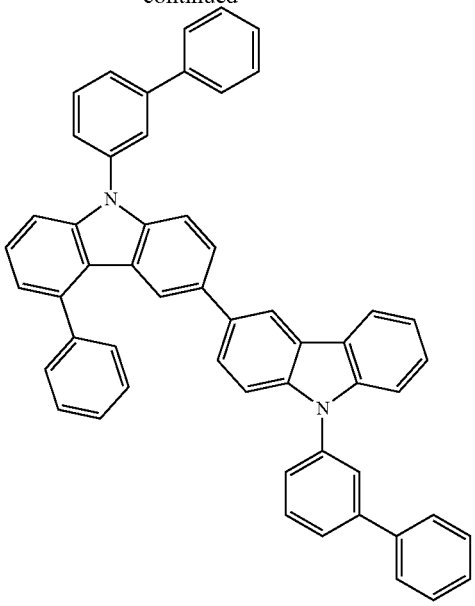

Compound 11

First Step: Synthesis of Compound 11

Compound 11 (3.49 g, a yield of 63%) was obtained according to the same method as Compound 6 of Synthesis Example 4 except for using Intermediate 10 instead of Intermediate 7.

calcd. C54H36N2: C, 90.98; H, 5.09; N, 3.93; found: C, 90.98; H, 5.09; N, 3.93

SYNTHESIS EXAMPLE 9

Synthesis of Compound 12

[Reaction Scheme 9]

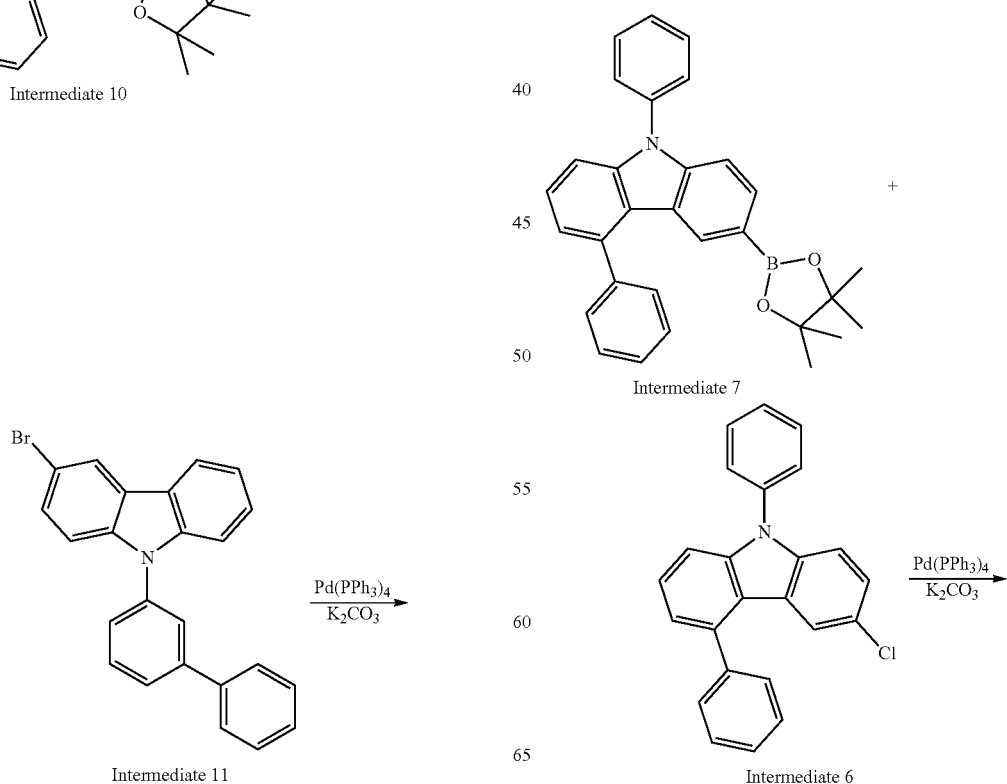

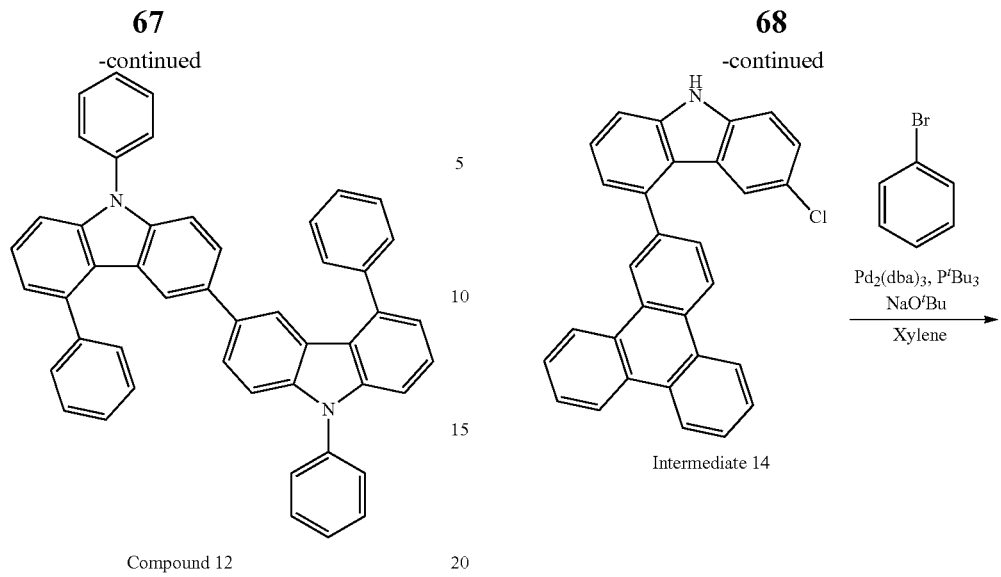
Compound 12
First Step: Synthesis of Compound 11
Compound 12 (2.31 g, a yield of 23%) was obtained according to the same method as Compound 6 of Synthesis Example 4 except for using Intermediate 6 instead of Intermediate 11.
calcd. C48H32N2: C, 90.54; H, 5.07; N, 4.40; found: C, 90.54; H, 5.07; N, 4.40
SYNTHESIS EXAMPLE 10
Synthesis of Compound 23
[Reaction Scheme 10]
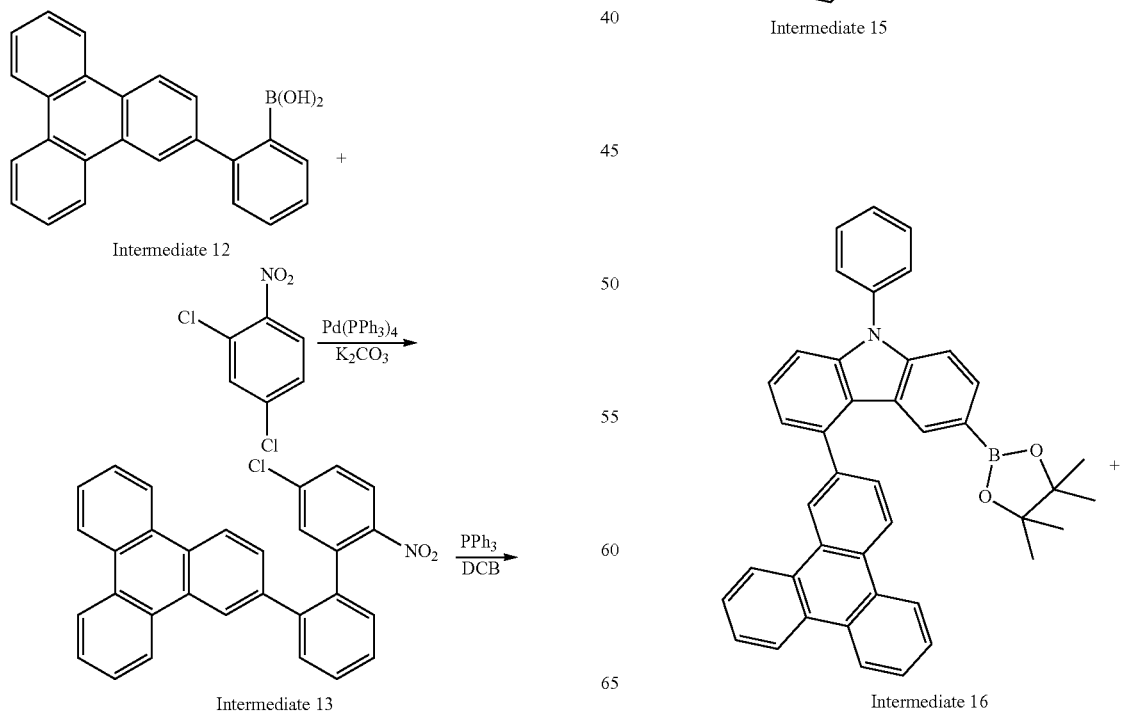

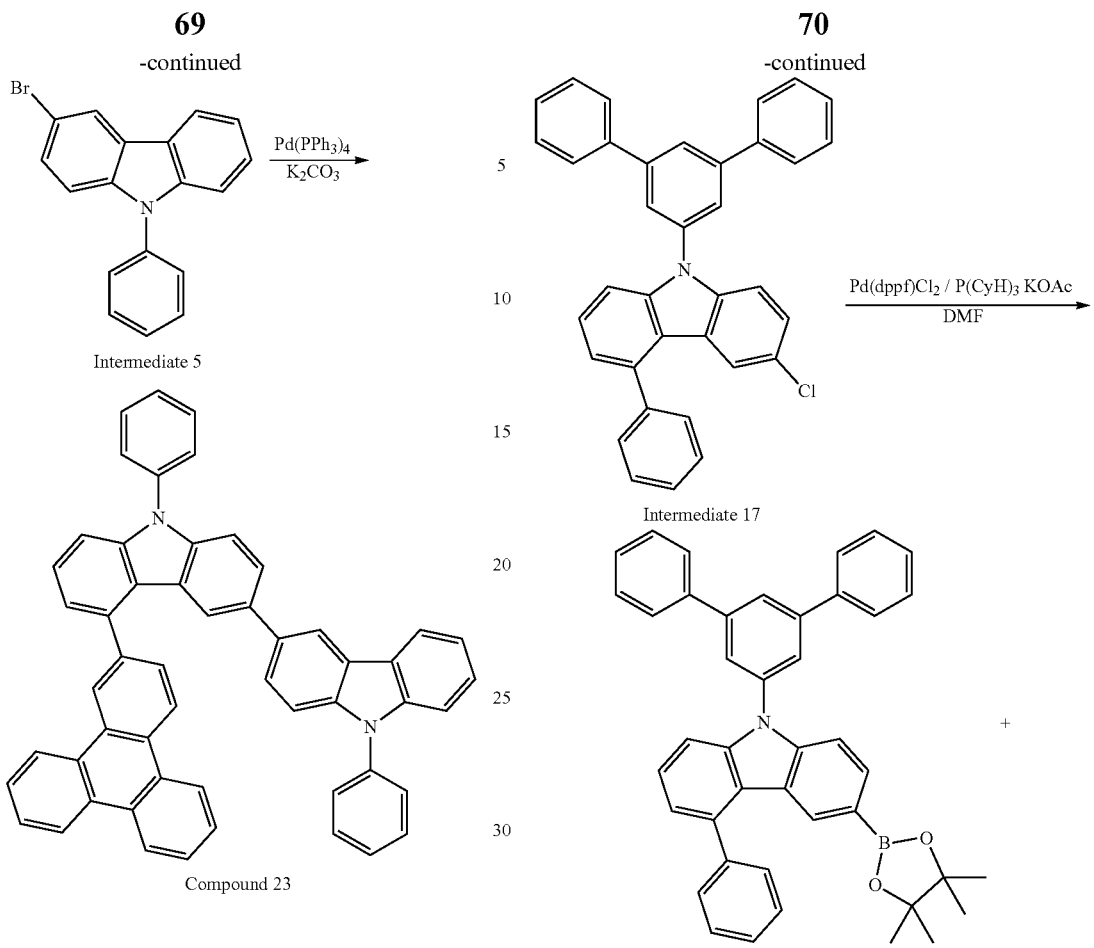
Step 1-5: Synthesis of Compound 23
Compound 23 (5.18 g, a yield of 75%) was obtained according to the same method as Compound 2 of Synthesis Example 1 except for using Intermediate 13 instead of Intermediate 1.
calcd. C54H34N2: C, 91.24; H, 4.82; N, 3.94; found: C, 91.24; H, 4.82; N, 3.94
SYNTHESIS EXAMPLE 11
Synthesis of Compound 27
[Reaction Scheme 11]
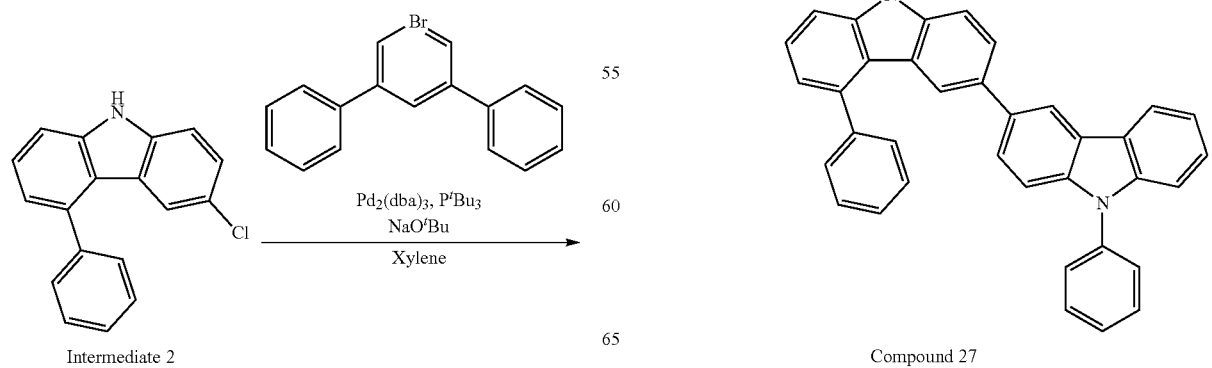

Step 1-3: Synthesis of Compound 27
Compound 27 (4.72 g, a yield of 68%) was obtained according to the same method as Compound 2 of Synthesis Example 1 except for using 1-bromo-3,5-diphenylbenzene instead of 4-bromoparabiphenyl.
calcd. C54H36N2: C, 90.98; H, 5.09; N, 3.93; found: C, 90.98; H, 5.09; N, 3.93.
SYNTHESIS EXAMPLE 12
Synthesis of Compound 34
[Reaction Scheme 12]
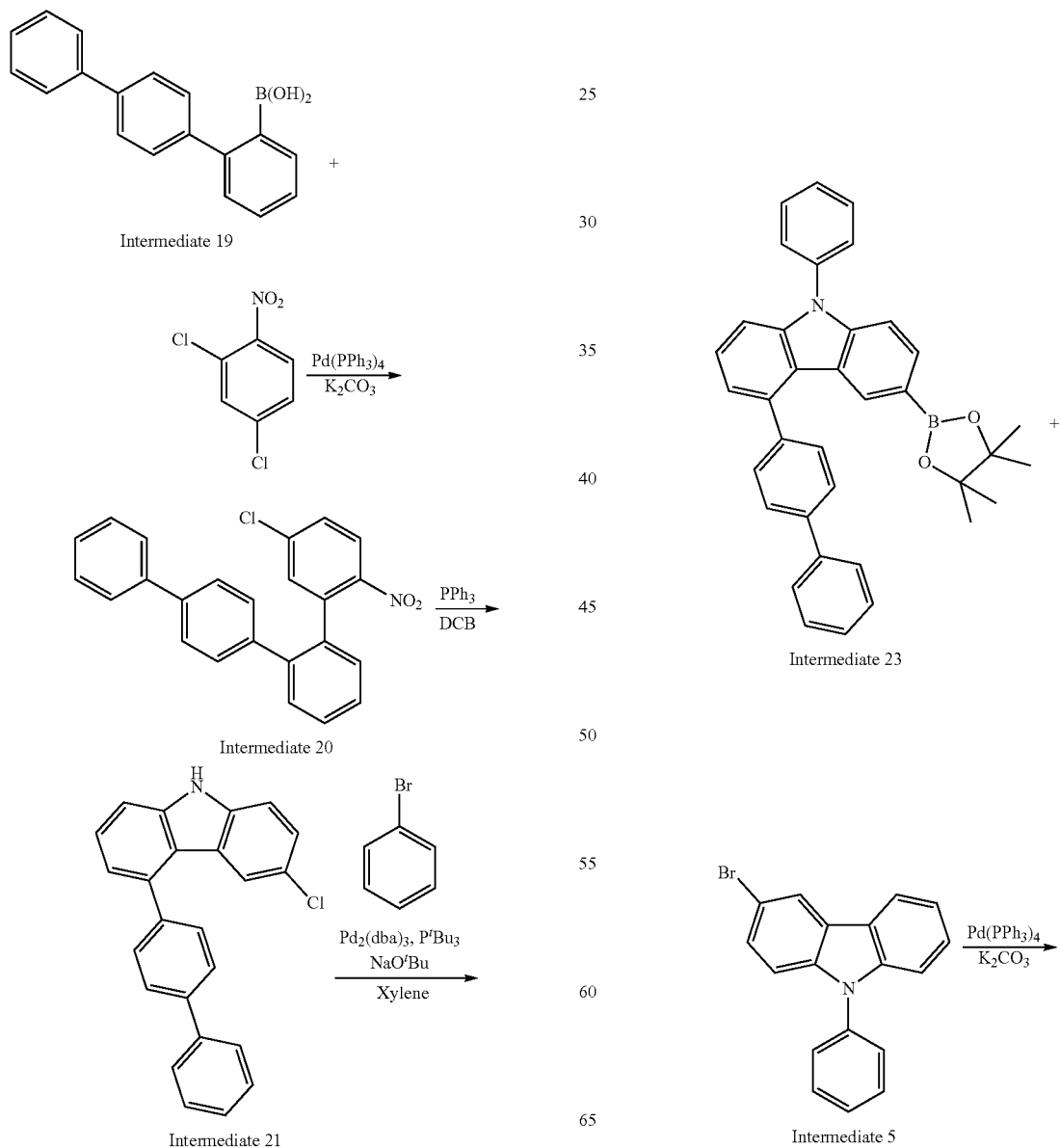
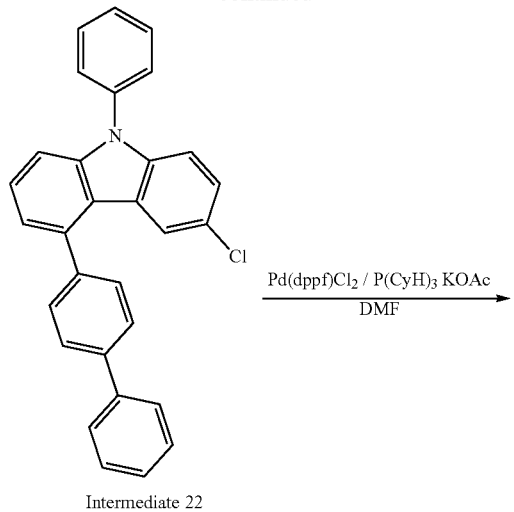

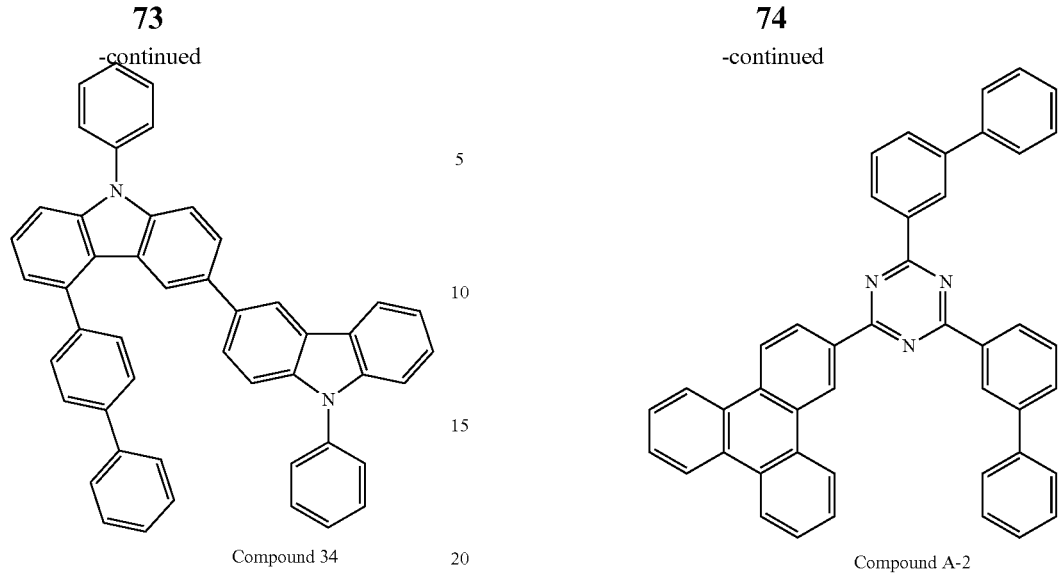

Compound 34

Step 1-5: Synthesis of Compound 34

Compound 34 (4.42 g, a yield of 70%) was obtained according to the same method as Compound 2 of Synthesis Example 1 except for using Intermediate 19 instead of biphenyl-2-boronic acid.

calcd. C48H32N2: C, 90.54; H, 5.07; N, 4.40; found: C, 90.54; H, 5.07; N, 4.40

Synthesis of Second Compound for Organic Optoelectric Device

SYNTHESIS EXAMPLE 13

Synthesis of Compound A-2

[Reaction Scheme 13]

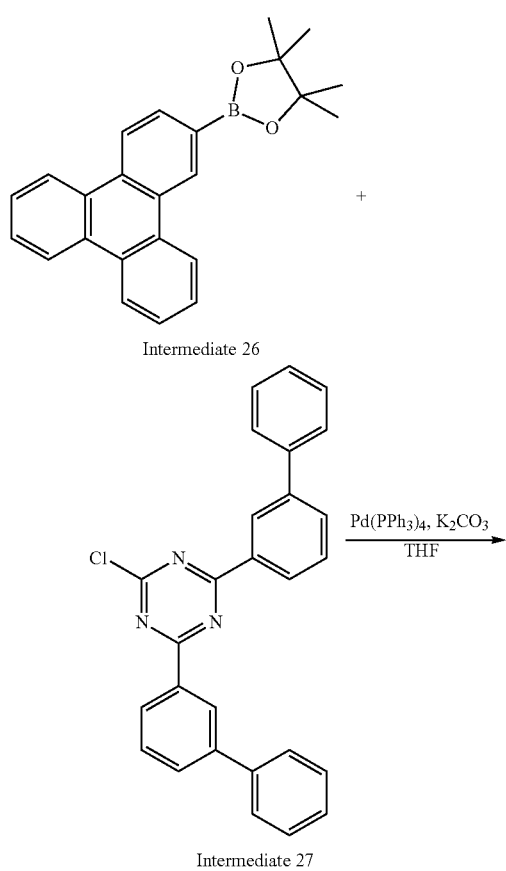

Compound A-2

Intermediate 26 (39.5 mmol) was dissolved in 0.2 L of tetrahydrofuran (THF) under a nitrogen environment, Intermediate 27 (39.5 mmol) and tetrakis(triphenylphosphine) palladium (0.46 g, 0.4 mmol) were added thereto, and the mixture was stirred. Potassium carbonate saturated in water (13.6 g, 98.8 mmol) was added thereto, and the obtained mixture was heated and refluxed at 80° C. for 23 hours. When a reaction was complete, water was added to the reaction solution, dichloromethane (DCM) was used for an extraction, anhydrous $MgSO_4$ was used to remove moisture from an extract, and the extract was filtered and concentrated under a reduced pressure. The obtained residue was separated and purified through flash column chromatography to obtain Compound A-2 (a yield of 75%).

calcd. C45H29N3: C, 88.35; H, 4.78; N, 6.87; found: C, 88.35; H, 4.78; N, 6.87.

Manufacture of Organic Light Emitting Diode (Light Emitting Layer Device-single Host)

EXAMPLE 1

An organic light emitting diode was manufactured by using Compound 2 obtained in Synthesis Example 1 as a host and Ir(Ply)$_3$ as a dopant.

As for an anode, 1000 Å-thick ITO was used, and as for a cathode, 1000 Å-thick aluminum was used. Specifically, illustrating a method of manufacturing the organic light emitting diode, the anode is manufactured by cutting an ITO glass substrate having 15 Ω/cm$^2$ of a sheet resistance into a size of 50 mm×50 mm×0.7 mm, ultrasonic wave-cleaning them in each acetone, isopropyl alcohol, and pure water for 15 minutes respectively, and UV ozone cleaning them for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick light emitting layer was formed by using Compound 2 of Synthesis Example 1 under the same vacuum deposition condition, and a phosphorescent dopant of Ir(PPy)$_3$ was simultaneously deposited. Herein, the phosphorescent dopant was deposited to be 10 wt % based on 100 wt % of a total weight of the light emitting layer by adjusting the deposition rate.

On the light emitting layer, a 50 Å-thick hole blocking layer was formed by depositing bis(2-methyl-8-quinolinolate)-4-(phenylphenolato)aluminum (BAlq) under the same vacuum deposition condition. Subsequently, a 200 Å-thick electron transport layer was formed by depositing Alq3 under the same vacuum deposition condition. On the electron transport layer, a cathode was formed by sequentially depositing LiF and Al to manufacture an organic light emitting diode.

A structure of the organic light emitting diode was ITO/NPB (80 nm)/EML (Compound 2 (90 wt %)+Ir(PPy)$_3$ (10 wt %), 30 nm)/BAlq (5 nm)/Alq3 (20 nm)/LiF (1 nm)/Al (100 nm).

Manufacture of Organic Light Emitting Diode (Light Emitting Layer-mixed Host)

EXAMPLE 2

An organic light emitting diode was manufactured according to the same method as Example 1 except for forming a 400 Å-thick light emitting layer by codepositing Ir(ppy)$_3$ (a dopant), Compound 2 (a first host), and Compound A-1 (a second host) in a weight ratio of 10:45:45 on a hole transport layer.

EXAMPLES 3 to 17

Organic light emitting diodes according to Examples 3 to 7 were respectively manufactured according to the same method as Example 2 except for using the first hosts and the second hosts of Table 2 when forming a light emitting layer

COMPARATIVE EXAMPLE 1

An organic light emitting diode was manufactured according to the same method as Example 1 except for using Compound D instead of Compound 2 as a host for forming a light emitting layer.

<Compound D>

COMPARATIVE EXAMPLES 2 to 7

Organic light emitting diodes according to Examples 2 to 7 of [Table 2] were respectively manufactured according to the same method as Example 2 except for using each Compound A to F instead of Compound 2 as a host for forming a light emitting layer.

<Compound A>

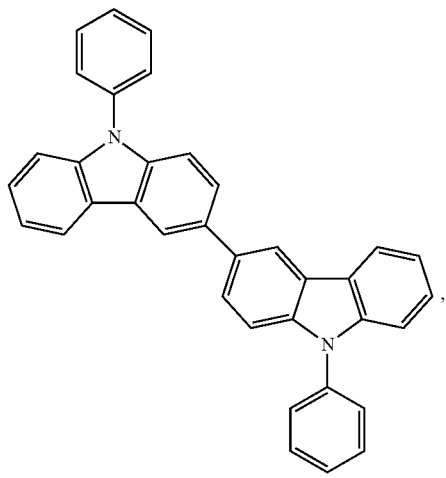

<Compound B>

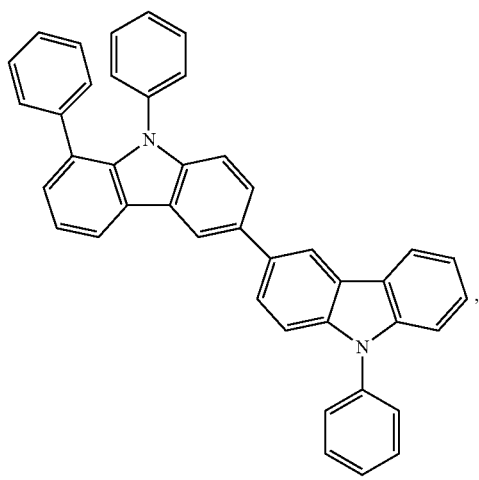

<Compound C>

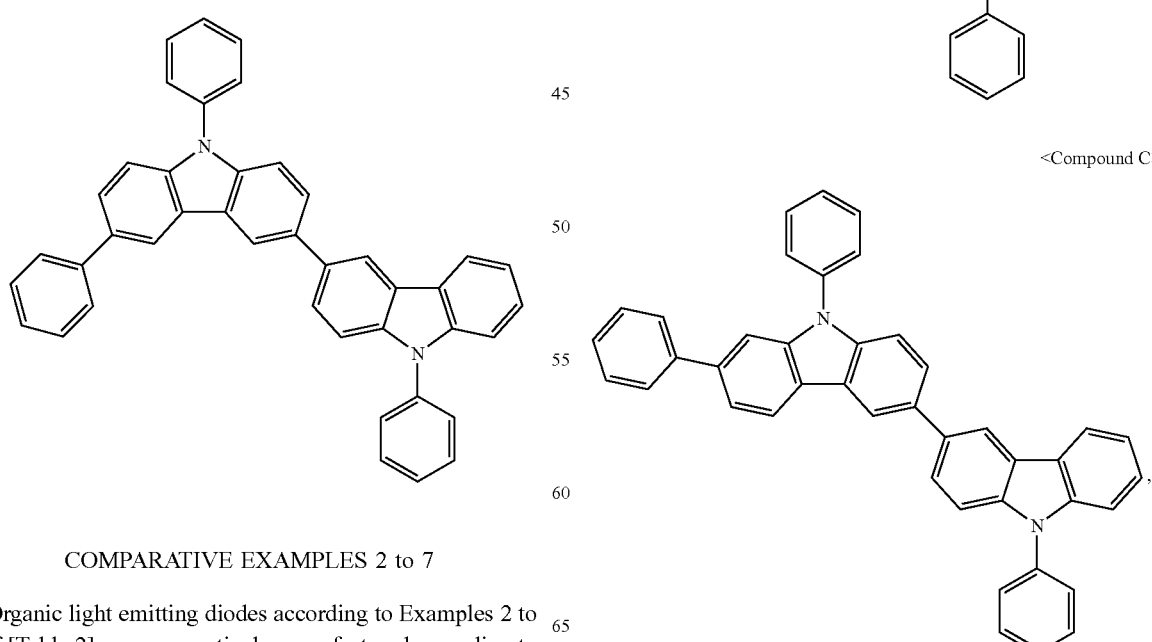

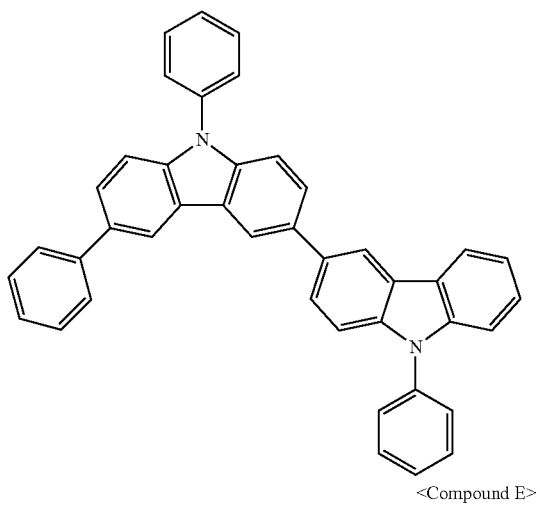

EVALUATION EXAMPLE 1

Evaluation of Characteristics of Organic Light Emitting Diode (I)

Luminous efficiency and life-span characteristics of each organic light emitting diode according to Examples 1 to 17 and Comparative Examples 1 to 7 were evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by an area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm2) were calculated by using the luminance, current density, and voltages (V) from the items (1) and (2).

A driving voltage, efficiency, luminance, and a life-span of each organic light emitting diode according to Examples 1 to 17 and Comparative Examples 1 to 7 were measured by supplying power from a current voltage meter (Kethley SMU 236) and using a luminance meter, PR650 Spectroscan Source Measurement Unit (Photo Research Inc.), and the results are shown in Table 1 and Table 2.

(4) Measurement of Driving Voltage

A driving voltage of each diode was measured using a current-voltage meter (Keithley 2400) at 15 mA/cm$^2$.

TABLE 1

| | Host | Driving Voltage (V) | Current efficiency (cd/A) | Luminance (cd/m$^2$) |
|---|---|---|---|---|
| Example 1 | Compound 2 | 7.16 | 4.6 | 6000 |
| Comparative Example 1 | Compound D | 7.63 | 4.2 | 6000 |

TABLE 2

| | First host | Second host | Driving Voltage (V) | Current efficiency (cd/A) | Luminance (cd/m$^2$) |
|---|---|---|---|---|---|
| Example 2 | Compound 2 | A-1 | 3.75 | 69.4 | 6000 |
| Example 3 | Compound 5 | A-1 | 3.80 | 70.2 | 6000 |
| Example 4 | Compound 3 | A-1 | 3.86 | 69.2 | 6000 |
| Example 5 | Compound 6 | A-1 | 3.89 | 69.5 | 6000 |
| Example 6 | Compound 8 | A-1 | 3.69 | 68.7 | 6000 |
| Example 7 | Compound 9 | A-1 | 3.77 | 68.4 | 6000 |
| Example 8 | Compound 10 | A-1 | 3.81 | 68.9 | 6000 |
| Example 9 | Compound 11 | A-1 | 3.94 | 67.3 | 6000 |
| Example 10 | Compound 12 | A-1 | 3.75 | 69.2 | 6000 |
| Example 11 | Compound 23 | A-1 | 3.70 | 67.7 | 6000 |
| Example 12 | Compound 27 | A-1 | 3.88 | 68.2 | 6000 |
| Example 13 | Compound 34 | A-1 | 3.65 | 69.2 | 6000 |
| Example 14 | Compound 2 | A-2 | 3.62 | 70.3 | 6000 |
| Example 15 | Compound 5 | A-2 | 3.65 | 70.5 | 6000 |
| Example 16 | Compound 2 | b-2 | 3.60 | 71.0 | 6000 |
| Example 17 | Compound 5 | b-2 | 3.58 | 70.4 | 6000 |
| Comparative Example 2 | Compound A | A-1 | 4.12 | 61.3 | 6000 |
| Comparative Example 3 | Compound B | A-1 | 4.19 | 57.2 | 6000 |
| Comparative Example 4 | Compound C | A-1 | 4.09 | 58.5 | 6000 |
| Comparative Example 5 | Compound D | A-1 | 4.07 | 62.6 | 6000 |
| Comparative Example 6 | Compound E | A-1 | 3.99 | 53.1 | 6000 |
| Comparative Example 7 | Compound F | A-1 | 4.29 | 54.8 | 6000 |

From Tables 1 and 2, the compounds of the present disclosure showed a low driving voltage and high efficiency compared with the compounds of Comparative Examples, and in addition showed a low driving voltage and high efficiency by being used with the second host material.

Manufacture of Organic Light Emitting Diode (Hole Transport Layer (HTL))

EXAMPLE 18

An organic light emitting diode was manufactured according to the same method as Example 2 except for using Compound 2 instead of NPB in the hole transport layer.

EXAMPLE 19

An organic light emitting diode was manufactured according to the same method as Example 18 except for using Compound 5 instead of Compound 2 in the light emitting layer.

COMPARATIVE EXAMPLE 8

An organic light emitting diode was manufactured according to the same method as Example 2 except for not including the hole transport layer.

EVALUATION EXAMPLE 2

Evaluation of Characteristics of Organic Light Emitting Diode (II)

A driving voltage, efficiency, luminance, and a life-span of each organic light emitting diode according to Examples 18 and 19 and Comparative Examples 5 and 8 were measured according to the same method as Evaluation Example 1 by supplying power from a current voltage meter (Kethley SMU 236) and using a luminance meter, PR650 Spectroscan Source Measurement Unit (Photo Research Inc.), and the results are shown in Table 3.

TABLE 3

| | Hole transport layer | First host | Second host | Driving Voltage (V) | Current efficiency (cd/A) | Luminance (cd/m$^2$) |
|---|---|---|---|---|---|---|
| Example 18 | Compound 2 | Compound 2 | Compound A-1 | 3.61 | 70.4 | 6000 |
| Example 19 | Compound 2 | Compound 5 | Compound A-1 | 3.78 | 71.3 | 6000 |
| Comparative Example 5 | NPB | Compound D | Compound A-1 | 4.07 | 62.6 | 6000 |
| Comparative Example 8 | Not used | Compound 2 | Compound A-1 | 6.48 | 25.3 | 6000 |

From Table 3, the organic light emitting diodes using the compound of the present disclosure in the hole transport layer showed a low driving voltage and high efficiency compared with those using Comparative Example compounds.

DESCRIPTION OF SYMBOLS

100, 200: organic light emitting diode
105: organic layer
110: cathode
120: anode
130: light emitting layer
140: hole auxiliary layer Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectric device represented by Chemical Formula 1:

[Chemical Formula 1]

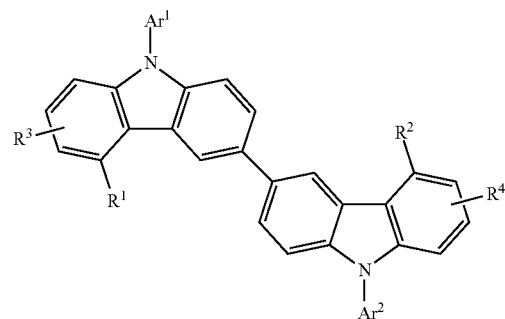

wherein, in Chemical Formula 1,
$R^1$ is a substituted or unsubstituted C6 to C30 aryl group,
$R^2$ is hydrogen, deuterium, a substituted or unsubstituted C1 to C10 alkyl group, or a substituted or unsubstituted C6 to C30 aryl group,
$R^3$ is hydrogen or deuterium,
$R^4$ is hydrogen, deuterium, a substituted or unsubstituted C1 to C10 alkyl group, or a substituted or unsubstituted C6 to C30 aryl group,
$Ar^1$ and $Ar^2$ are independently a substituted or unsubstituted C6 to C30 aryl group, a substituted or unsubstituted C2 to C30 heterocyclic group, or a combination thereof, and
the "substituted" refers to replacement of at least one hydrogen by deuterium, a C1 to C4 alkyl group, or a C6 to C18 aryl group.

2. The compound for an organic optoelectric device as claimed in claim 1, wherein the compound is represented by one of Chemical Formula 1-1 to Chemical Formula 1-3:

[Chemical Formula 1-1]

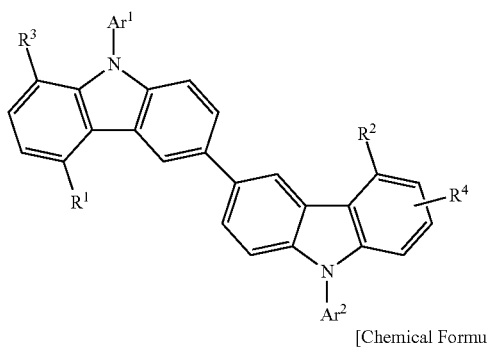

[Chemical Formula 1-2]

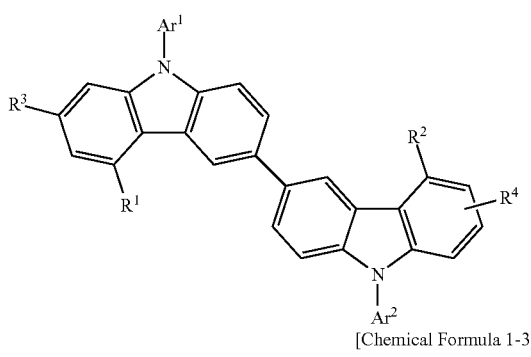

[Chemical Formula 1-3]

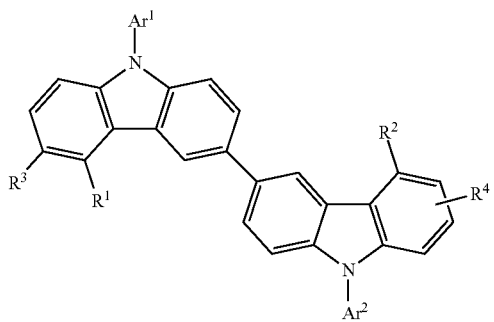

wherein, in Chemical Formula 1, $R^1$ is a substituted or unsubstituted C6 to C30 aryl group, $R^2$ is hydrogen, deuterium, a substituted or unsubstituted C1 to C10 alkyl group, or a substituted or unsubstituted C6 to C30 aryl group, $R^3$ is hydrogen or deuterium, $R^4$ is hydrogen, deuterium, a substituted or unsubstituted C1 to C10 alkyl group, or a substituted or unsubstituted C6 to C30 aryl group, and $Ar^1$ and $Ar^2$ are independently a substituted or unsubstituted C6 to C30 aryl group, a substituted or unsubstituted C2 to C30 heterocyclic group, or a combination thereof.

3. The compound for an organic optoelectric device as claimed in claim 1, wherein $R^1$ is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group, $R^2$ and $R^4$ are independently hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group, and $R^3$ is hydrogen or deuterium.

4. The compound for an organic optoelectric device as claimed in claim 1, wherein $R^1$ and $R^2$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group, $R^3$ is hydrogen or deuterium, and $R^4$ is hydrogen, deuterium, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylene group.

5. The compound for an organic optoelectric device as claimed in claim 1, wherein:

$R^1$ is selected from substituents of Group I, $R^2$ and $R^4$ are independently hydrogen or selected from substituents of Group I:

[Group I]

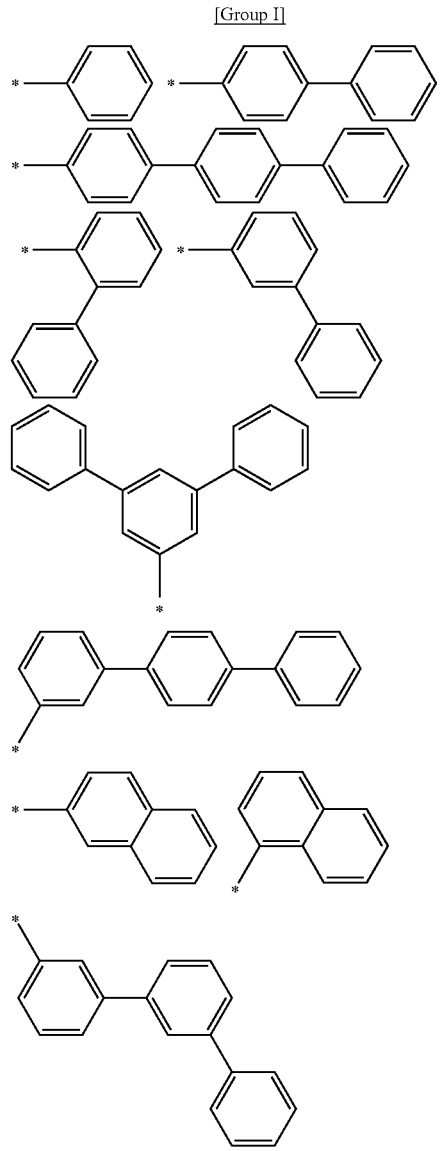

-continued

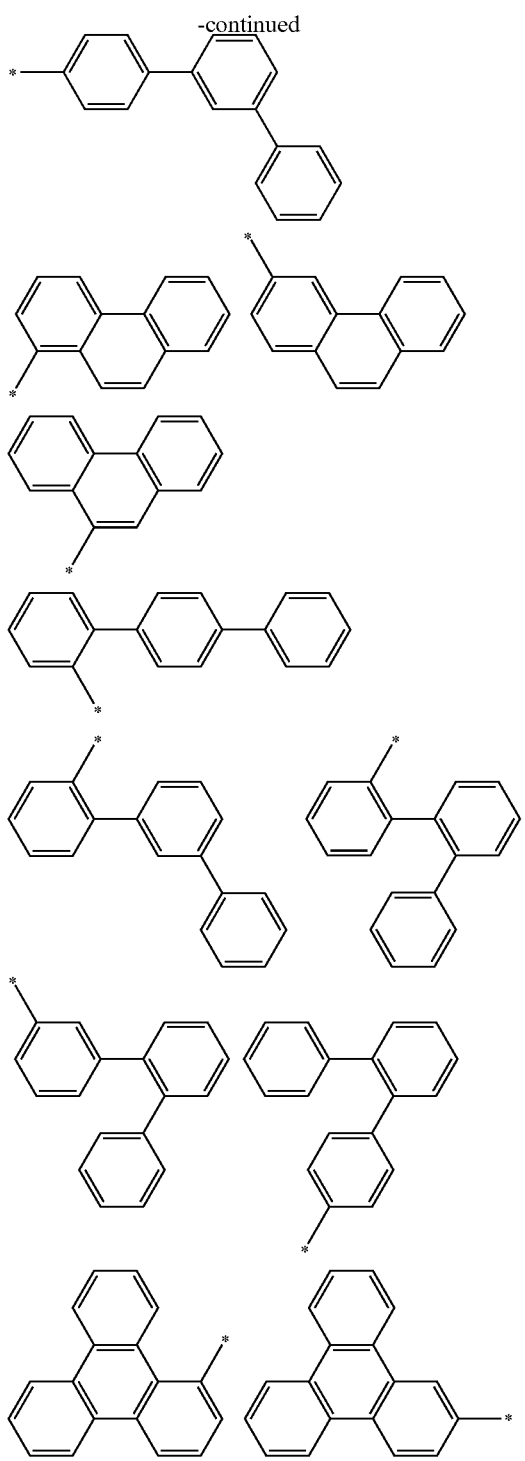

wherein, in Group I, * is a linking point with an adjacent atom, and
R³ is hydrogen.

6. The compound for an organic optoelectric device as claimed in claim 1, wherein $Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, or a combination thereof.

7. The compound for an organic optoelectric device as claimed in claim 1, wherein:

at least one of $R^1$ and $R^2$ is a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, or a substituted or unsubstituted triphenylene group, and $Ar^1$ and $Ar^2$ are independently a substituted or unsubstituted phenyl group, a substituted or unsubstituted biphenyl group, or a substituted or unsubstituted terphenyl group.

8. The compound for an organic optoelectric device as claimed in claim 1, wherein the compound is selected from compounds of Group 1:

[Group 1]

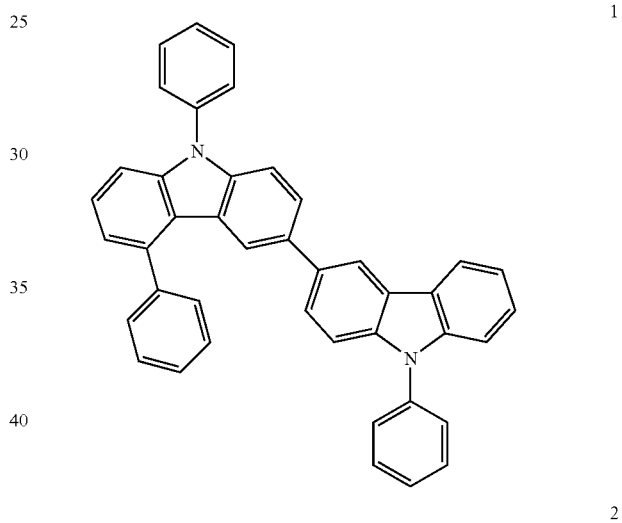

1

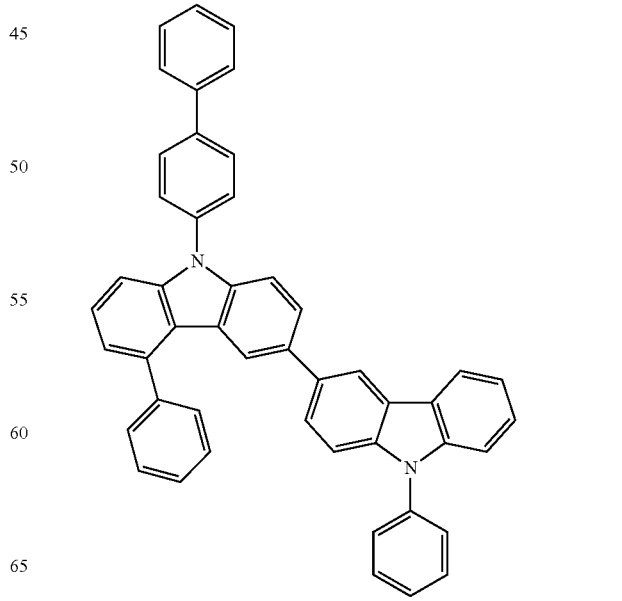

2

3
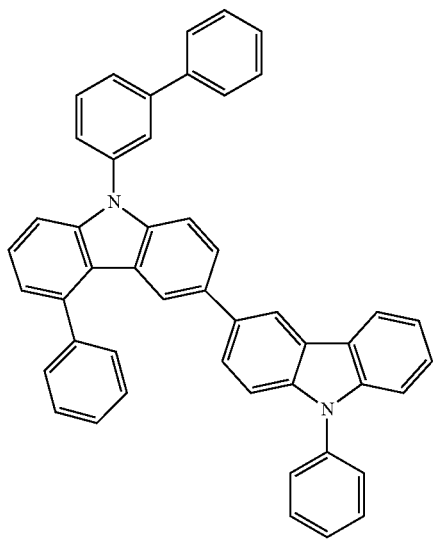
4
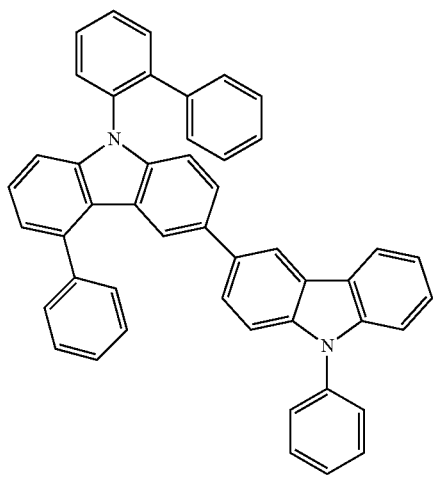
5
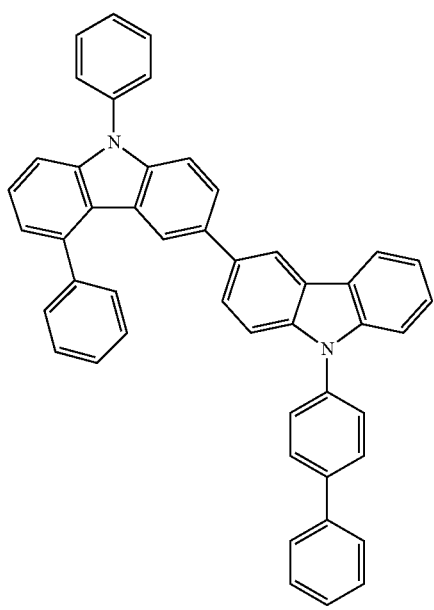
6
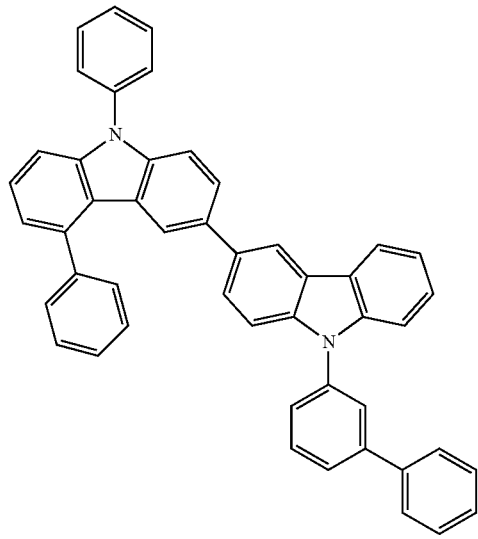
7
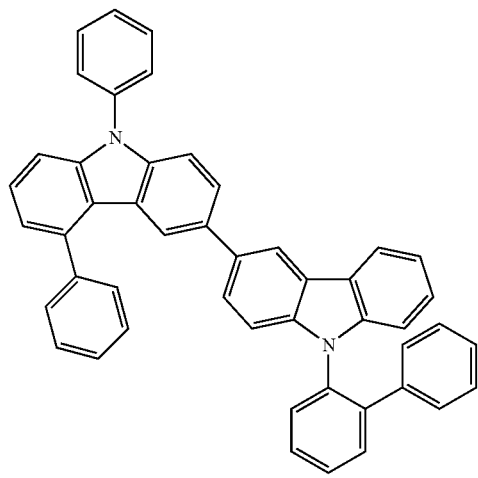
8
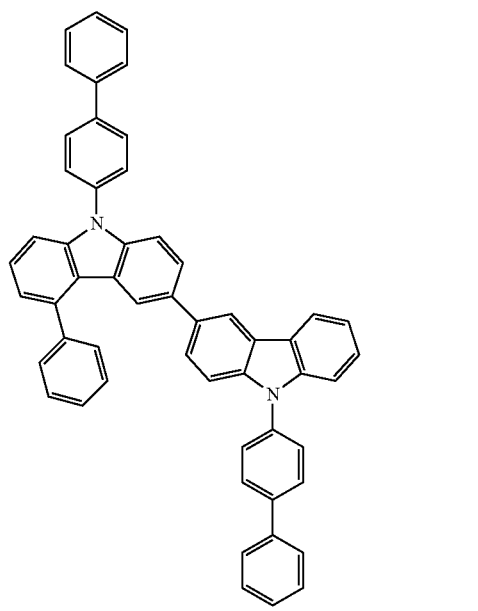

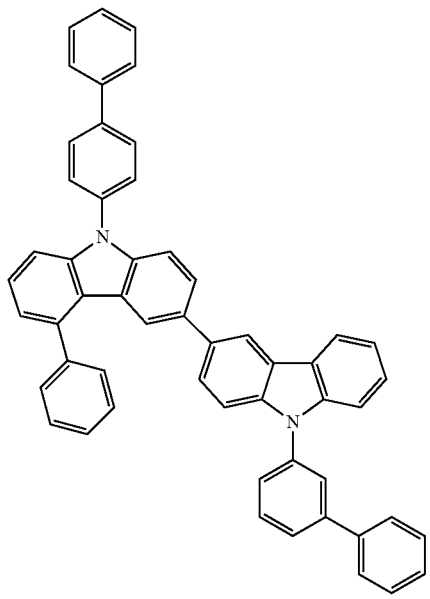
9
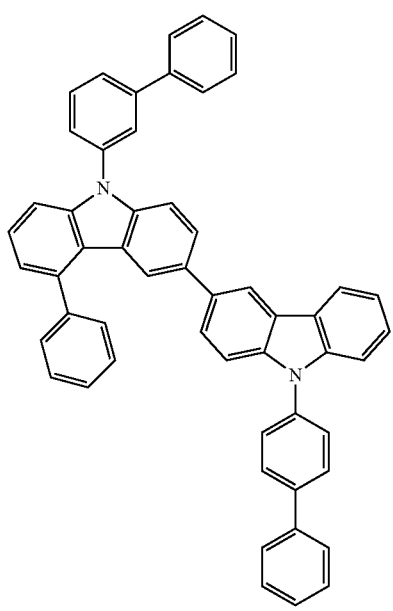
10

13
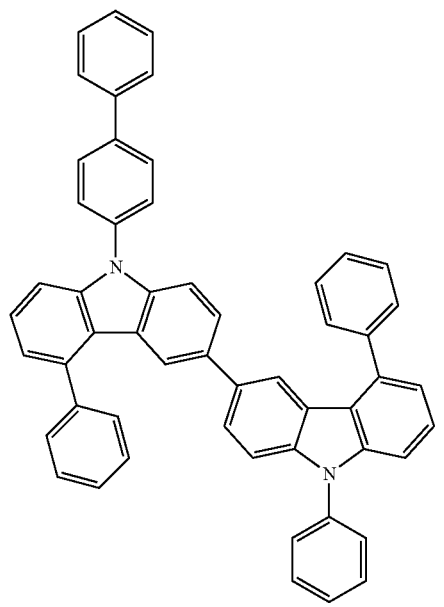
14
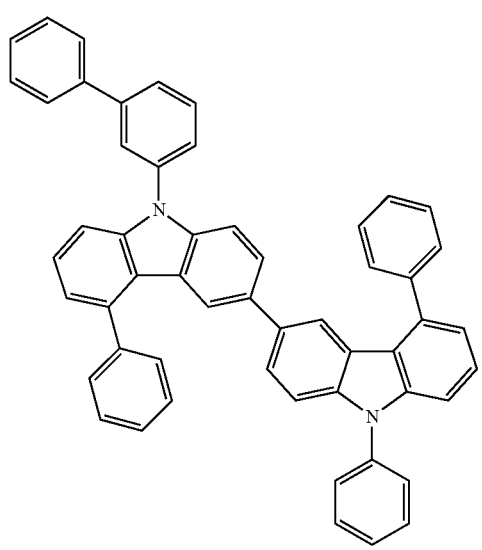
15
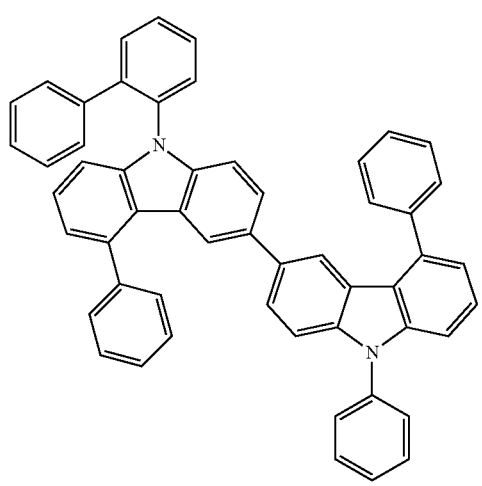
16
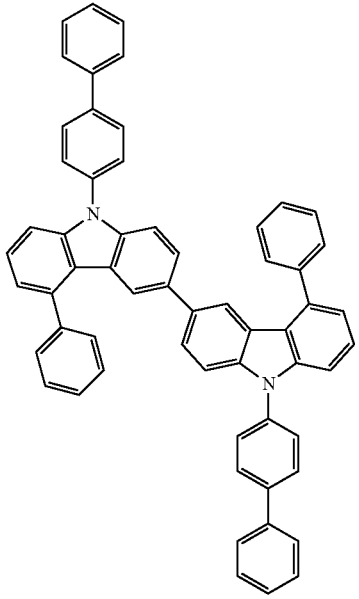
17

18
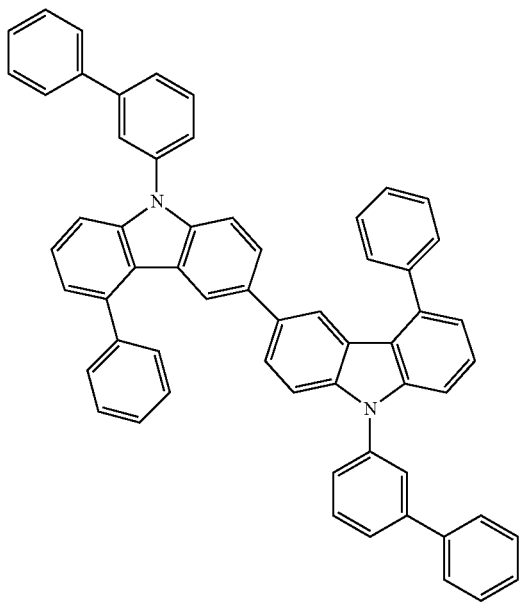
24
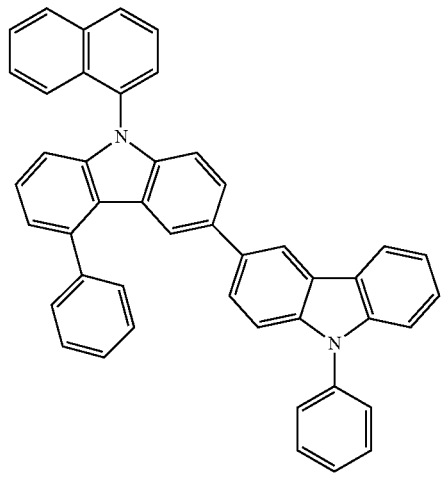
22
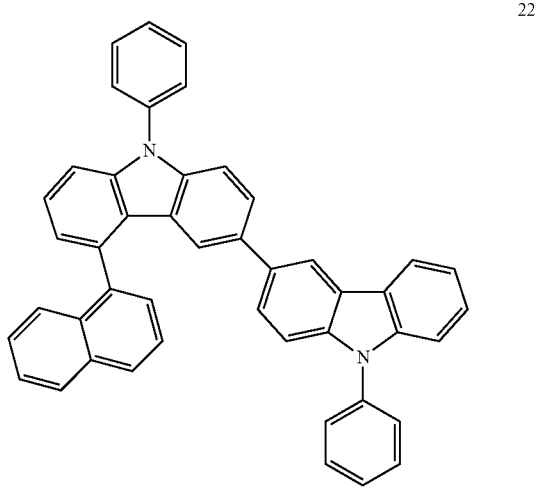 [SMILES: c1ccc(-n2c3ccccc3c3cc(-c4ccc5c(c4)c4c(-c6cccc7ccccc67)cccc4n5-c4ccccc4)ccc32)cc1]
25
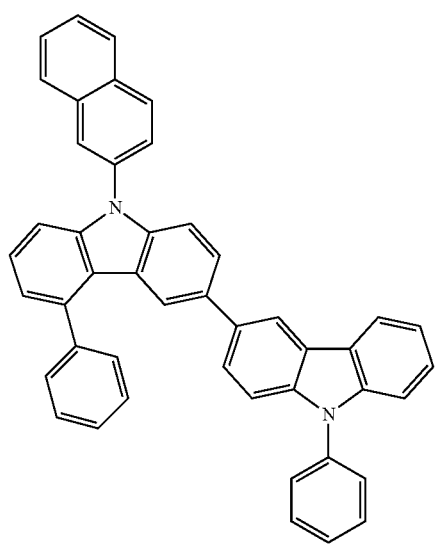
23
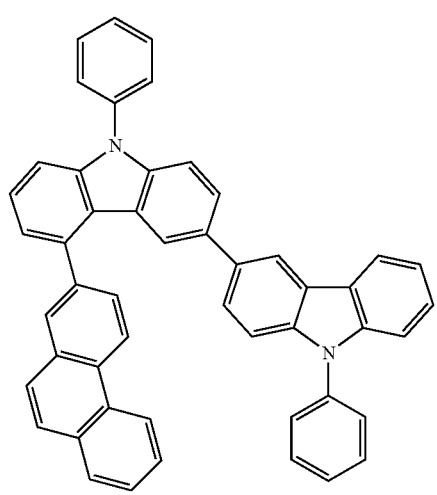
26

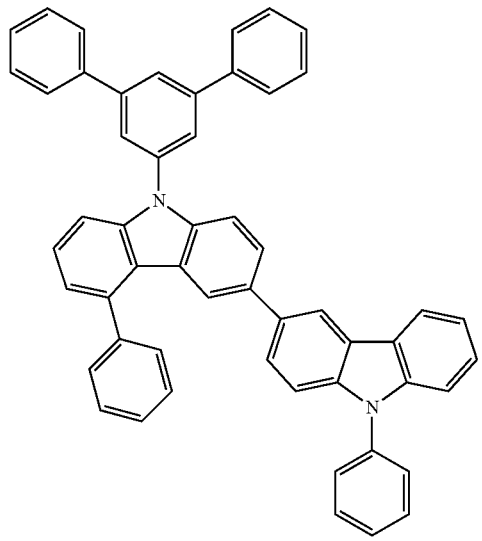
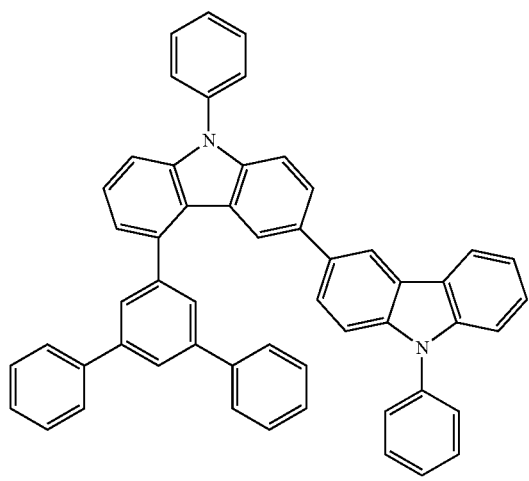
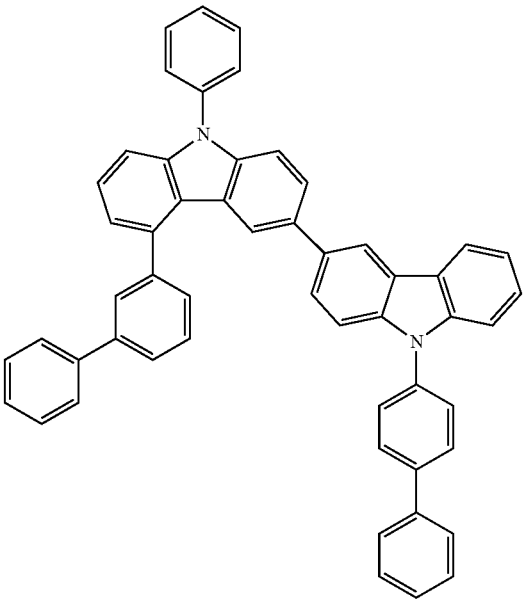
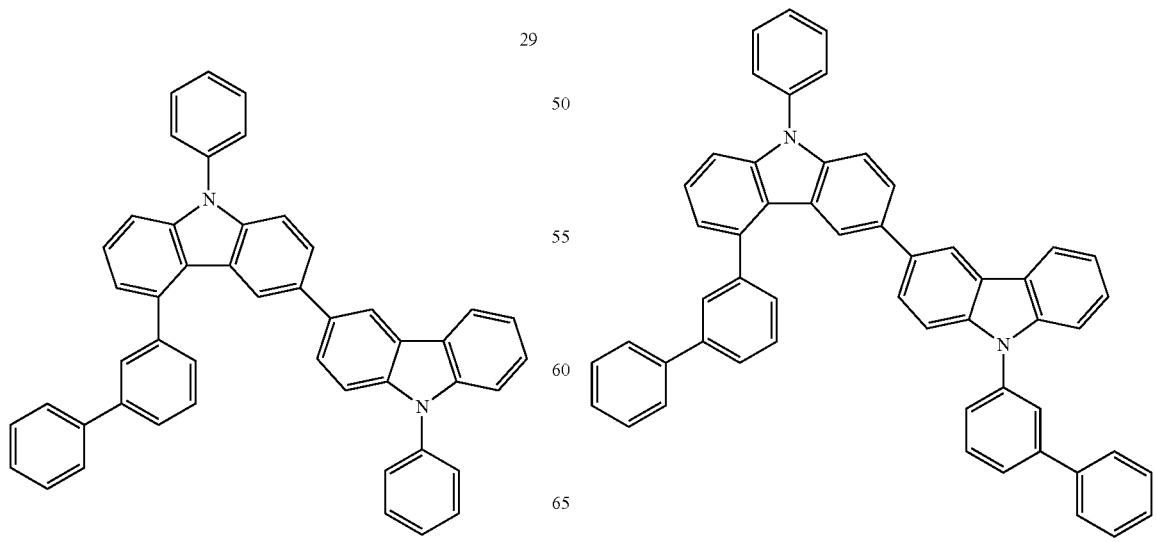

32
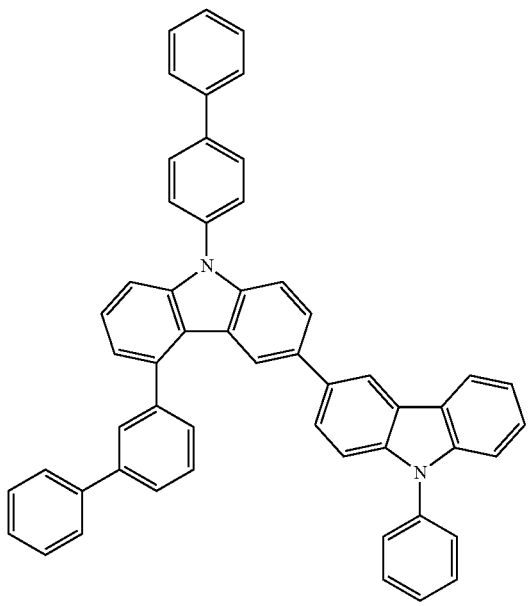
33
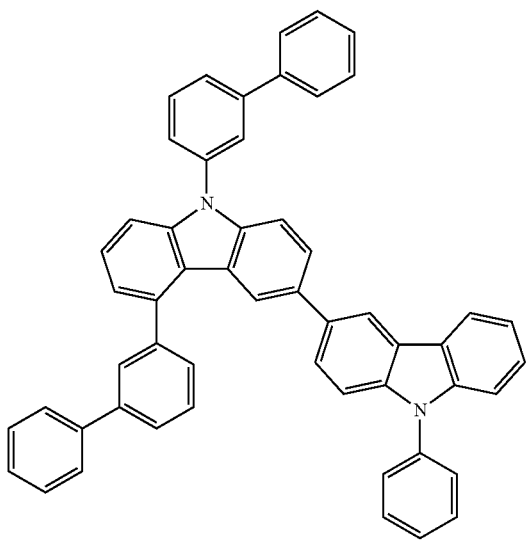
34
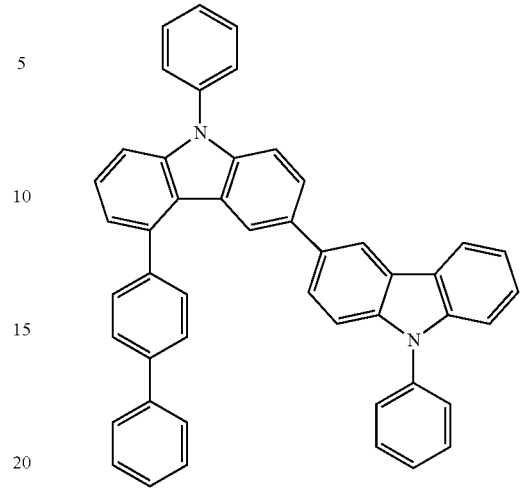
35
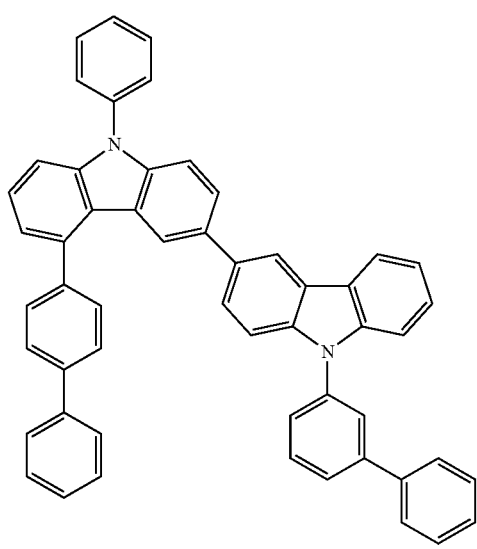
36
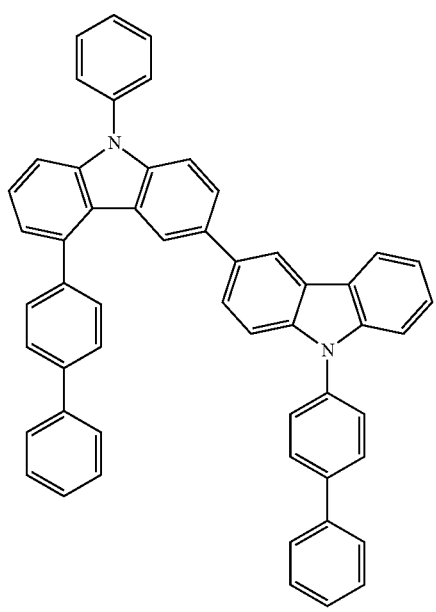

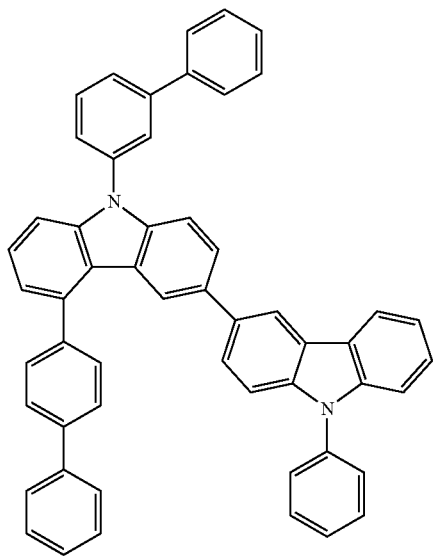
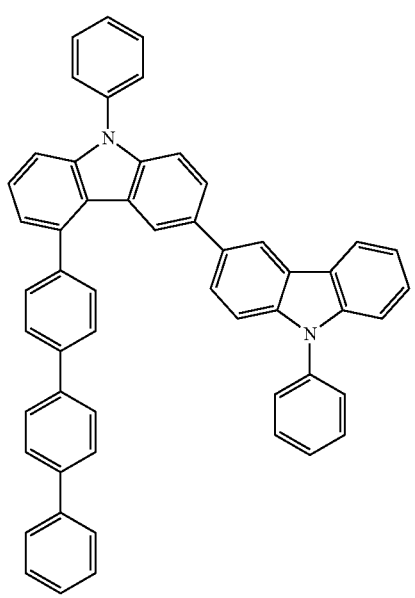
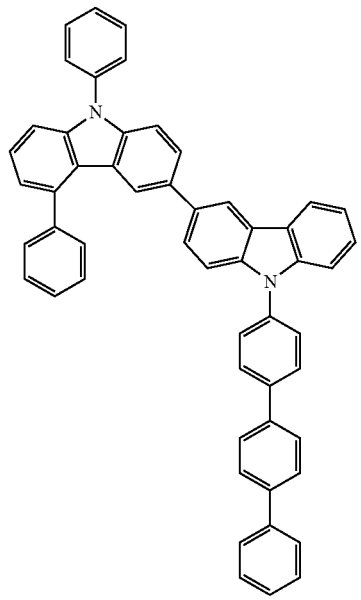

42
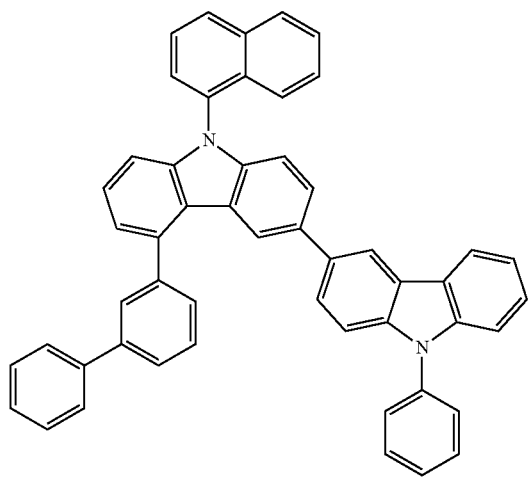
43
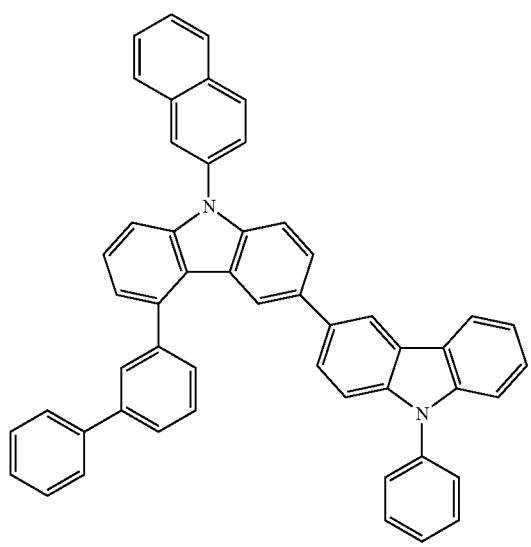
44
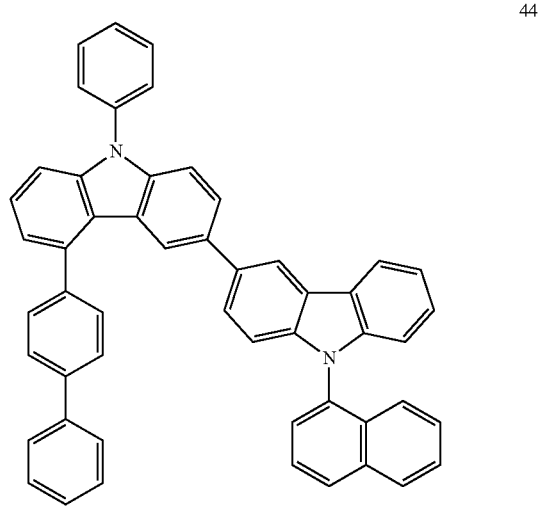
45
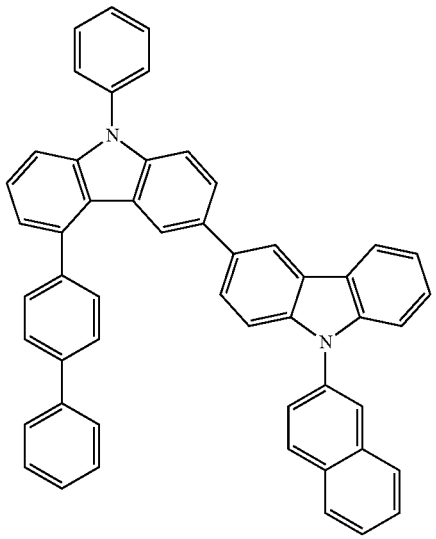
46
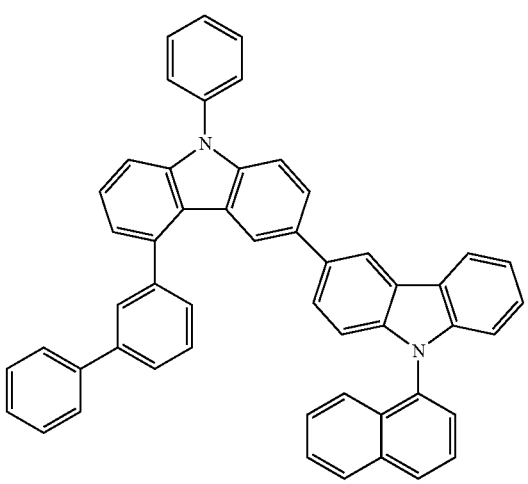
47
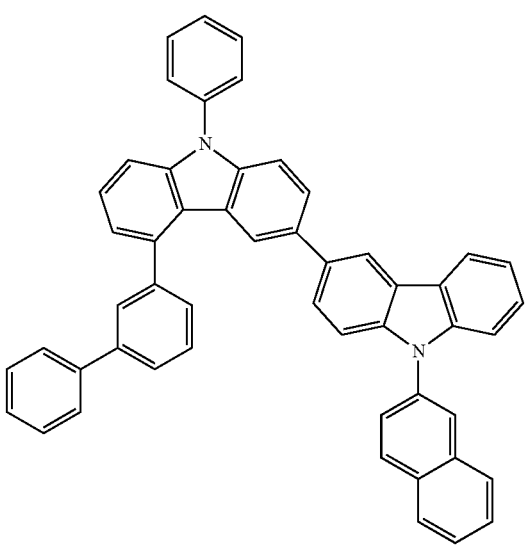

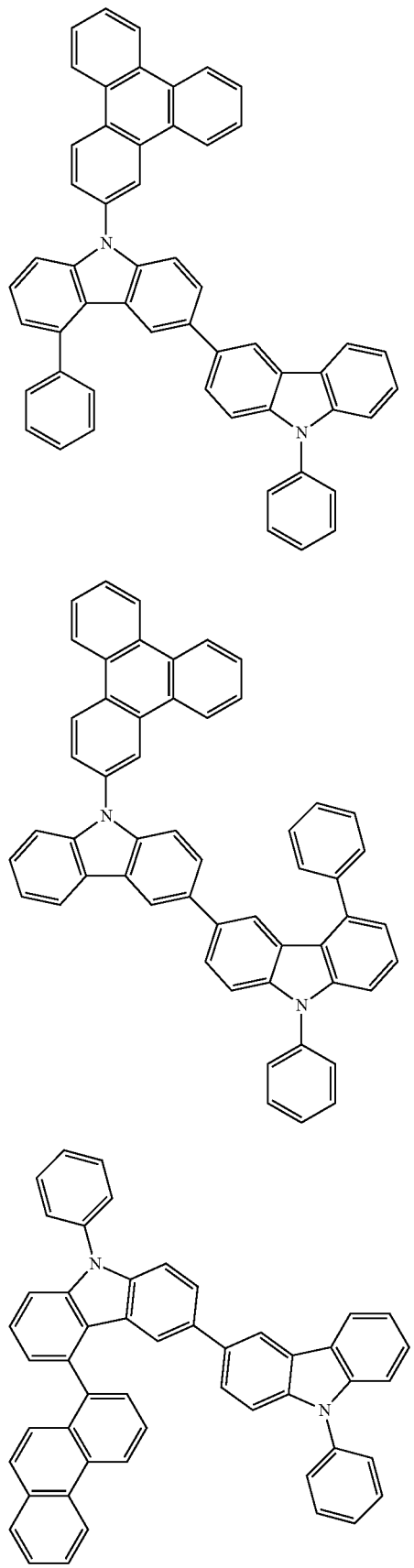
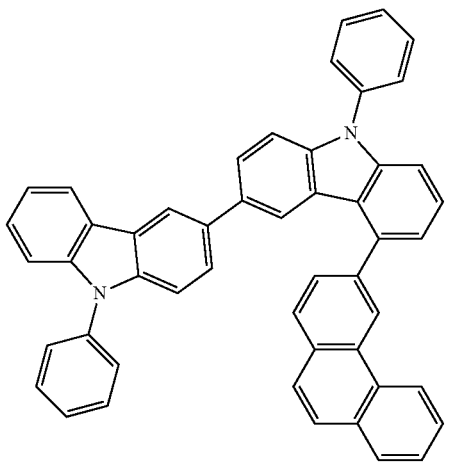
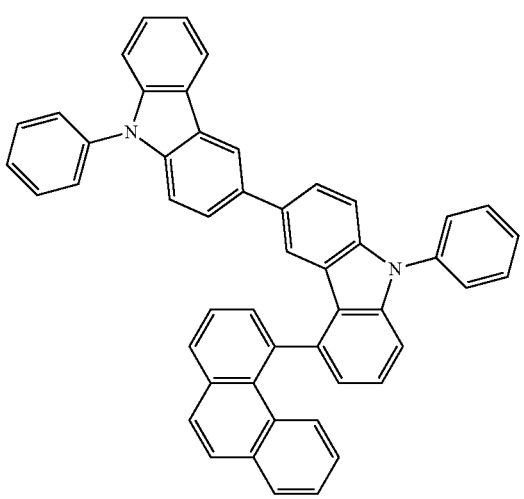
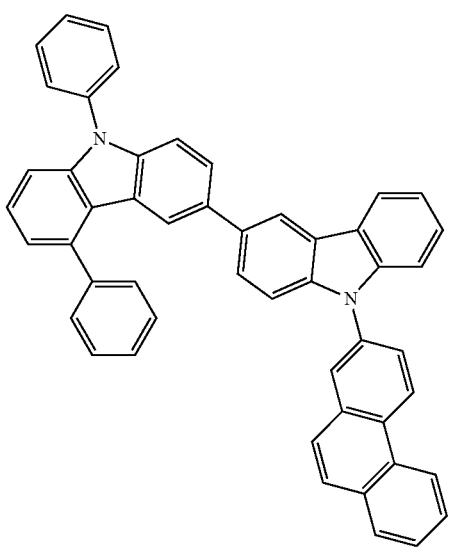

-continued

54

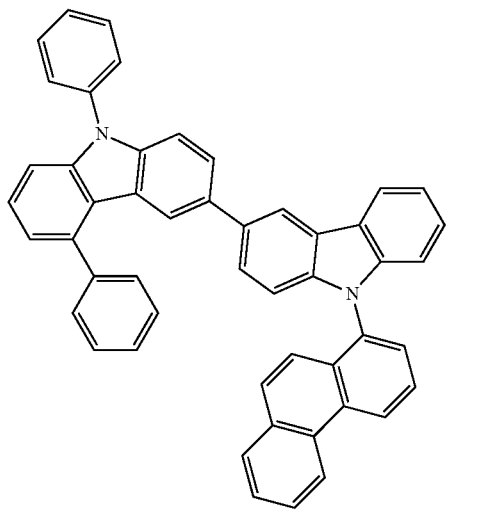

55

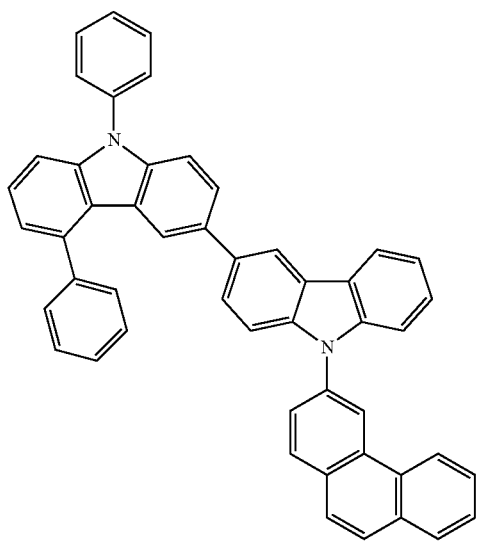

56

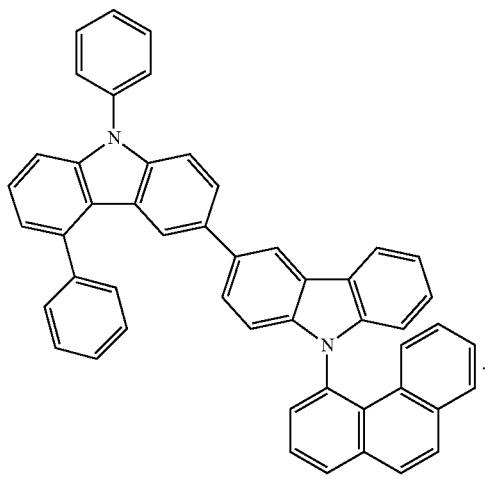

9. A composition for an organic optoelectric device, comprising:
   a first compound for an organic optoelectric device that is the compound as claimed in claim 1; and a second compound for an organic optoelectric device represented by Chemical Formula 2:

[Chemical Formula 2]

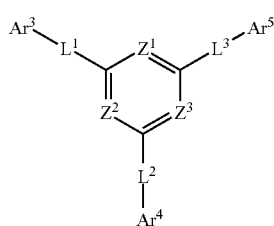

wherein, in Chemical Formula 2, $Z^1$ to $Z^3$ are independently N or $CR^a$, provided that at least two of $Z^1$ to $Z^3$ are N, $R^a$'s are independently hydrogen, deuterium, a substituted or unsubstituted C1 to C10 alkyl group, a substituted or unsubstituted C6 to C30 aryl group or a substituted or unsubstituted C2 to C30 heterocyclic group, wherein the $R^a$'s are independently present or adjacent groups are linked with each other to provide a substituted or unsubstituted aliphatic monocyclic or polycyclic ring, a substituted or unsubstituted aromatic monocyclic or polycyclic ring, or a substituted or unsubstituted heteroaromatic monocyclic or polycyclic ring, $Ar^3$ to $Ar^5$ are independently a substituted or unsubstituted C6 to C30 aryl group, a substituted or unsubstituted C2 to C30 heterocyclic group, or a combination thereof, $L^1$ to $L^3$ are independently a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

10. The composition for an organic optoelectric device as claimed in claim 9, wherein Chemical Formula 2 is represented by Chemical Formula 2-1, Chemical Formula 2-2, or Chemical Formula 2-3:

[Chemical Formula 2-1]

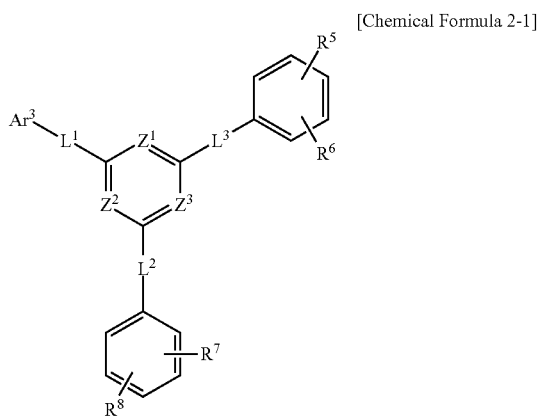

[Chemical Formula 2-2]

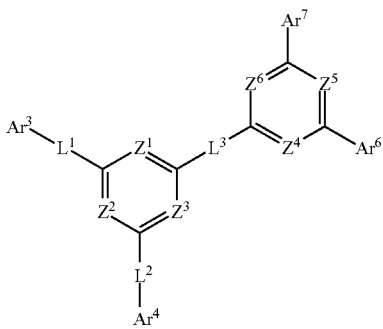

[Chemical Formula 2-3]

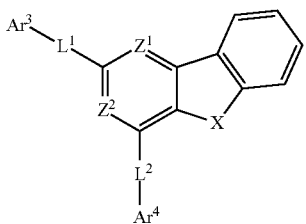

wherein, in each of respective Chemical Formulae 2-1 to 2-3, $Z^1$ to $Z^6$ are independently N or $CR^a$, provided that at least two of $Z^1$ to $Z^3$ are N and at least two of $Z^4$ to $Z^6$ are N, $Ar^3$ to $Ar^7$ are independently substituted or unsubstituted C6 to C30 aryl group, a substituted or unsubstituted C2 to C30 heterocyclic group, or a combination thereof, $R^a$ and $R^5$ to $R^8$ are independently hydrogen, deuterium, a substituted or unsubstituted C1 to C10 alkyl group, a substituted or unsubstituted C6 to C30 aryl group or a substituted or unsubstituted C2 to C30 heterocyclic group, and X is O or S.

11. The composition for an organic optoelectric device as claimed in claim 9, wherein $Ar^3$ to $Ar^5$ are independently a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted phenanthrene group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted indolocarbazolyl group, a substituted or unsubstituted indolobenzofuranyl group, a substituted or unsubstituted indolobenzothiophenyl group, a substituted or unsubstituted benzofuranpyrimidinyl group, or a substituted or unsubstituted benzothiophenepyrimidinyl group.

12. An organic optoelectric device, comprising:
an anode and a cathode facing each other, and
an organic layer disposed between the anode and the cathode,
wherein the organic layer includes the compound for an organic optoelectric device as claimed in claim 1.

13. The organic optoelectric device as claimed in claim 12, wherein:
the organic layer includes a light emitting layer, and
the compound for an organic optoelectric device is included as a host of the light emitting layer.

14. The organic optoelectric device as claimed in claim 13, wherein:
the organic layer further includes a hole auxiliary layer adjacent to the light emitting layer, and
the hole auxiliary layer includes the compound for an organic optoelectric device.

15. A display device comprising the organic optoelectric device as claimed in claim 12.

16. An organic optoelectric device, comprising:
an anode and a cathode facing each other, and
an organic layer disposed between the anode and the cathode,
wherein the organic layer includes the composition for an organic optoelectric device as claimed in claim 9.

17. The organic optoelectric device as claimed in claim 16, wherein:
the organic layer includes a light emitting layer, and
the composition for an organic optoelectric device is included as a host of the light emitting layer.

18. The organic optoelectric device as claimed in claim 17, wherein:
the organic layer further includes a hole auxiliary layer adjacent to the light emitting layer, and
the hole auxiliary layer includes the composition for an organic optoelectric device.

19. A display device comprising the organic optoelectric device as claimed in claim 16.

* * * * *